United States Patent
Novak, III et al.

(10) Patent No.: US 11,311,050 B2
(45) Date of Patent: *Apr. 26, 2022

(54) CONNECTORS FOR FORMING ELECTRICAL AND MECHANICAL CONNECTIONS BETWEEN INTERCHANGEABLE UNITS IN AN AEROSOL DELIVERY SYSTEM

(71) Applicant: RAI Strategic Holdings, Inc., Winston-Salem, NC (US)

(72) Inventors: Charles Jacob Novak, III, Winston-Salem, NC (US); Matthew Joel Nettenstrom, Bartlett, IL (US); Steven Michael Schennum, Plainfield, IL (US); Thomas Michael McKeon, Wheaton, IL (US); Zachary Hy Burchman, Chicago, IL (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/147,992

(22) Filed: Jan. 13, 2021

(65) Prior Publication Data
US 2021/0127744 A1     May 6, 2021

Related U.S. Application Data

(63) Continuation of application No. 17/025,237, filed on Sep. 18, 2020, now Pat. No. 10,939,702, which is a
(Continued)

(51) Int. Cl.
*A24F 40/42*     (2020.01)
*A61M 11/04*     (2006.01)
(Continued)

(52) U.S. Cl.
CPC ............ *A24F 40/42* (2020.01); *A24B 15/167* (2016.11); *A24D 1/002* (2013.01); *A24D 1/14* (2013.01);
(Continued)

(58) Field of Classification Search
CPC .. A24F 40/42; A24F 40/46; A24F 7/00; A24F 7/02; A61M 11/042;
(Continued)

(56) References Cited

U.S. PATENT DOCUMENTS 2,057,353 A    10/1936   Whittemore, Jr.
2,104,266 A     1/1938   McCormick
(Continued)

FOREIGN PATENT DOCUMENTS

CN    1541577    11/2004
CN    2719043     8/2005
(Continued)

OTHER PUBLICATIONS

International Search Report from corresponding International App. No. PCT/IB2019/058707, dated Jan. 17, 2020.

*Primary Examiner* — Tho D Ta
(74) *Attorney, Agent, or Firm* — Womble Bond Dickinson (US) LLP

(57) ABSTRACT

The present disclosure relates to aerosol delivery devices. In various implementations, the aerosol delivery devices comprise a control device that includes a battery, a control component, and an outer housing that defines receiving chamber, and a cartridge that includes a mouthpiece portion, a tank that contains a liquid composition, and a heater configured to heat the liquid composition. The cartridge and the control device each include at least one connector configured to provide a magnetic and an electrical connection between the cartridge and the control device such that
(Continued)

the cartridge can be removably and operatively received into the cartridge receiving chamber of the control body, wherein the at least one connector of the cartridge is located on the mouthpiece portion.

12 Claims, 48 Drawing Sheets

Related U.S. Application Data continuation of application No. 16/386,940, filed on Apr. 17, 2019, now Pat. No. 10,791,767.

(60) Provisional application No. 62/744,978, filed on Oct. 12, 2018.

(51) Int. Cl.
| | | |
|---|---|---|
| H05B 3/20 | (2006.01) | |
| H01R 13/17 | (2006.01) | |
| H01R 13/62 | (2006.01) | |
| A24D 1/14 | (2006.01) | |
| A24F 7/00 | (2006.01) | |
| A24B 15/167 | (2020.01) | |
| A24D 1/00 | (2020.01) | |
| A24F 7/02 | (2006.01) | |
| A24F 40/46 | (2020.01) | |
| A24F 40/40 | (2020.01) | |

(52) U.S. Cl.
CPC .................. *A24F 7/00* (2013.01); *A24F 7/02* (2013.01); *A24F 40/46* (2020.01); *A61M 11/042* (2014.02); *H01R 13/17* (2013.01); *H01R 13/6205* (2013.01); *H05B 3/20* (2013.01); *A24F 40/40* (2020.01); *A61M 11/041* (2013.01); *A61M 2205/0288* (2013.01); *A61M 2205/3368* (2013.01); *A61M 2205/50* (2013.01); *A61M 2205/584* (2013.01); *A61M 2205/587* (2013.01); *A61M 2205/8206* (2013.01); *H05B 2203/021* (2013.01)

(58) Field of Classification Search
CPC ......... A61M 2205/8206; A24B 15/167; A24D 1/002; A24D 1/14; H01R 13/17; H01R 13/6205; H05B 3/20
See application file for complete search history.

(56) References Cited

U.S. PATENT DOCUMENTS

| | | | |
|---|---|---|---|
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |
| 5,894,841 | A | 4/1999 | Voges |
| 6,125,853 | A | 10/2000 | Susa et al. |
| 6,155,268 | A | 12/2000 | Takeuchi |
| 7,117,867 | B2 | 10/2006 | Cox et al. |
| 7,832,410 | B2 | 11/2010 | Hon |
| 8,314,591 | B2 | 11/2012 | Terry et al. |
| 8,365,742 | B2 | 2/2013 | Hon |
| 8,499,766 | B1 | 8/2013 | Newton |
| 8,528,569 | B1 | 9/2013 | Newton |
| 8,833,364 | B2 | 9/2014 | Buchberger |
| 9,078,472 | B2 | 7/2015 | Liu |
| 9,220,304 | B2 | 12/2015 | Greim |
| 9,462,831 | B2 | 10/2016 | Liu |
| 9,609,893 | B2 | 4/2017 | Novak, III |
| 9,877,508 | B2 | 1/2018 | Kane |
| 10,015,990 | B2 | 7/2018 | Mironov |
| 10,028,537 | B1 | 7/2018 | Hawes et al. |
| 10,058,125 | B2 | 8/2018 | Worm et al. |
| 10,080,851 | B2 | 9/2018 | Davidson et al. |
| 10,085,481 | B2 | 10/2018 | Verleur et al. |
| 10,092,037 | B2 | 10/2018 | Tucker et al. |
| 10,104,913 | B2 | 10/2018 | Lau et al. |
| 10,117,463 | B2 | 11/2018 | Thomas |
| 10,117,467 | B2 | 11/2018 | Hawes et al. |
| 10,791,767 | B2 * | 10/2020 | Novak, III ............... H05B 3/20 |
| 10,939,702 | B2 * | 3/2021 | Novak, III ............... A24D 1/14 |
| 2005/0016550 | A1 | 1/2005 | Katase |
| 2006/0196518 | A1 | 9/2006 | Hon |
| 2008/0092912 | A1 | 4/2008 | Robinson et al. |
| 2009/0095311 | A1 | 4/2009 | Hon |
| 2009/0126745 | A1 | 5/2009 | Hon |
| 2009/0151717 | A1 | 6/2009 | Bowen et al. |
| 2009/0188490 | A1 | 7/2009 | Hon |
| 2009/0272379 | A1 | 11/2009 | Thorens et al. |
| 2009/0320863 | A1 | 12/2009 | Fernando et al. |
| 2011/0094523 | A1 | 4/2011 | Thorens et al. |
| 2011/0126848 | A1 | 6/2011 | Zuber et al. |
| 2011/0155718 | A1 | 6/2011 | Greim et al. |
| 2011/0168194 | A1 | 7/2011 | Hon |
| 2011/0265806 | A1 | 11/2011 | Alarcon et al. |
| 2013/0037041 | A1 | 2/2013 | Worm et al. |
| 2013/0042865 | A1 | 2/2013 | Monsees et al. |
| 2013/0306084 | A1 | 11/2013 | Flick |
| 2013/0319435 | A1 | 12/2013 | Flick |
| 2014/0000638 | A1 | 1/2014 | Sebastian et al. |
| 2014/0053858 | A1 * | 2/2014 | Liu ........................ A24F 40/95 131/329 |
| 2014/0096781 | A1 | 4/2014 | Sears et al. |
| 2014/0096782 | A1 | 4/2014 | Ampolini et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0366898 | A1 | 12/2014 | Monsees et al. |
| 2015/0020832 | A1 | 1/2015 | Greim et al. |
| 2015/0128976 | A1 | 5/2015 | Verleur et al. |
| 2015/0150308 | A1 | 6/2015 | Monsees et al. |
| 2015/0164142 | A1 | 6/2015 | Li et al. |
| 2015/0208729 | A1 | 7/2015 | Monsees et al. |
| 2015/0216233 | A1 | 8/2015 | Sears et al. |
| 2015/0305406 | A1 | 10/2015 | Li et al. |
| 2015/0313287 | A1 | 11/2015 | Verleur et al. |
| 2016/0278436 | A1 | 9/2016 | Verleur et al. |
| 2016/0345629 | A1 | 12/2016 | Mironov |
| 2016/0366947 | A1 | 12/2016 | Monsees et al. |
| 2017/0027226 | A1 | 2/2017 | Mironov et al. |
| 2017/0071256 | A1 | 3/2017 | Verleur et al. |
| 2017/0095005 | A1 | 4/2017 | Monsees et al. |
| 2017/0135404 | A1 | 5/2017 | Reevell |
| 2017/0135405 | A1 | 5/2017 | Reevell |
| 2017/0143042 | A1 | 5/2017 | Batista et al. |
| 2017/0215485 | A1 | 8/2017 | Zitzke |
| 2017/0231281 | A1 | 8/2017 | Hatton et al. |
| 2017/0231282 | A1 | 8/2017 | Hatton et al. |
| 2017/0325289 | A1 | 11/2017 | Liu |
| 2017/0340011 | A1 | 11/2017 | Batista |
| 2017/0340012 | A1 | 11/2017 | Mironov et al. |
| 2017/0347711 | A1 | 12/2017 | Litten et al. |
| 2017/0347712 | A1 | 12/2017 | Singh |
| 2018/0000157 | A1 | 1/2018 | Batista et al. |
| 2018/0000160 | A1 | 1/2018 | Taschner et al. |
| 2018/0014575 | A1 | 1/2018 | Fursa |
| 2018/0020731 | A1 | 1/2018 | Rasmussen et al. |
| 2018/0020736 | A1 | 1/2018 | Silvestrini |
| 2018/0035717 | A1 | 2/2018 | Batista |
| 2018/0042306 | A1 | 2/2018 | Atkins et al. |
| 2018/0043114 | A1 | 2/2018 | Bowen et al. |
| 2018/0070644 | A1 | 3/2018 | Monsees et al. |
| 2018/0077967 | A1 | 3/2018 | Hatton et al. |
| 2018/0084828 | A1 | 3/2018 | Phillips et al. |
| 2018/0084831 | A1 | 3/2018 | Mironov |
| 2018/0103685 | A1 | 4/2018 | Yener |
| 2018/0132525 | A1 | 5/2018 | Patil et al. |
| 2018/0140019 | A1 | 5/2018 | Guo et al. |
| 2018/0168225 | A1 | 6/2018 | Zinovik et al. |
| 2018/0177230 | A1 | 6/2018 | Hawes et al. |
| 2018/0213850 | A1 | 8/2018 | Brinkley et al. |

(56) References Cited

U.S. PATENT DOCUMENTS

| | | | |
|---|---|---|---|
| 2018/0242643 A1 | 8/2018 | Silvesstrini et al. |
| 2018/0279682 A1 | 10/2018 | Guo et al. |
| 2018/0280637 A1 | 10/2018 | Mayle et al. |
| 2018/0295888 A1 | 10/2018 | Newcomb et al. |
| 2018/0296777 A1 | 10/2018 | Terry et al. |

FOREIGN PATENT DOCUMENTS

| | | |
|---|---|---|
| CN | 201379072 | 1/2010 |
| CN | 105559150 | 5/2016 |
| CN | 106263031 | 1/2017 |
| CN | 207011690 | 2/2018 |
| CN | 107890142 | 4/2018 |
| EP | 1 618 803 | 1/2006 |
| EP | 2113178 | 4/2018 |
| WO | WO 2004/080216 | 9/2004 |
| WO | WO 2005/099494 | 10/2005 |
| WO | WO 2007/131449 | 11/2007 |
| WO | WO 2013/102611 | 7/2013 |
| WO | WO 2016/026811 | 2/2016 |
| WO | WO 2016/096497 | 6/2016 |
| WO | WO 2017/051006 | 9/2016 |
| WO | WO 2016/154797 | 10/2016 |
| WO | WO 2016/207442 | 5/2017 |
| WO | WO 2017/102969 | 6/2017 |
| WO | WO 2017/163046 | 9/2017 |
| WO | WO 2017/207442 | 12/2017 |
| WO | WO 2018/167166 | 9/2018 |
| WO | WO 2018/202732 | 11/2018 |

\* cited by examiner

CONNECTORS FOR FORMING ELECTRICAL AND MECHANICAL CONNECTIONS BETWEEN INTERCHANGEABLE UNITS IN AN AEROSOL DELIVERY SYSTEM

CROSS-REFERENCE TO RELATED APPLICATIONS

This application is a continuation application of U.S. patent application Ser. No. 17/025,237, filed on Sep. 18, 2020, titled Connectors For Forming Electrical and Mechanical Connections Between Interchangeable Units in an Aerosol Delivery System, which is a continuation application of U.S. patent application Ser. No. 16/386,940, issued as U.S. Pat. No. 10,791,767, filed on Apr. 17, 2019, titled Connectors For Forming Electrical and Mechanical Connections Between Interchangeable Units in an Aerosol Delivery System, which claims priority to, and the benefit of, U.S. Provisional Patent Application No. 62/744,978, filed on Oct. 12, 2018, titled Aerosol Forming Device, each of which is incorporated herein in its entirety by reference.

TECHNOLOGY FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices, and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., which are incorporated herein by reference in their entireties. See also, for example, the various types of smoking articles, aerosol delivery devices, and electrically powered heat generating sources referenced by brand name and commercial source in U.S. Pat. Pat. App. Pub. No. 2015/0216232, to Bless et al., which is incorporated herein by reference in its entirety. It would be desirable to provide an aerosol delivery device with advantageous usability features.

BRIEF SUMMARY

The present disclosure relates to aerosol delivery devices, methods of forming such devices, and elements of such devices. The disclosure particularly can relate to an aerosol delivery device and a cartridge for removable use with an aerosol delivery device. In this regard, various embodiments of the disclosure provide an aerosol delivery device with advantageous usability features, including, a control device and a cartridge, wherein electrical and mechanical connections are provided on the cartridge and control device allowing the cartridge to be removably and operatively connected to the control device.

In one implementation, the present disclosure provides an aerosol delivery device that comprises a control device that includes an outer housing defining an outer wall and having a proximal end and a distal end, the proximal end of the control device defining a cartridge receiving chamber, the control device further including a battery and a control component, and a cartridge that includes a mouthpiece portion and a tank, the mouthpiece portion having a proximal end and a distal end, the proximal end of the mouthpiece portion having an exit portal defined therethrough, the tank further defining a closed distal end and being configured to contain a liquid composition, the cartridge further including a heater configured to heat the liquid composition. The cartridge and the control device may each include at least one connector configured to provide a magnetic and an electrical connection between the cartridge and the control device such that the cartridge can be removably and operatively received into the cartridge receiving chamber of the control body, and the at least one connector of the cartridge may be located on the mouthpiece portion. In some implementations, the control device may further comprise an inner frame that defines the cartridge receiving chamber, wherein the inner frame includes an upper flange, a plurality of magnets spaced around the upper flange of the inner frame, and a pair of spring-loaded conductive pins located on the inner frame and below the upper flange thereof, the conductive pins being operatively connected to the battery, wherein the cartridge further comprises a flange located between the proximal and distal ends of the mouthpiece portion, a metal plate located below the flange, and a pair of conductive plugs, the conductive plugs being operatively connected to the heater, wherein when the cartridge is received into the cartridge receiving chamber, the magnetic connection is created between the magnets of the inner frame of the control device and the metal plate of the cartridge, and the electrical connection is created between the conductive pins of the inner frame of the control device and the conductive plugs of the cartridge. In some implementations, the magnets of the inner frame of the control device may be exposed in a top surface of the upper flange such that when the cartridge is received into the cartridge receiving chamber, the magnets of the inner frame of the control device make direct contact with the metal plate of the cartridge.

In some implementations, the control device may further comprise an inner frame that defines the cartridge receiving chamber, wherein the inner frame includes an upper portion, at least one attachment element located in the upper surface of the inner frame, and a pair of spring-loaded conductive pins located on the inner frame, the conductive pins being operatively connected to the battery, wherein the cartridge further comprises a flange located between the proximal and distal ends of the mouthpiece portion, at least one attachment element located in the flange of the cartridge, and a pair of conductive plugs, the conductive plugs being operatively connected to the heater, wherein when the cartridge is received into the cartridge receiving chamber, the magnetic connection is created between the at least one attachment element of the control device and the at least one attachment element of the cartridge, and the electrical connection is created between the conductive pins of the inner frame of the control device and the conductive plugs of the cartridge. In some implementations, the upper portion of the inner frame of the control device may include an angled surface, the at least one attachment element of the control device may comprise a plurality of magnets spaced around the angled surface of the inner frame, the flange of the cartridge may include a corresponding angled surface, and the at least one attachment element of the cartridge may comprise a plurality of magnets spaced around the angled surface of the flange. In some implementations, the upper portion of the inner frame of the control device may include an angled surface, the at least one attachment element of the control device may comprise a plurality of magnets spaced around the angled surface of the inner frame, the flange of the cartridge may include a corresponding angled surface, and the at least one attachment element of the cartridge may comprise a plurality of metal plates spaced around the angled surface of the flange. In some implementations, the upper portion of the inner frame of the control device may include an angled surface, the at least one attachment element of the control device may comprise a plurality of magnets spaced around the angled surface of the inner frame, the flange of the cartridge may include an angled surface, and the at least one attachment element may comprise a metal ring that comprises the angled surface of the flange. In some implementations, the at least one attachment element of the control device may comprise a magnetic ring that includes an angled surface that comprises the upper portion of the inner frame, the flange of the cartridge may include an angled surface, and the at least one attachment element of cartridge may comprise a metal ring that comprises the angled surface of the flange.

In some implementations, the control device may further comprise an inner frame that defines the cartridge receiving chamber, wherein the inner frame includes an upper portion, a pair of separate magnets that comprise a portion of the upper portion of the inner frame, wherein the cartridge further comprises a flange located between the proximal and distal ends of the mouthpiece portion, a pair of metal plates, the metal plates comprising a portion of the flange of the cartridge, and the metal plates being operatively connected to the heater, wherein when the cartridge is received into the cartridge receiving chamber, both the magnetic connection and the electrical connection are created between the pair of separate magnets of the inner frame of the control device and the pair of separate metal plates of the cartridge. In some implementations, the pair of separate magnets of the inner frame of the control device may include an angled surface, and the pair of metal plates of the flange of the cartridge may include a corresponding angled surface. In some implementations, the control device may further comprise an inner frame that defines the cartridge receiving chamber, a plurality of magnet spheres located in the inner frame, and a pair of spring-loaded conductive pins located on the inner frame, the conductive pins being operatively connected to the battery, wherein the cartridge further comprises a pair of metal plates, each metal plate including receiving detents on opposite ends thereof, the metal plates being operatively connected to the heater, wherein when the cartridge is received into the cartridge receiving chamber, the magnetic connection is created between the magnet spheres of the inner frame of the control device and the receiving detents of the metal plates of the cartridge, and the electrical connection is created between the conductive pins of the inner frame of the control device and the metal plates of the cartridge. In some implementations, the control device may further comprise an inner frame that defines the cartridge receiving chamber, a pair of angled magnets located in the inner frame, and a pair of spring-loaded conductive pins located in the inner frame and below the pair of angled magnets, the conductive pins being operatively connected to the battery, wherein the cartridge further comprises a flange located between the proximal and distal ends of the mouthpiece portion, a pair of pointed sliding metal plates located in the flange, and a pair of conductive plugs, the conductive plugs being operatively connected to the heater, wherein when the cartridge is received into the cartridge receiving chamber, the magnetic connection is created between the angled magnets of the inner frame of the control device and the pointed sliding metal plates of the cartridge, and the electrical connection is created between the conductive pins of the inner frame of the control device and the conductive plugs of the cartridge. In some implementations, the control device may further comprise an inner frame that defines the cartridge receiving chamber, wherein the inner frame includes an upper flange, a plurality of cylindrical magnets that extend into the upper flange of the inner frame, and a pair of spring-loaded conductive pins located on the inner frame and below the upper flange thereof, the conductive pins being operatively connected to the battery, wherein the cartridge further comprises a flange located between the proximal and distal ends of the mouthpiece portion, a metal plate located below the flange, and a pair of conductive plugs, the conductive plugs being operatively connected to the heater, wherein when the cartridge is received into the cartridge receiving chamber, the magnetic connection is created between the magnets of the inner frame of the control device and the metal plate of the cartridge, and the electrical connection is created between the conductive pins of the inner frame of the control device and the conductive plugs of the cartridge. In some implementations, the plurality of cylindrical magnets may extend through the upper flange of the inner frame such that a top surface of the magnets is substantially flush with a top surface of the upper flange.

In some implementations, the control device may further comprise an inner frame that defines the cartridge receiving chamber, wherein the inner frame includes an upper flange, a plurality of cylindrical magnets that extend into the upper flange of the inner frame, and a pair of spring-loaded conductive pins that extend into the upper flange of the inner frame, the conductive pins being operatively connected to the battery, wherein the cartridge further comprises a flange located between the proximal and distal ends of the mouthpiece portion, and a pair of metal plates comprising a portion of a bottom surface of the flange, the metal plates being operatively connected to the heater, wherein when the cartridge is received into the cartridge receiving chamber, the magnetic connection is created between the magnets of the inner frame of the control device and the metal plates of the cartridge, and the electrical connection is created between the conductive pins of the inner frame of the control device and the metal plates of the cartridge. In some implementations, the plurality of cylindrical magnets may extend through the upper flange of the inner frame such that a top surface of the magnets is substantially flush with a top surface of the upper flange. In some implementations, the control device may further comprise an inner frame that defines the cartridge receiving chamber, wherein the inner frame includes an upper flange, and a pair of cylindrical magnets that extend into the upper flange of the inner frame, the magnets being operatively connected to the battery, wherein the cartridge further comprises a flange located between the proximal and distal ends of the mouthpiece portion, and a pair of metal plates comprising a portion of a bottom surface of the flange, the metal plates being operatively connected to the heater, wherein when the cartridge is received into the cartridge receiving chamber, both the magnetic connection and the electrical connection are created between the magnets of the inner frame of the control device and the metal plates of the cartridge. In some implementations, the pair of cylindrical magnets may extend through the upper flange of the inner frame such that a top surface of the magnets is substantially flush with a top surface of the upper flange. In some implementations, the control device may further comprise an inner frame that defines the cartridge receiving chamber, wherein the inner frame includes an upper flange, a pair of cylindrical magnets that extend through the upper flange of the inner frame, and a pair of conductive casings, each conductive casing substantially surrounding a side surface of a respective magnet and extending through the upper flange of the inner frame such that a top edge of the casings is substantially flush with a top surface of the upper flange, the conductive casings being operatively connected to the battery, wherein the cartridge further comprises a flange located between the proximal and distal ends of the mouthpiece portion, and a pair of metal plates comprising a portion of a bottom surface of the flange, the metal plates being operatively connected to the heater, wherein when the cartridge is received into the cartridge receiving chamber, the magnetic connection is created between the magnets of the inner frame of the control device and the metal plates of the cartridge, and the electrical connection is created between the conductive casings of the inner frame of the control device and the metal plates of the cartridge.

In some implementations, the control device may further comprise an inner frame that defines the cartridge receiving chamber, wherein the inner frame includes an upper flange, a pair of cylindrical magnets that extend into the upper flange of the inner frame, and a pair of conductive casings, each conductive casing substantially surrounding a top and side surface of a respective magnet and extending through the upper flange of the inner frame such that a top surface of the casings is substantially flush with a top surface of the upper flange, the conductive casings being operatively connected to the battery, wherein the cartridge further comprises a flange located between the proximal and distal ends of the mouthpiece portion, and a pair of metal plates comprising a portion of a bottom surface of the flange, the metal plates being operatively connected to the heater, wherein when the cartridge is received into the cartridge receiving chamber, the magnetic connection is created between the magnets of the inner frame of the control device and the metal plates of the cartridge, and the electrical connection is created between the conductive casings of the inner frame of the control device and the metal plates of the cartridge. In some implementations, the control device may further comprise an inner frame that defines the cartridge receiving chamber, wherein the inner frame includes an upper flange, a plurality of magnets located in the upper flange of the inner frame, and a pair of metal plates located in the upper flange of the inner frame, a top surface of the metal plates being substantially flush with a top surface of the upper flange, the metal plates being operatively connected to the battery, wherein the cartridge further comprises a flange located between the proximal and distal ends of the mouthpiece portion, and first and second pairs of metal plates located below the flange, the first pair of metal plates being operatively connected to the heater, wherein when the cartridge is received into the cartridge receiving chamber, the magnetic connection is created between the magnets of the inner frame of the control device and the second pair of metal plates of the cartridge, and the electrical connection is created between the pair of metal plates of the inner frame of the control device and the first pair of metal plates of the cartridge. In some implementations, the control device may further comprise an inner frame that defines the cartridge receiving chamber, wherein the inner frame includes an upper flange, a plurality of magnets located in the upper flange of the inner frame; and a pair of metal plates located in the upper flange of the inner frame, a top surface of the metal plates being substantially flush with a top surface of the upper flange, the metal plates being operatively connected to the battery, wherein the cartridge further comprises a flange located between the proximal and distal ends of the mouthpiece portion, and a pair of metal plates located below the flange, the metal plates being operatively connected to the heater, wherein when the cartridge is received into the cartridge receiving chamber, the magnetic connection is created between the magnets of the inner frame of the control device and the pair of metal plates of the cartridge, and the electrical connection is created between the pair of metal plates of the inner frame of the control device and the pair of metal plates of the cartridge.

In some implementations, the control device may further comprise an inner frame that defines the cartridge receiving chamber, wherein the inner frame includes an upper flange, and a pair of magnets located in the upper flange of the inner frame and a pair of metal plates located in the upper flange of the inner frame, the metal plates being operatively connected to the battery, wherein the cartridge further comprises a flange located between the proximal and distal ends of the mouthpiece portion, and a pair of metal plates, the metal plates comprising a portion of the flange of the cartridge, the metal plates being operatively connected to the heater, wherein when the cartridge is received into the cartridge receiving chamber, the magnetic connection is created between the magnets of the inner frame of the control device and the pair of metal plates of the cartridge, and the electrical connection is created between the pair of metal plates of the inner frame of the control device and the pair of metal plates of the cartridge. In some implementations, the control device may further comprise an inner frame that defines the cartridge receiving chamber, wherein the inner frame includes an upper flange, and a pair of magnets located in the upper flange of the inner frame and a pair of metal plates located in the upper flange of the inner frame, the metal plates being operatively connected to the battery, wherein the cartridge further comprises a flange located between the proximal and distal ends of the mouthpiece portion, a metal ring that comprises a portion of the flange, and a pair of conductive spring contacts, the spring contacts being operatively connected to the heater, when the cartridge is received into the cartridge receiving chamber, the magnetic connection is created between the magnets of the inner frame of the control device and the metal ring of the cartridge, and the electrical connection is created between the pair of metal plates of the inner frame of the control device and the pair of conductive spring contacts of the cartridge. In some implementations, the control device may further comprise an inner frame that defines the cartridge receiving chamber, wherein the inner frame includes an upper flange, a plurality of cylindrical magnets that extend into the upper flange of the inner frame, and a pair of conductive pins that extend into the upper flange of the inner frame, the conductive pins being operatively connected to the battery, wherein the cartridge further comprises a flange located between the proximal and distal ends of the mouthpiece portion, and a pair of metal plates comprising a portion of a bottom surface of the flange, the metal plates being operatively connected to the heater, and each metal plate including an integrated spring contact, wherein when the cartridge is received into the cartridge receiving chamber, the magnetic connection is created between the magnets of the inner frame of the control device and the metal plates of the cartridge, and the electrical connection is created between the conductive pins of the inner frame of the control device and the integrated spring contacts of the metal plates of the cartridge.

In some implementations, the control device may further comprise an inner frame that defines the cartridge receiving chamber, wherein the inner frame includes an upper flange, a plurality of magnets spaced around the upper flange of the inner frame, and a pair of conductive spring contacts located on the inner frame and below the upper flange thereof, the spring contacts being operatively connected to the battery, wherein the cartridge further comprises a flange located between the proximal and distal ends of the mouthpiece portion, a metal plate located below the flange, and a pair of conductive plugs, the conductive plugs being operatively connected to the heater, wherein when the cartridge is received into the cartridge receiving chamber, the magnetic connection is created between the magnets of the inner frame of the control device and the metal plate of the cartridge, and the electrical connection is created between the conductive spring contacts of the inner frame of the control device and the conductive plugs of the cartridge. In some implementations, the control device may further comprise an inner frame that defines the cartridge receiving chamber, wherein the inner frame includes an upper portion, at least one attachment element located in the upper surface of the inner frame, and a pair of conductive spring contacts located on the inner frame, the conductive spring contacts being operatively connected to the battery, wherein the cartridge further comprises a flange located between the proximal and distal ends of the mouthpiece portion, at least one attachment element located in the flange of the cartridge, and a pair of conductive plugs, the conductive plugs being operatively connected to the heater, wherein when the cartridge is received into the cartridge receiving chamber, the magnetic connection is created between the at least one attachment element of the control device and the at least one attachment element of the cartridge, and the electrical connection is created between the conductive spring contacts of the inner frame of the control device and the conductive plugs of the cartridge. In some implementations, the control device may further comprise an inner frame that defines the cartridge receiving chamber, a plurality of magnet spheres located in the inner frame, and a pair of conductive spring contacts located on the inner frame, the conductive spring contacts being operatively connected to the battery, wherein the cartridge further comprises a pair of metal plates, each metal plate including receiving detents on opposite ends thereof, the metal plates being operatively connected to the heater, wherein when the cartridge is received into the cartridge receiving chamber, the magnetic connection is created between the magnet spheres of the inner frame of the control device and the receiving detents of the metal plates of the cartridge, and the electrical connection is created between the conductive spring contacts of the inner frame of the control device and the metal plates of the cartridge.

In some implementations, the control device may further comprise an inner frame that defines the cartridge receiving chamber, a pair of angled magnets located in the inner frame, and a pair of conductive spring contacts located in the inner frame and below the pair of angled magnets, the conductive pins being operatively connected to the battery, wherein the cartridge further comprises a flange located between the proximal and distal ends of the mouthpiece portion, a pair of pointed sliding metal plates located in the flange, and a pair of conductive plugs, the conductive plugs being operatively connected to the heater, wherein when the cartridge is received into the cartridge receiving chamber, the magnetic connection is created between the angled magnets of the inner frame of the control device and the pointed sliding metal plates of the cartridge, and the electrical connection is created between the conductive spring contacts of the inner frame of the control device and the conductive plugs of the cartridge. In some implementations, the control device may further comprise an inner frame that defines the cartridge receiving chamber, wherein the inner frame includes an upper flange, a plurality of cylindrical magnets that extend into the upper flange of the inner frame, and a pair of conductive spring contacts located on the inner frame and below the upper flange thereof, the conductive pins being operatively connected to the battery, wherein the cartridge further comprises a flange located between the proximal and distal ends of the mouthpiece portion, a metal plate located below the flange, and a pair of conductive plugs, the conductive plugs being operatively connected to the heater, wherein when the cartridge is received into the cartridge receiving chamber, the magnetic connection is created between the magnets of the inner frame of the control device and the metal plate of the cartridge, and the electrical connection is created between the conductive spring contacts of the inner frame of the control device and the conductive plugs of the cartridge. In some implementations, the control device may further comprise an inner frame that defines the cartridge receiving chamber, wherein the inner frame includes an upper flange, a plurality of cylindrical magnets that extend into the upper flange of the inner frame, and a pair of conductive spring contacts that extend into the upper flange of the inner frame, the conductive pins being operatively connected to the battery, wherein the cartridge further comprises a flange located between the proximal and distal ends of the mouthpiece portion, and a pair of metal plates comprising a portion of a bottom surface of the flange, the metal plates being operatively connected to the heater, wherein when the cartridge is received into the cartridge receiving chamber, the magnetic connection is created between the magnets of the inner frame of the control device and the metal plates of the cartridge, and the electrical connection is created between the conductive spring contacts of the inner frame of the control device and the metal plates of the cartridge.

These and other features, aspects, and advantages of the disclosure will be apparent from a reading of the following detailed description together with the accompanying drawings, which are briefly described below.

BRIEF DESCRIPTION OF THE DRAWINGS

Figure 1:
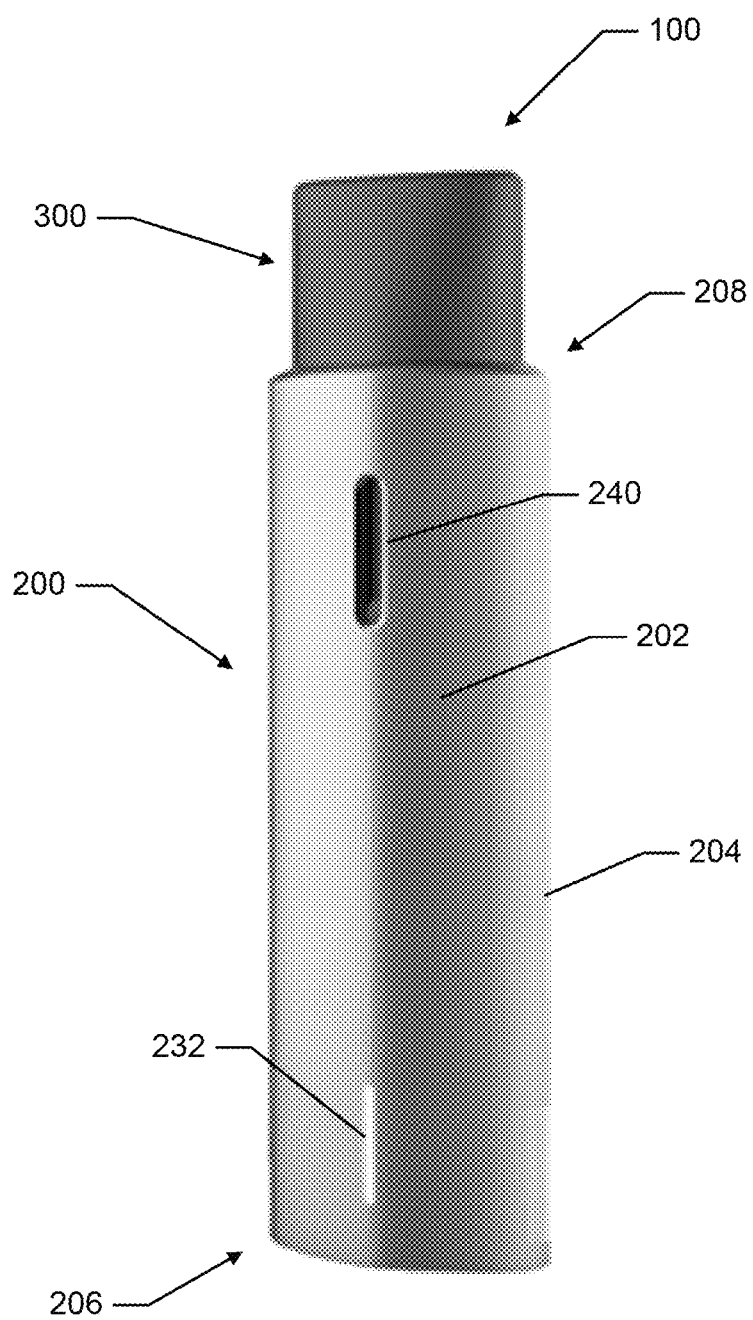
Figure 2:
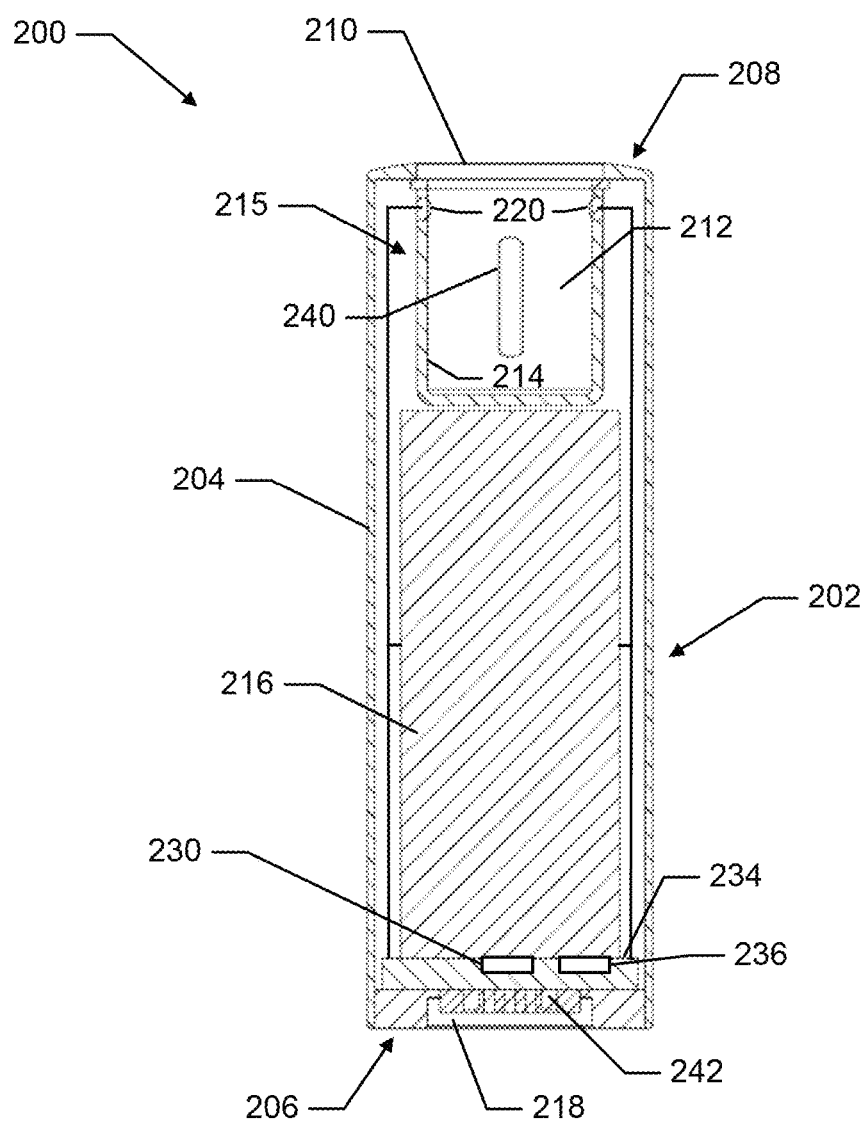
Figure 3A:
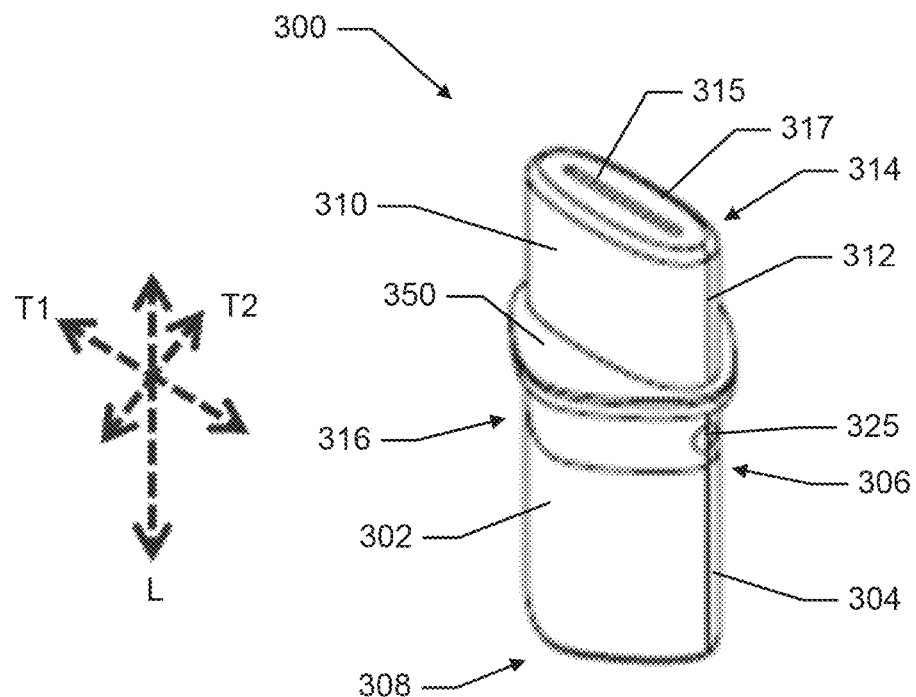
Figure 3B:
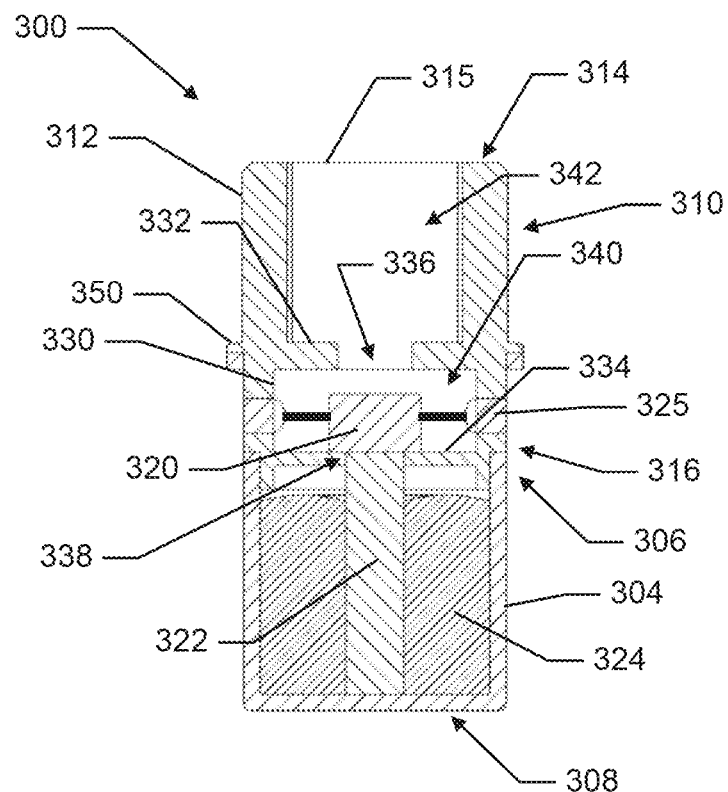
Figure 4A:
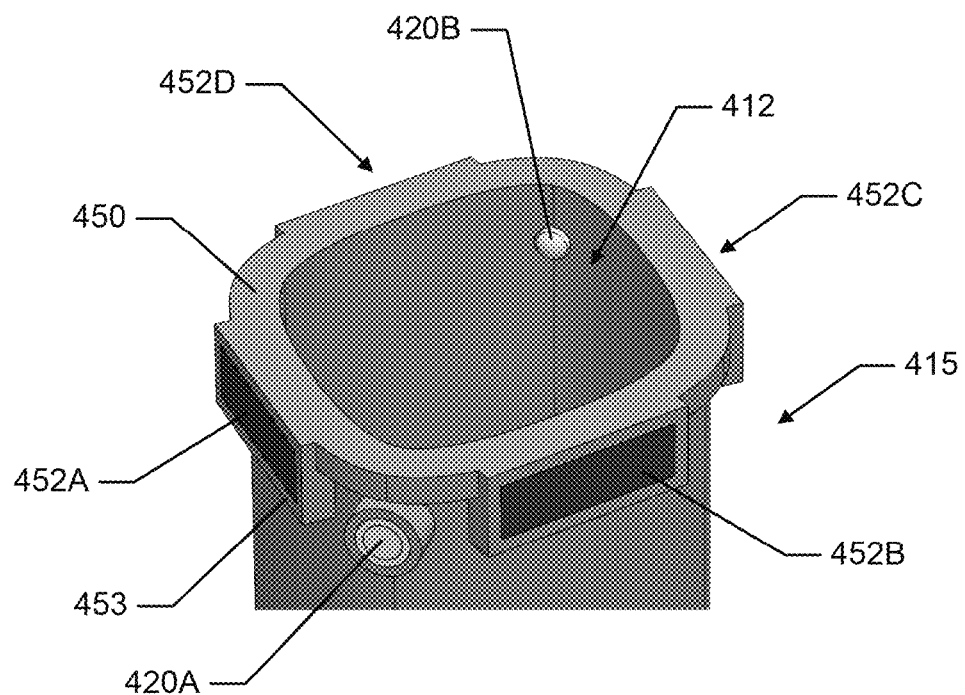
Figure 4B:
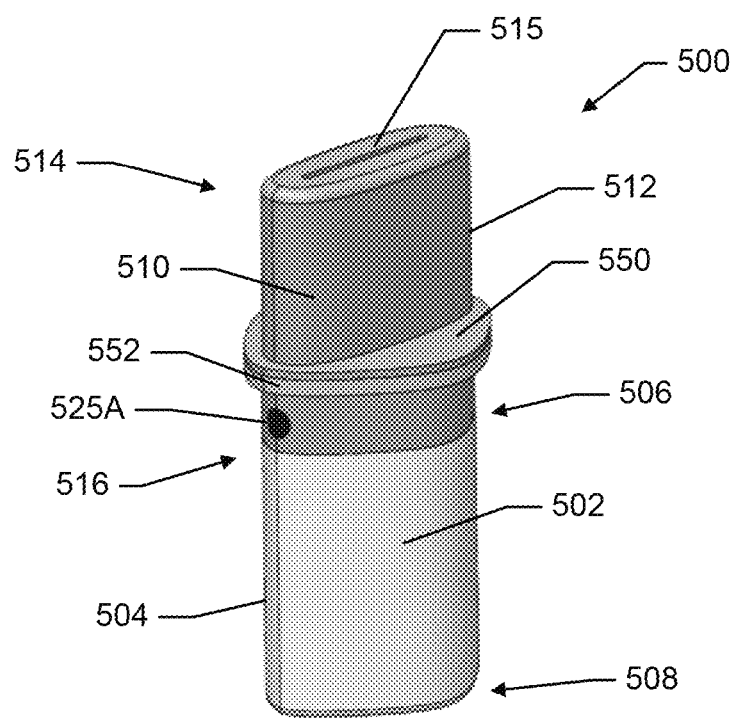
Figure 5:
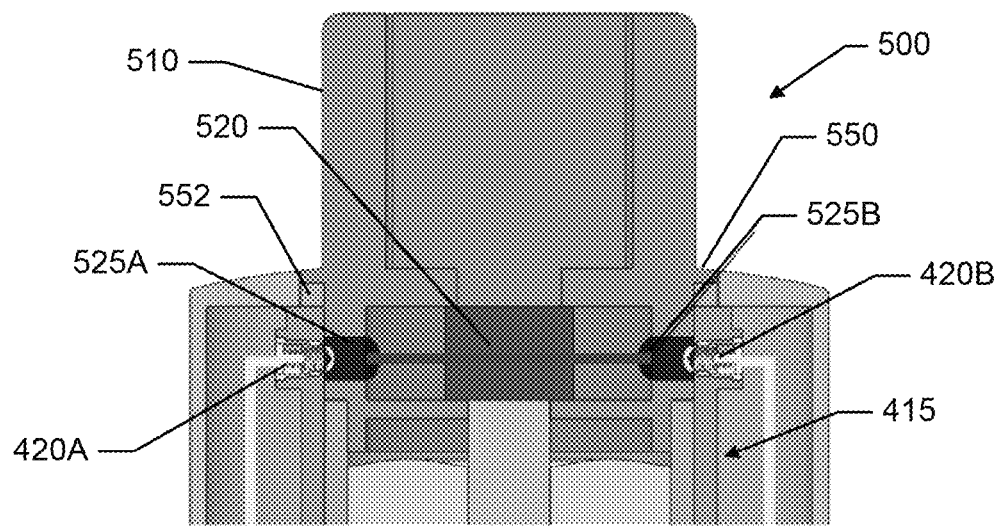
Figure 6:
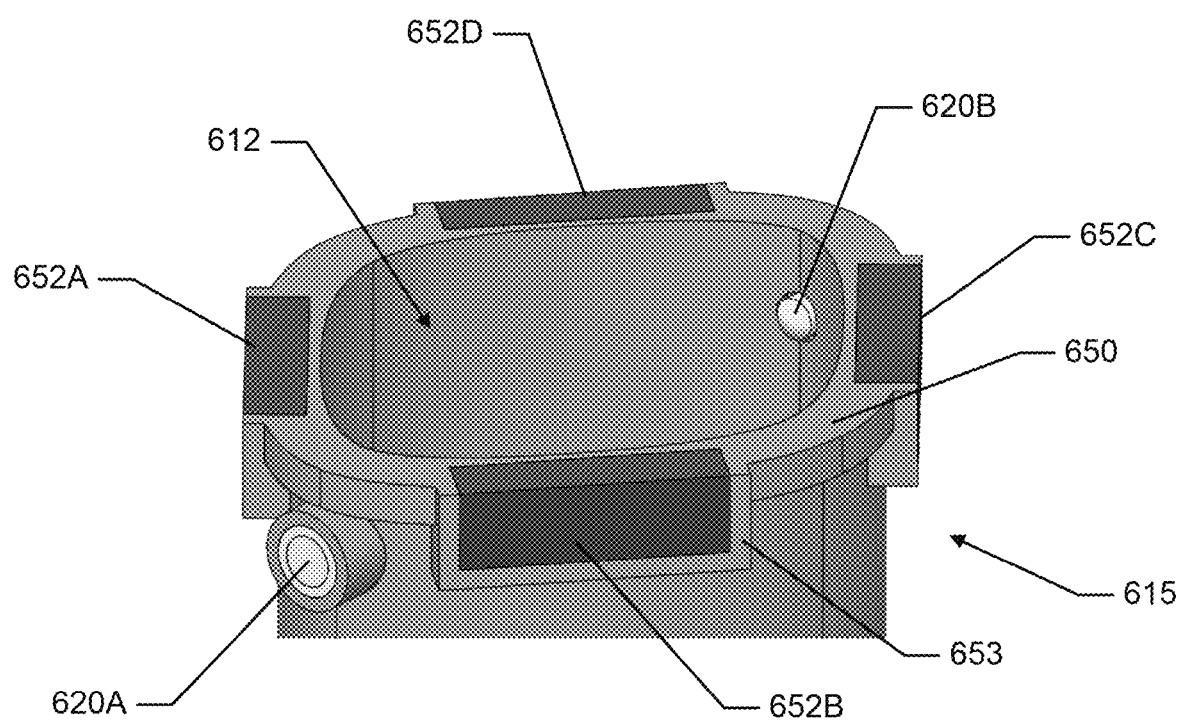
Figure 7:
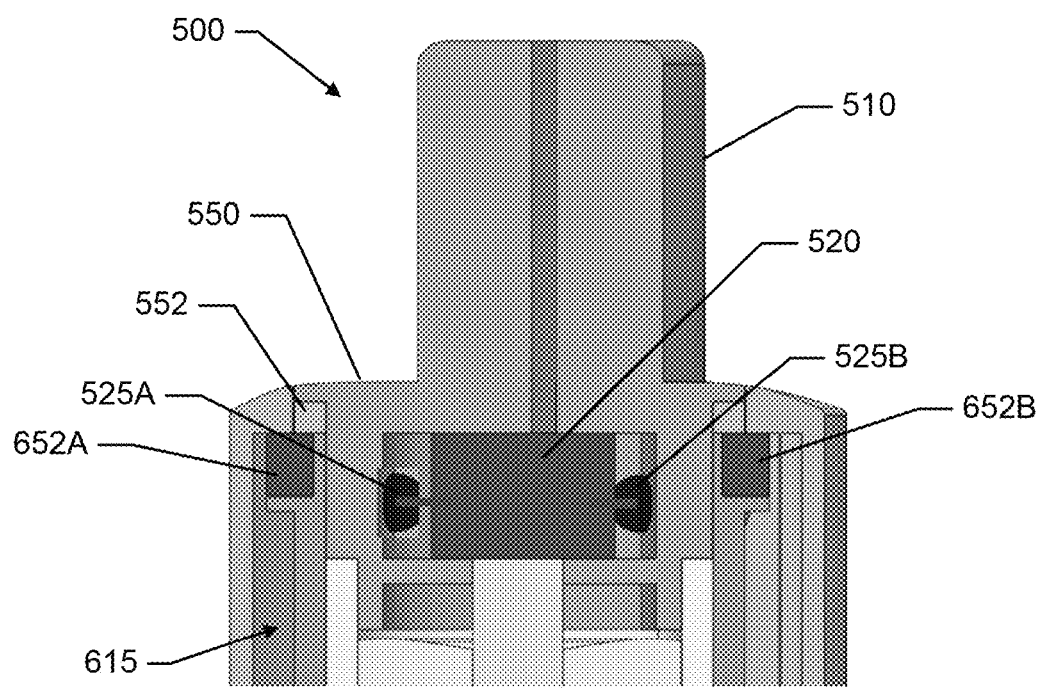
Figure 8A:
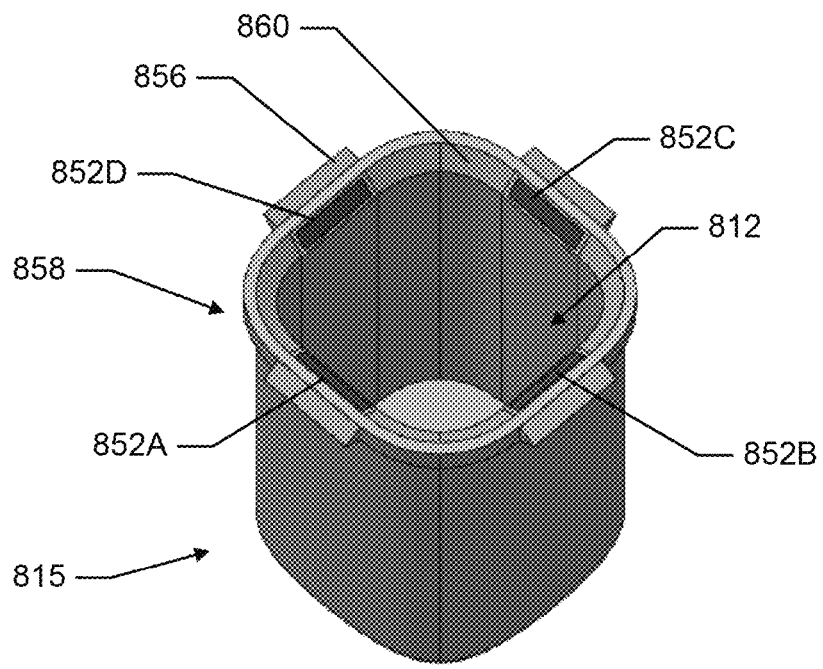
Figure 8B:
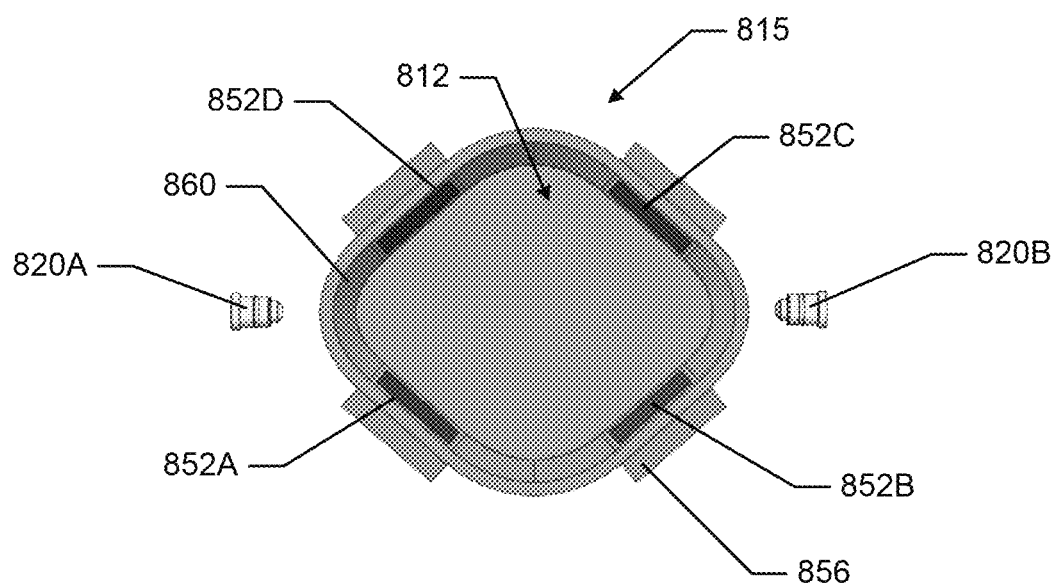
Figure 8C:
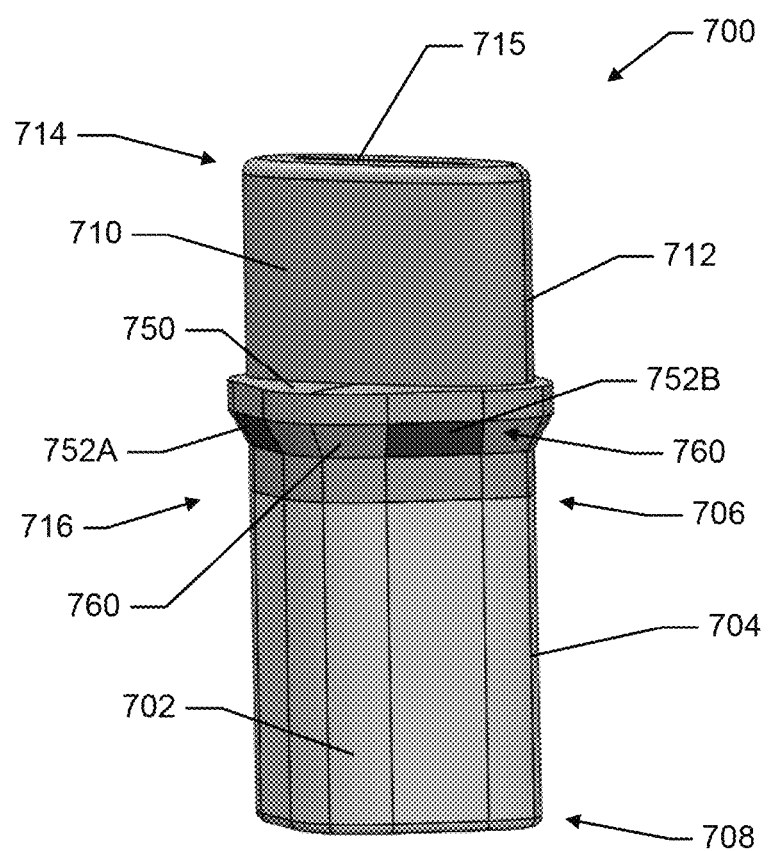
Figure 9:
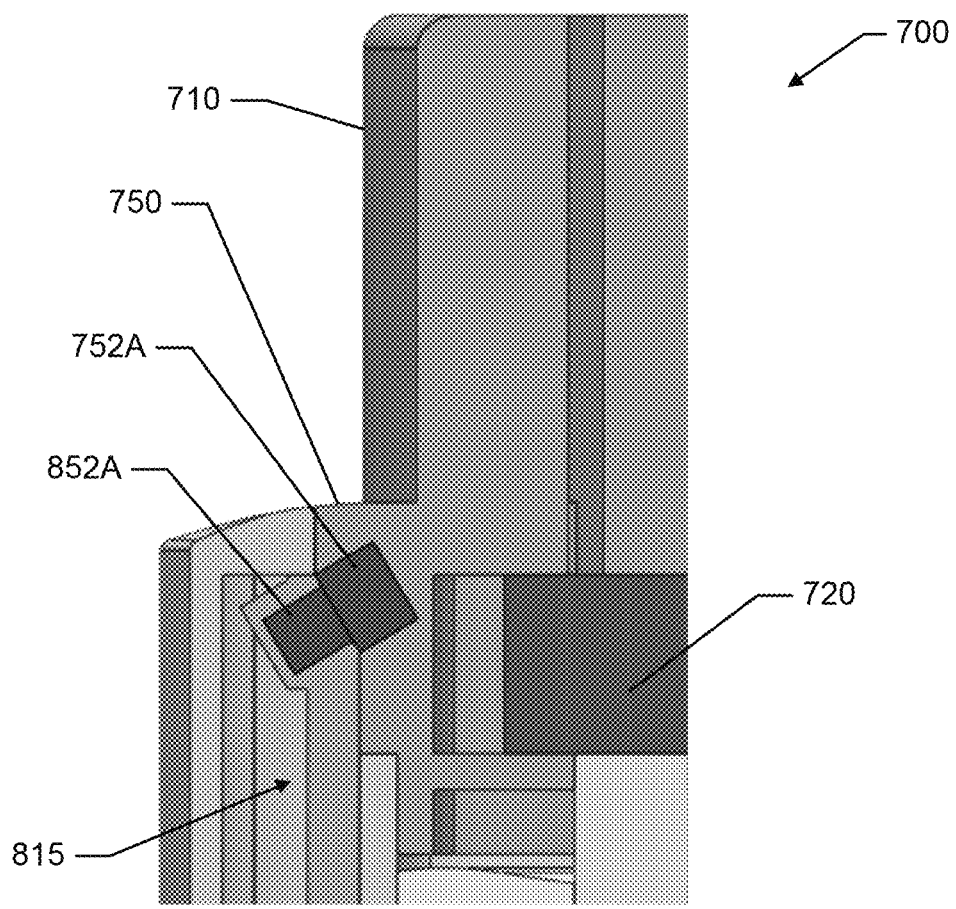
Figure 10A:
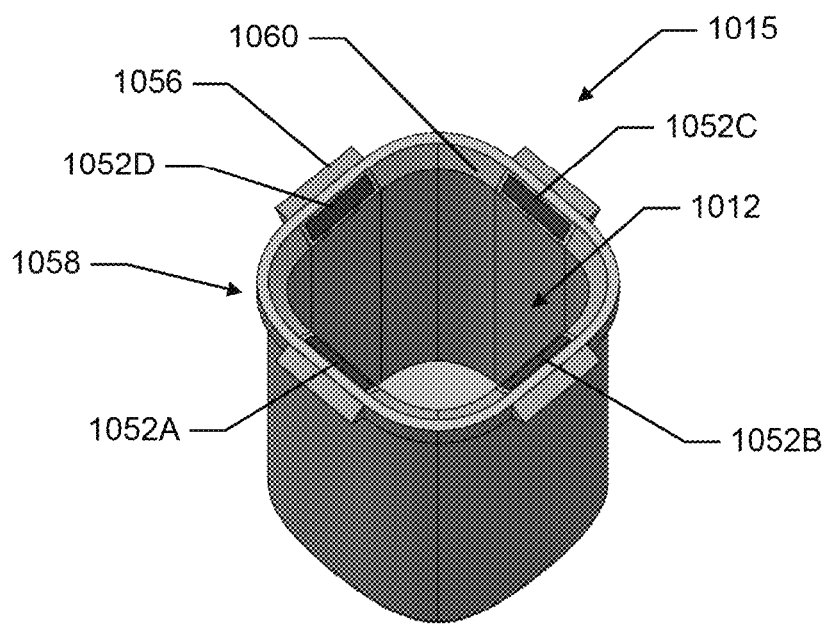
Figure 10B:
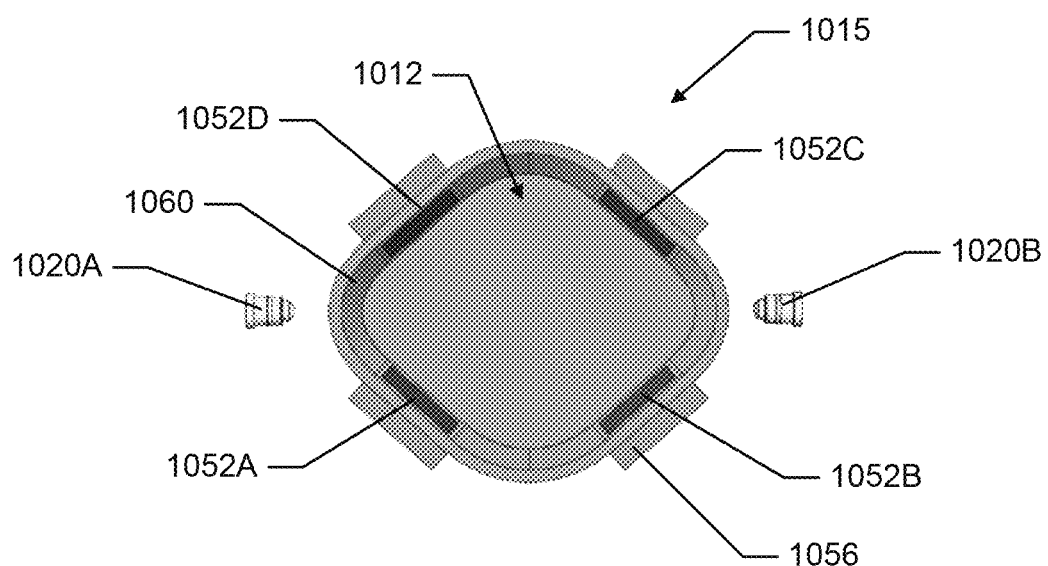
Figure 10C:
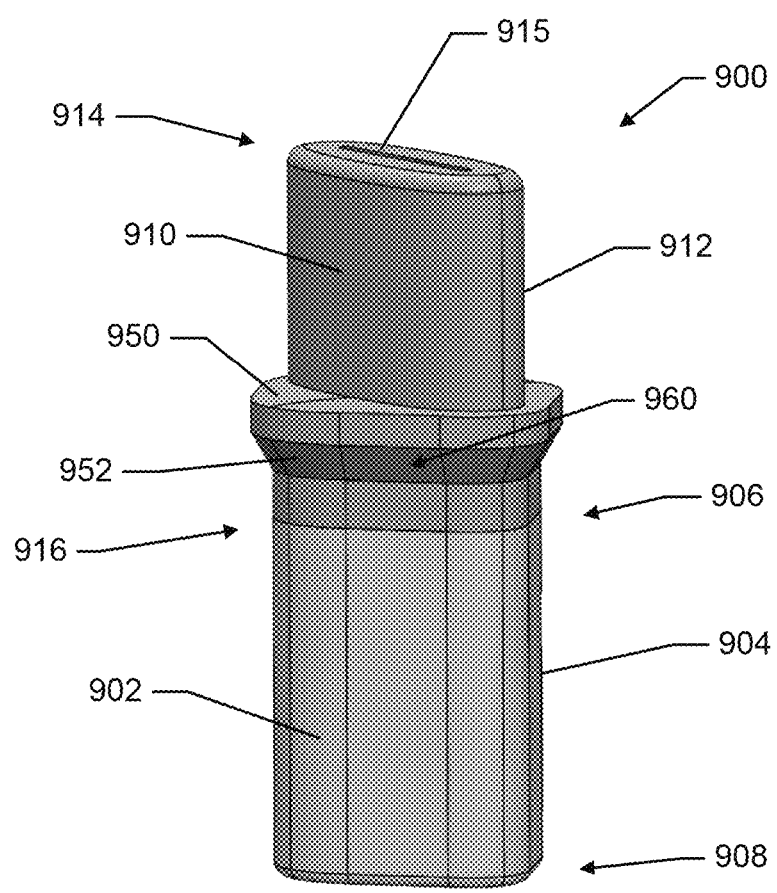
Figure 11:
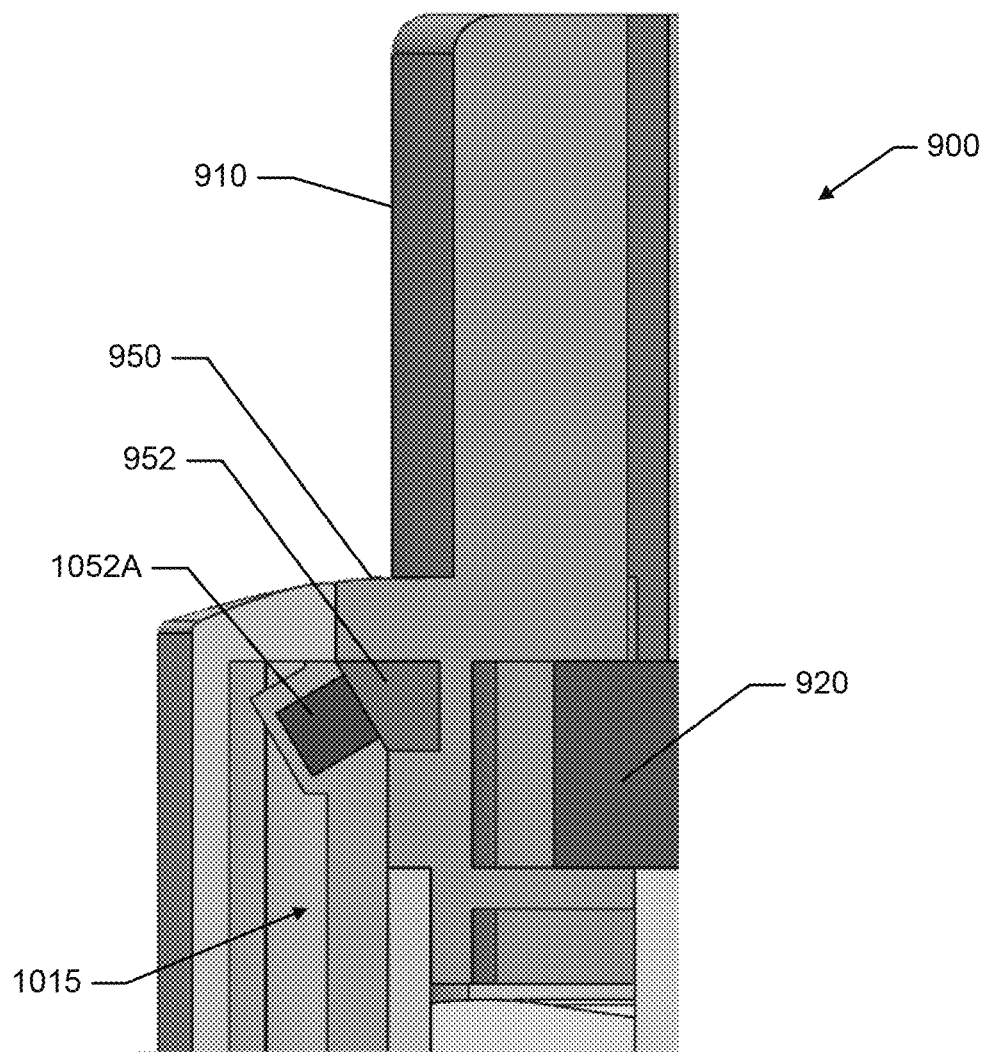
Figure 12A:
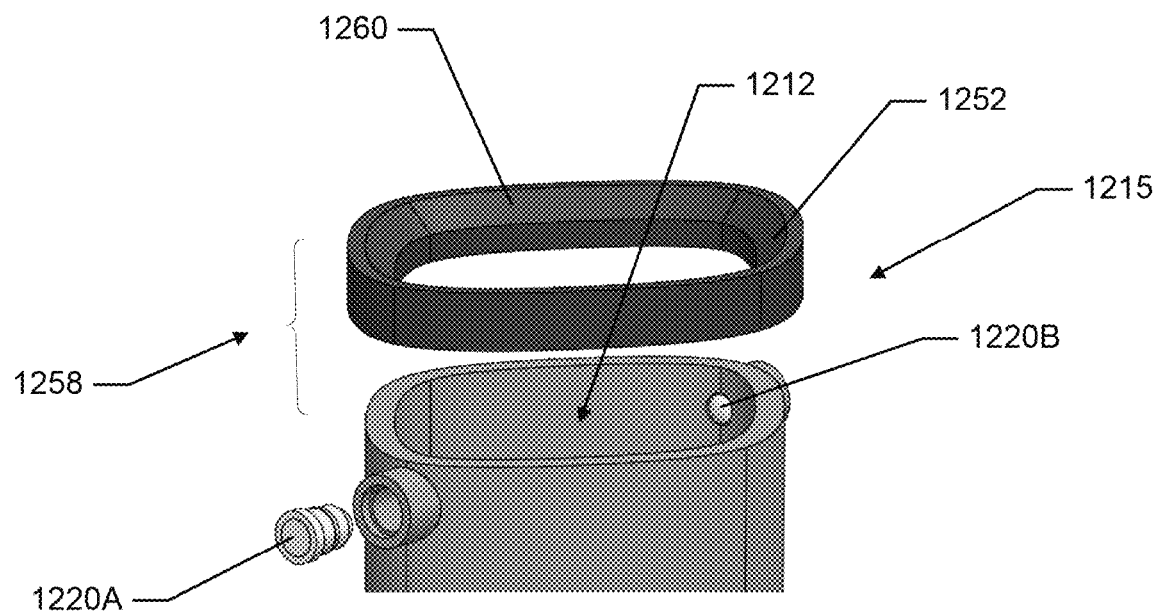
Figure 12B:
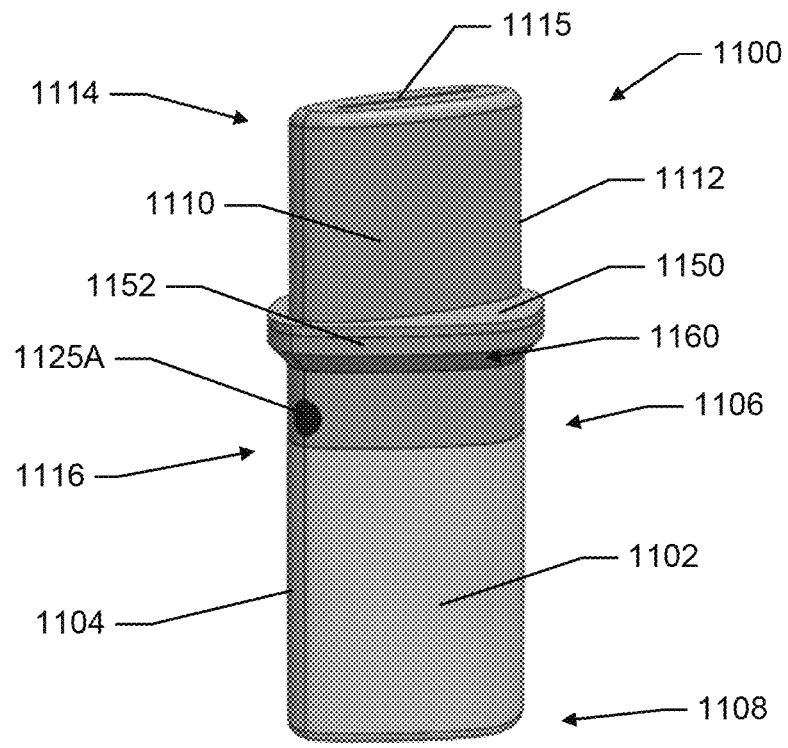
Figure 13:
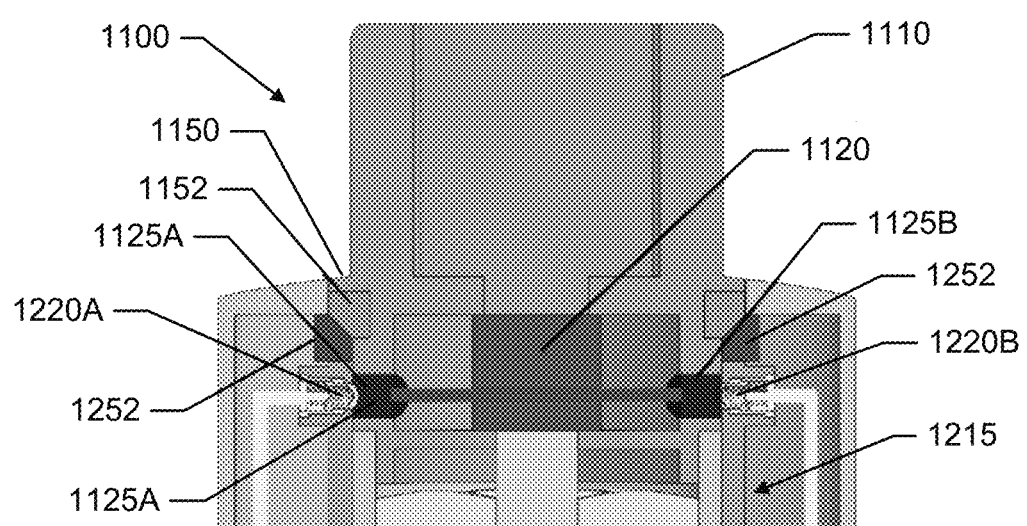
Figure 14A:
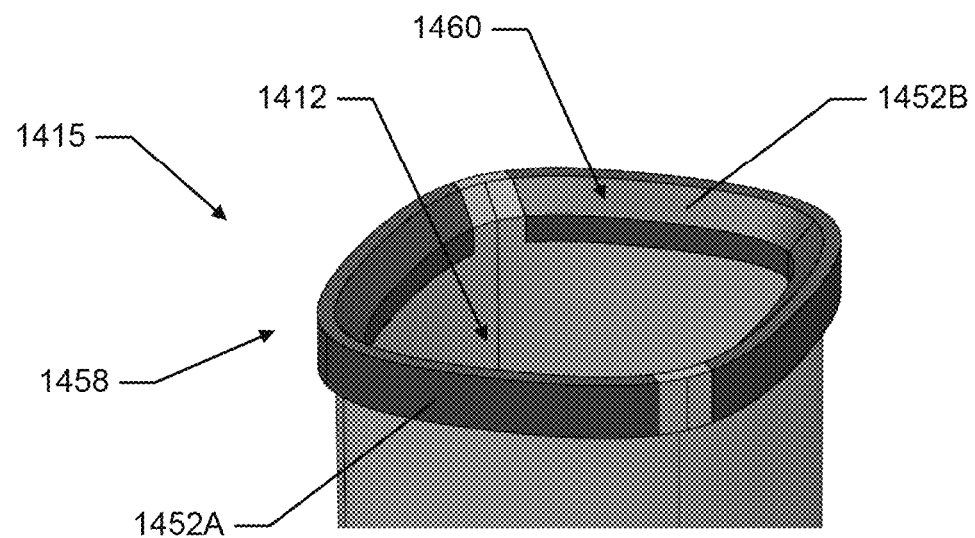
Figure 14B:
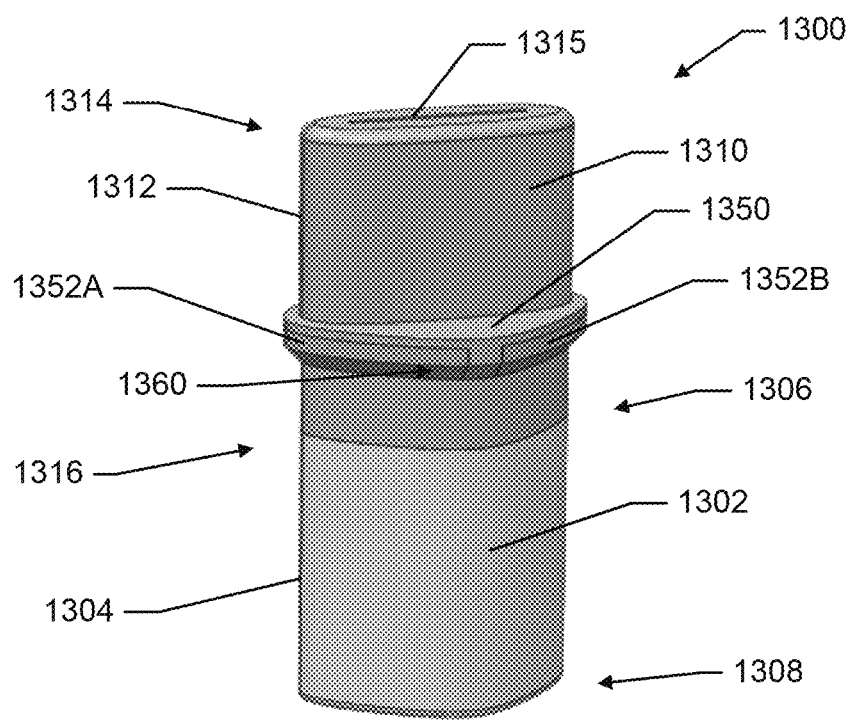
Figure 14C:
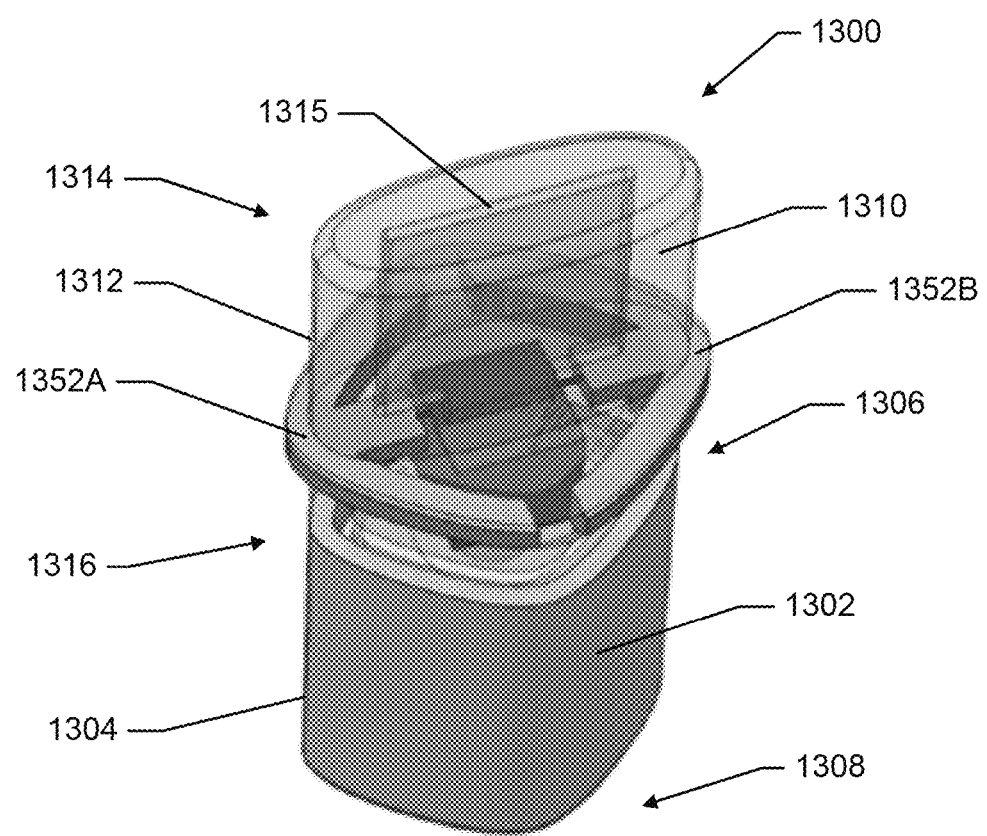
Figure 15:
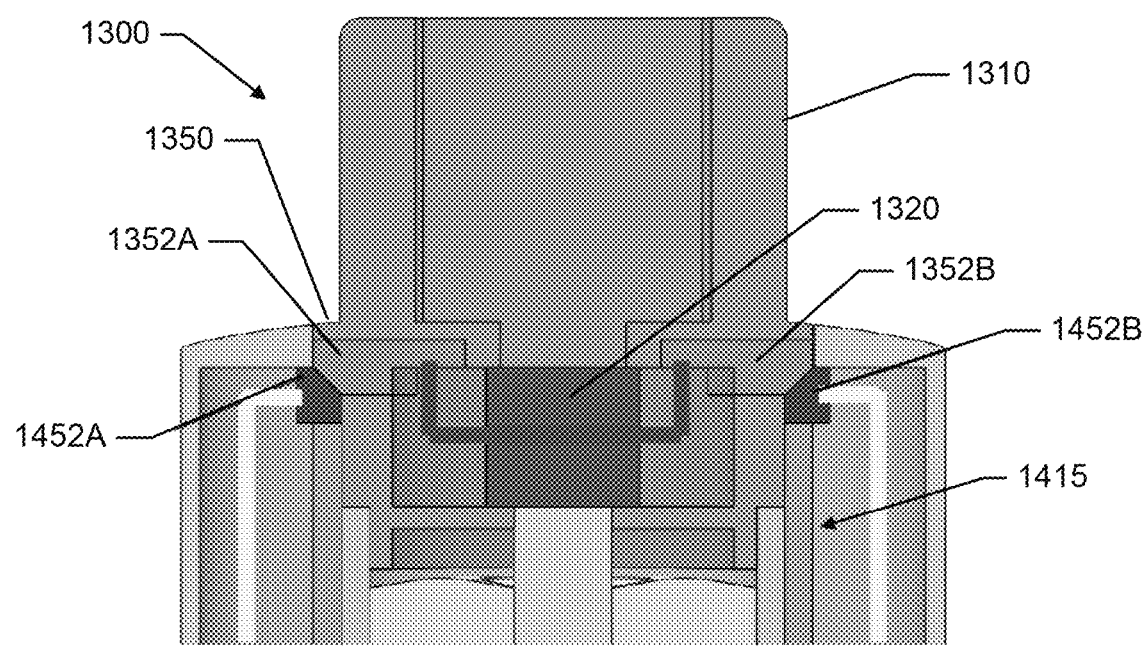
Figure 16A:
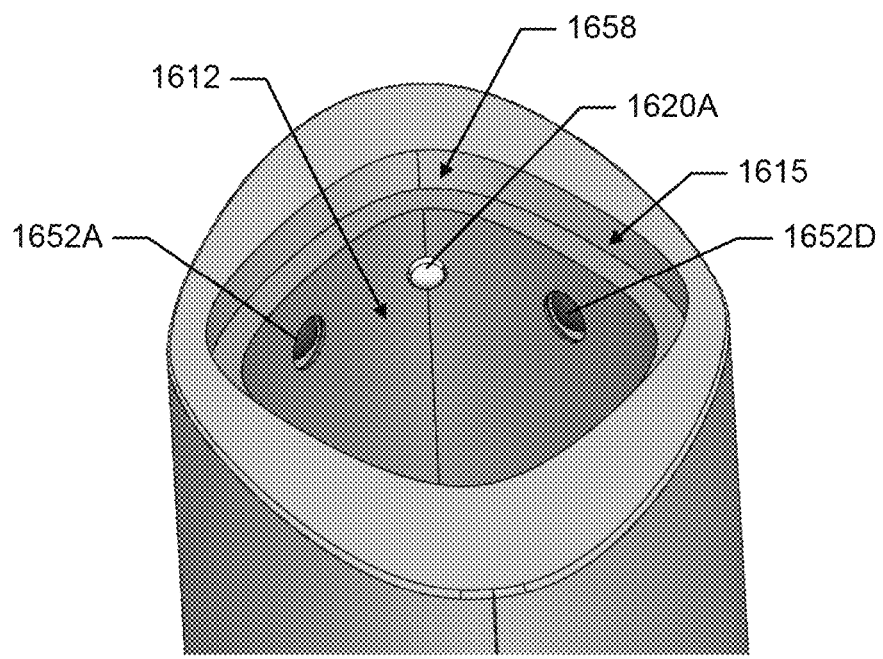
Figure 16B:
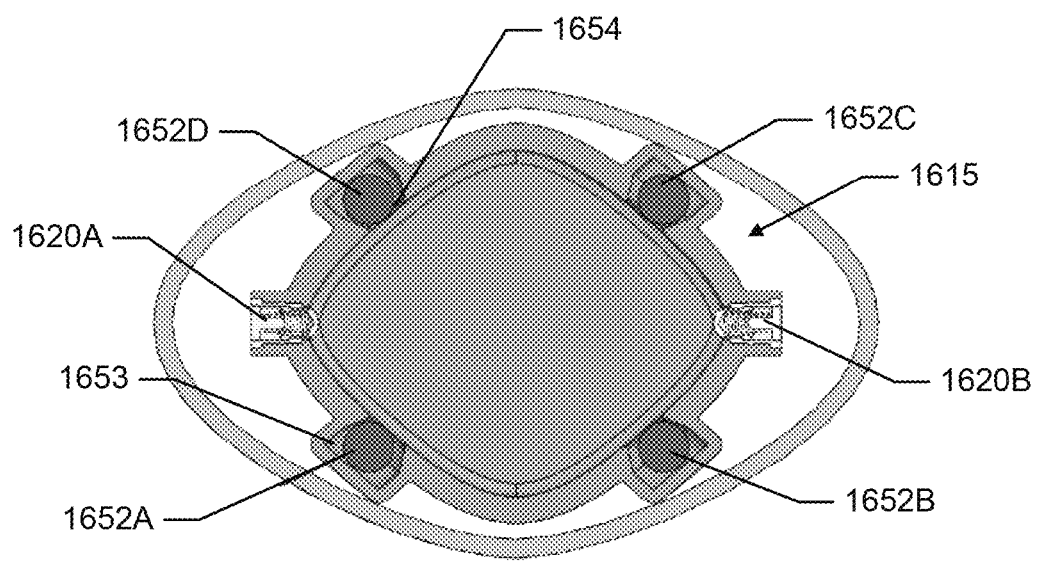
Figure 16C:
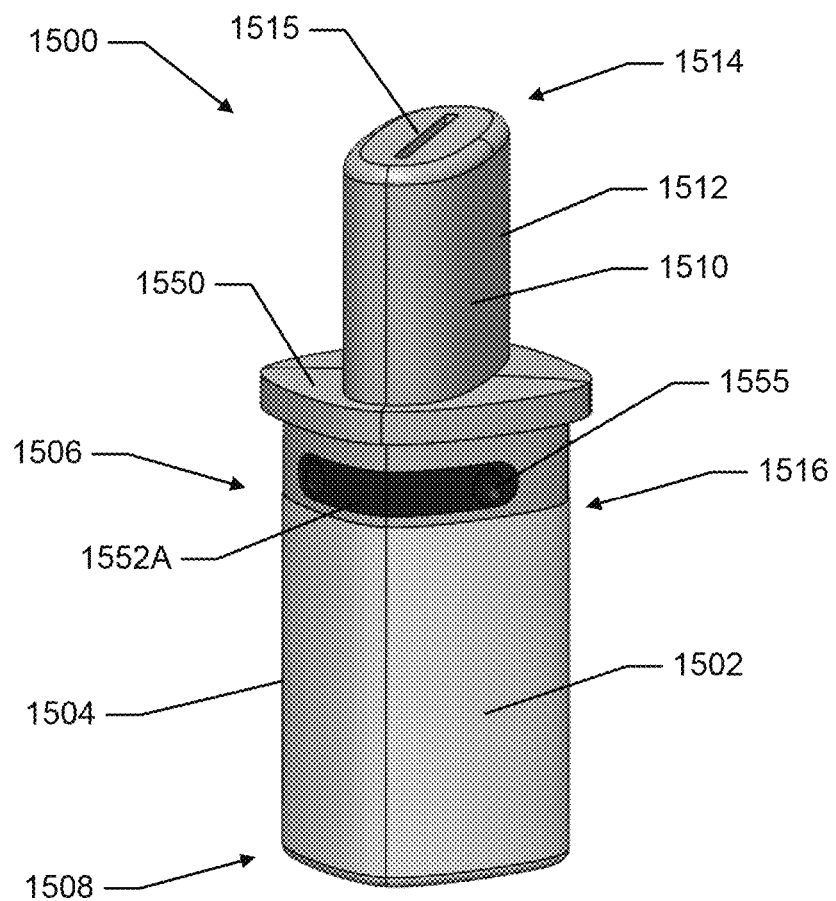
Figure 17:
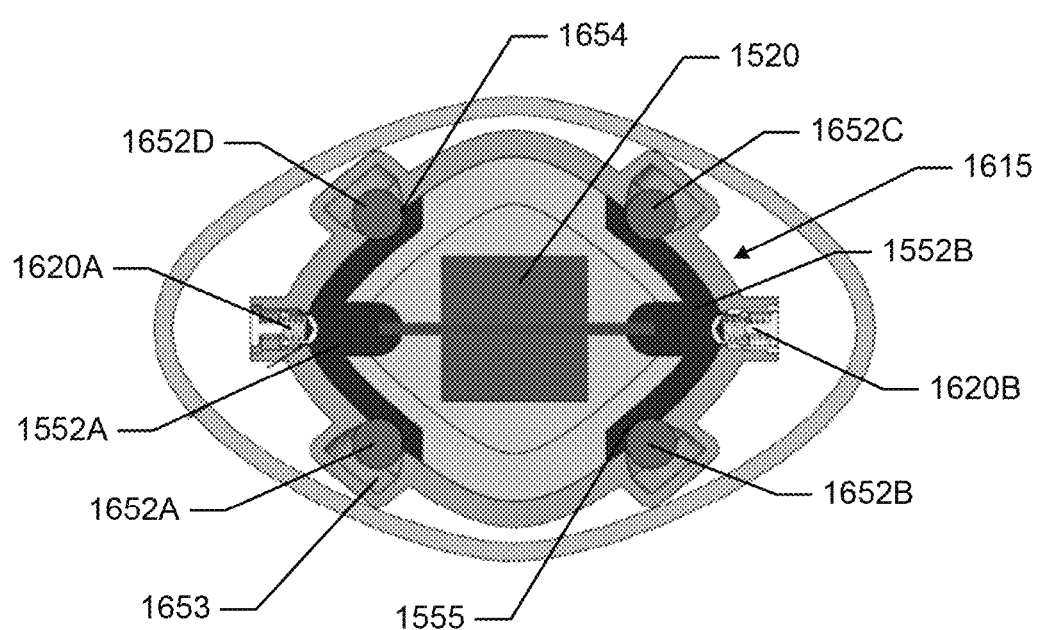
Figure 18A:
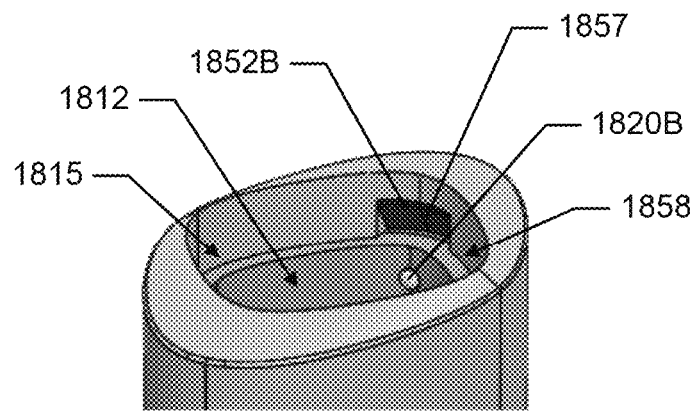
Figure 18B:
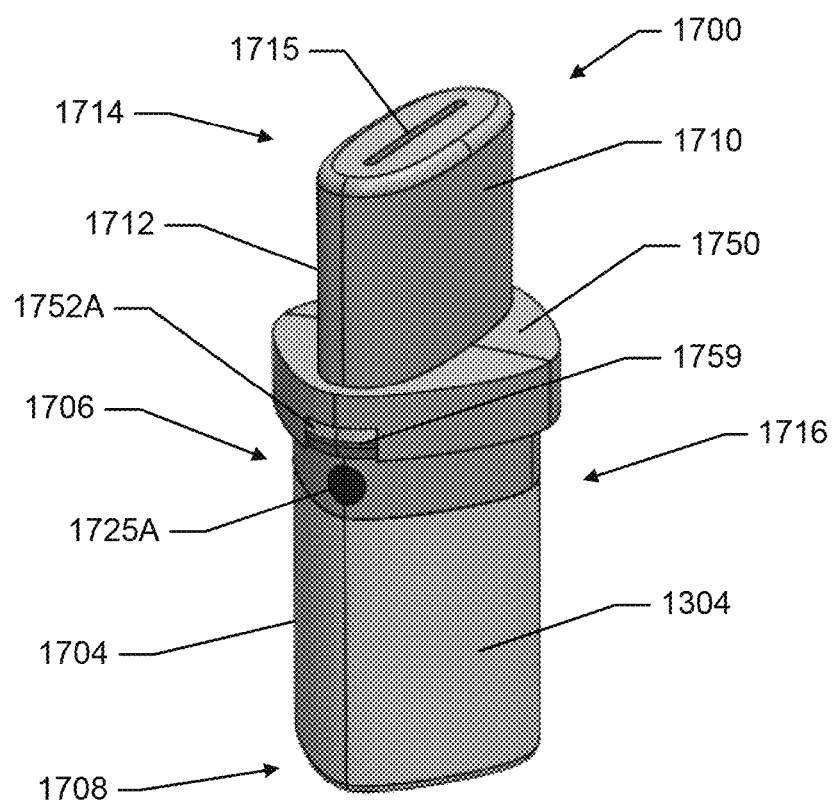
Figure 19A:
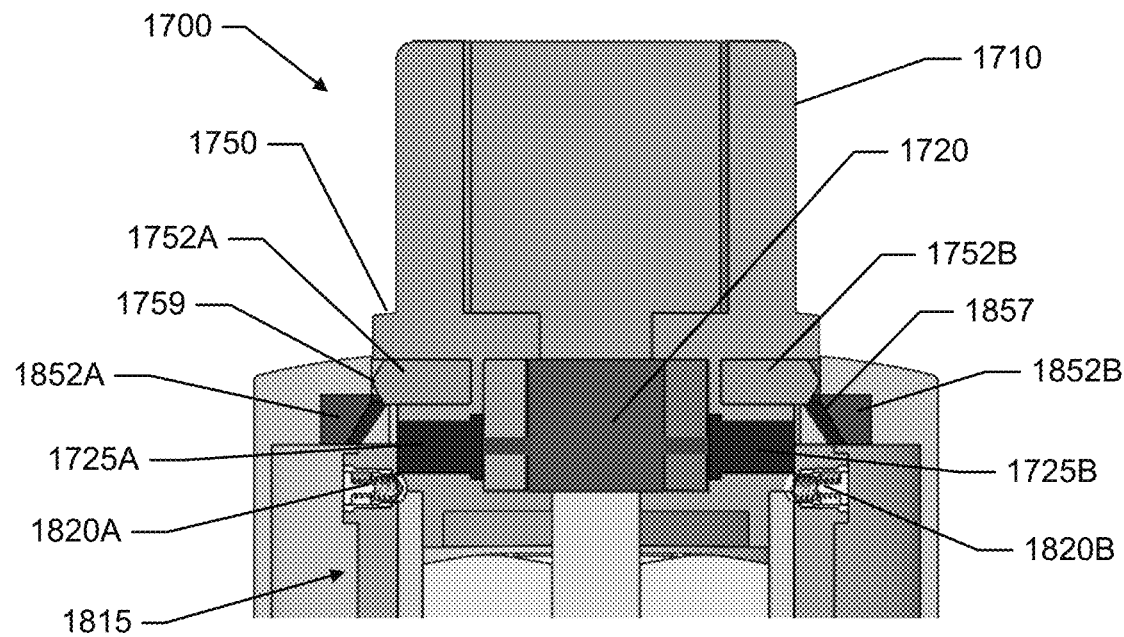
Figure 19B:
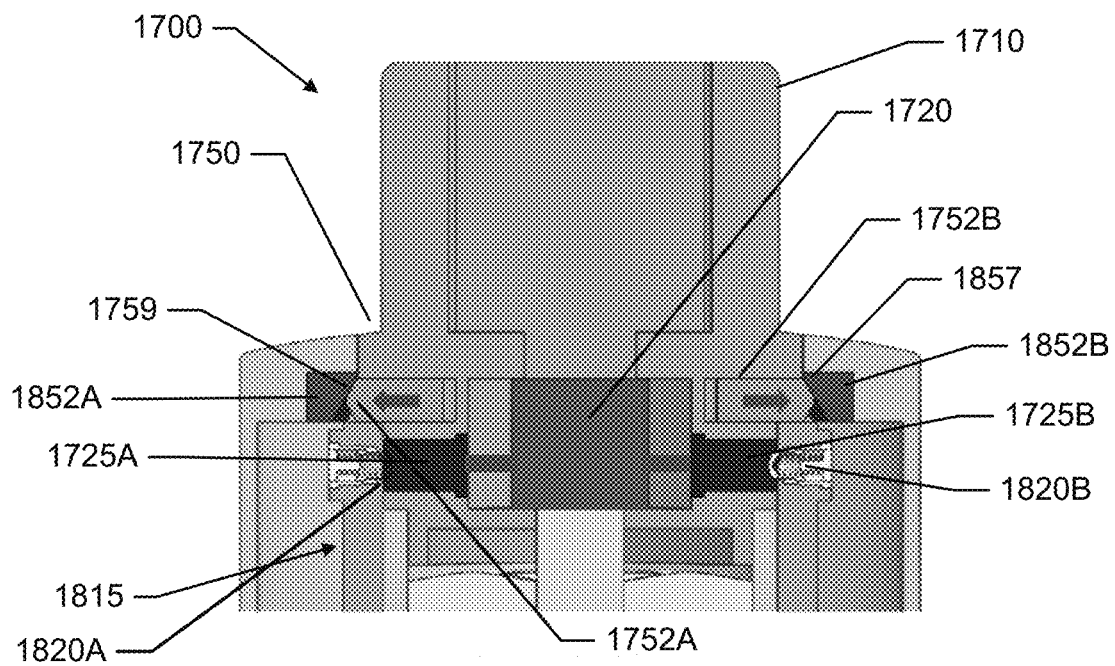
Figure 20A:
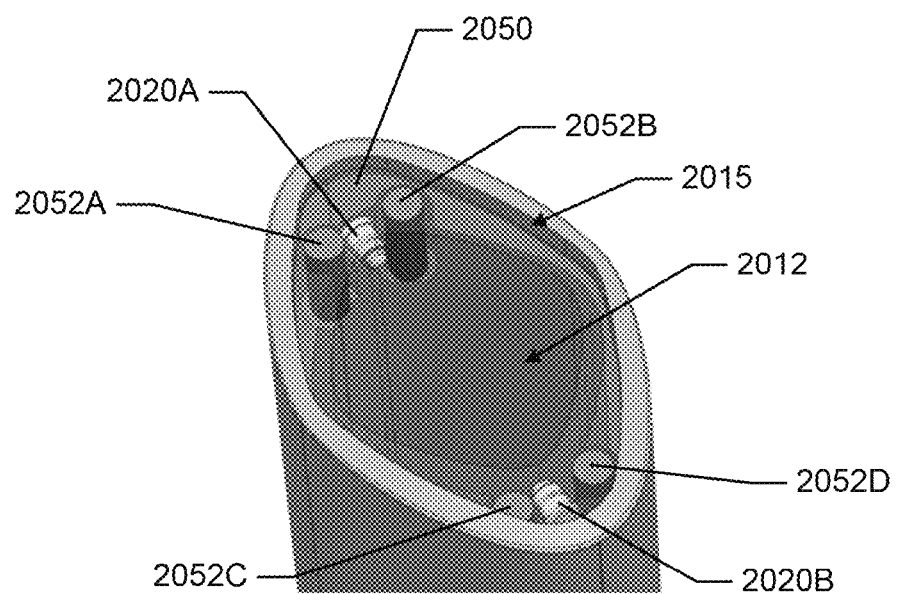
Figure 20B:
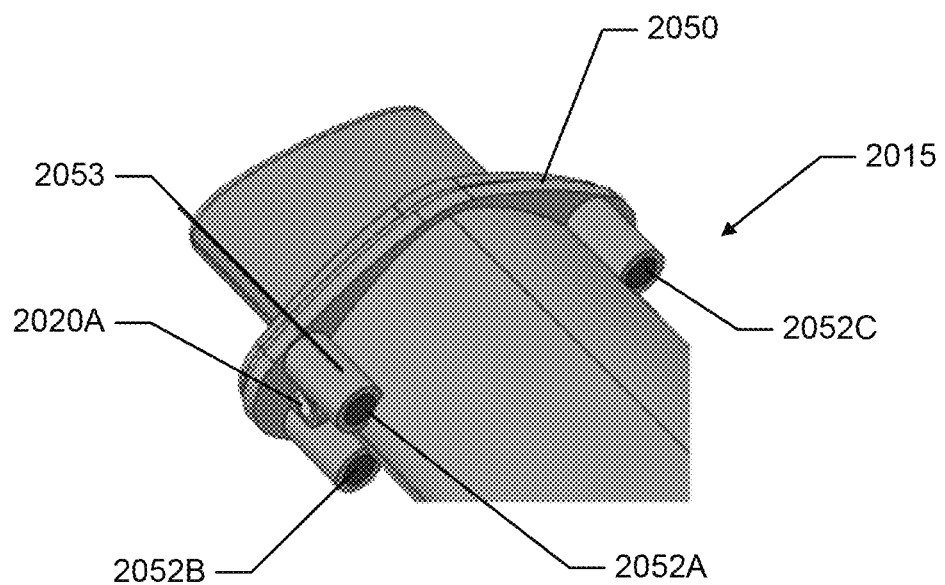
Figure 20C:
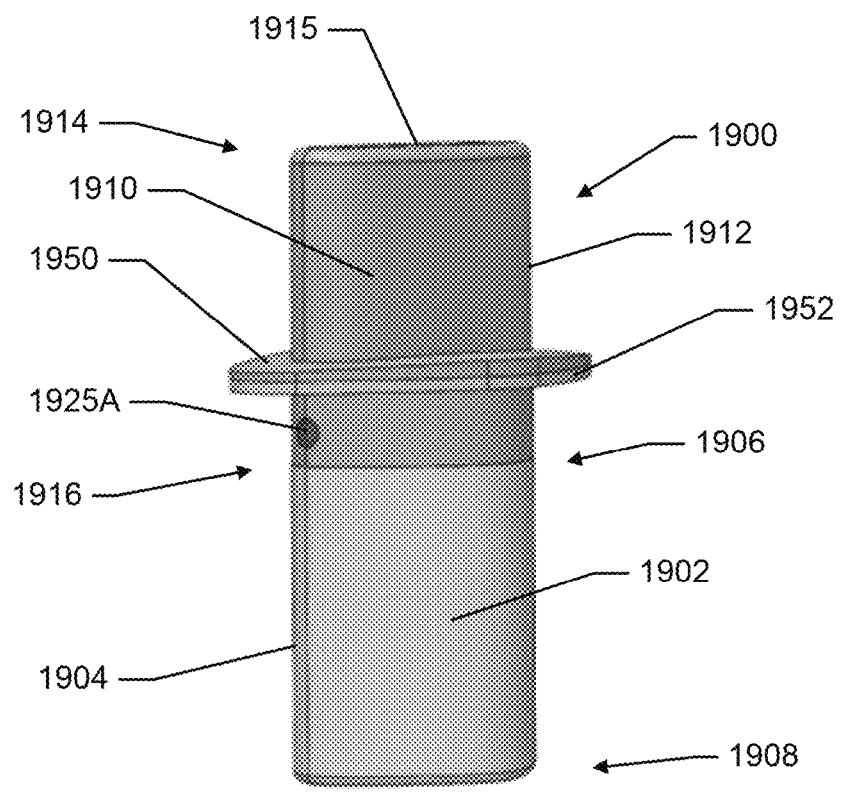
Figure 21:
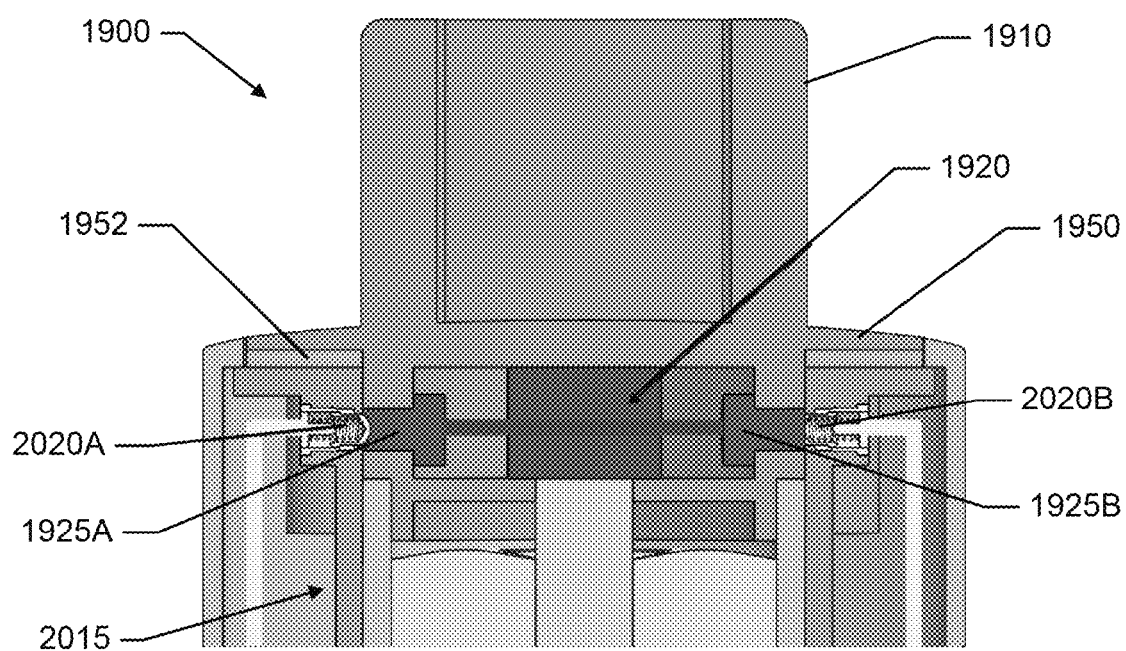
Figure 22A:
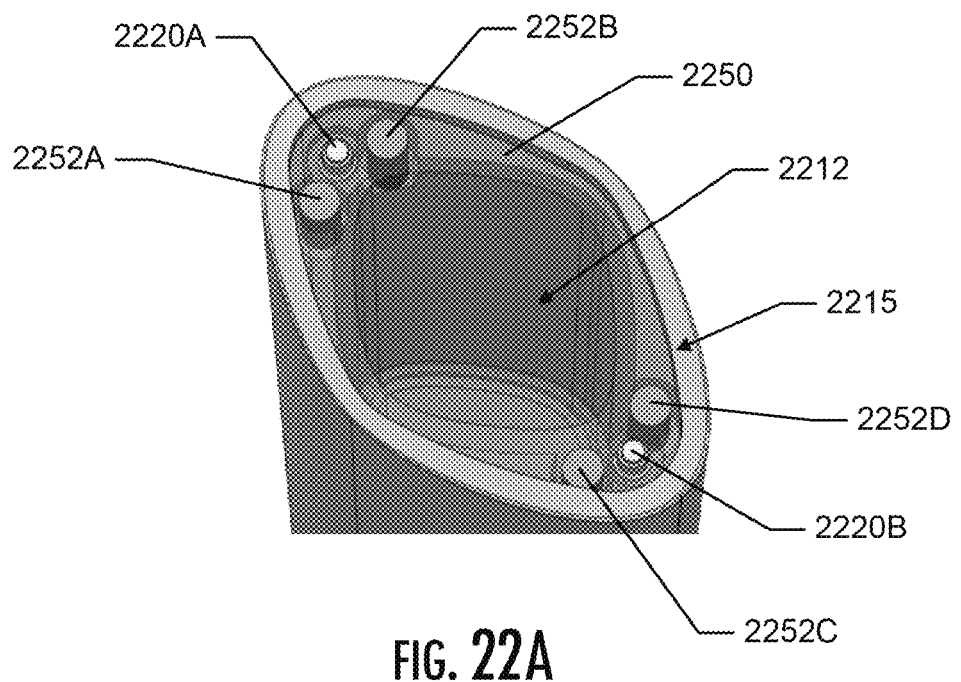
Figure 22B:
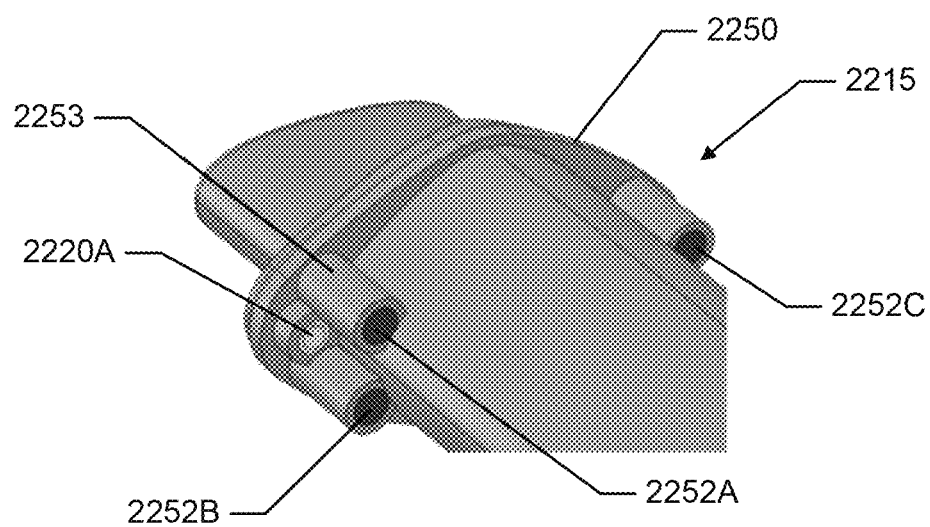
Figure 22C:
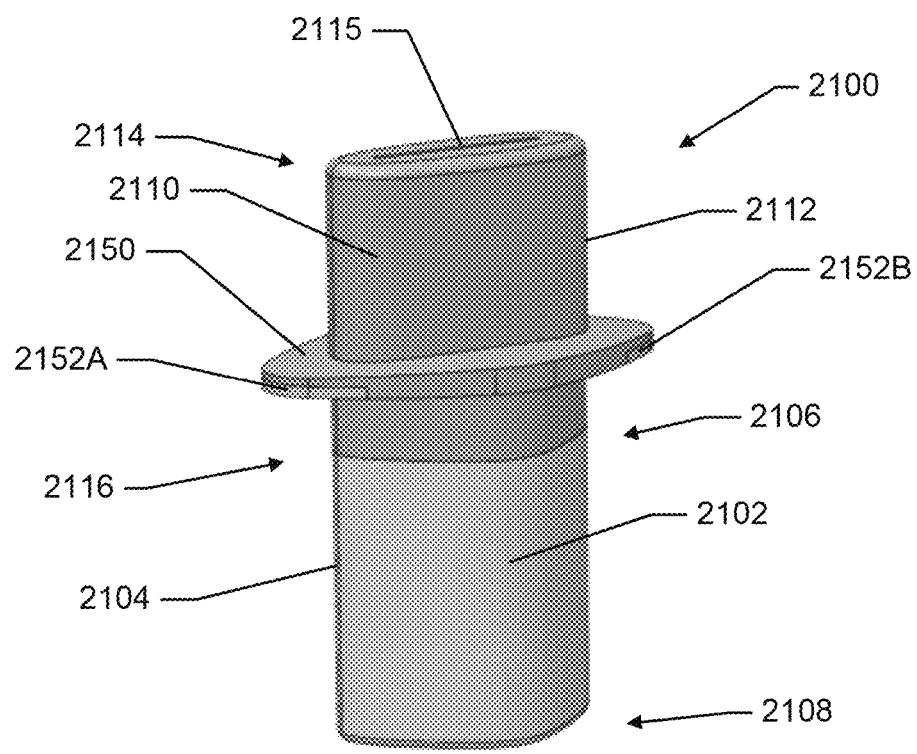
Figure 23:
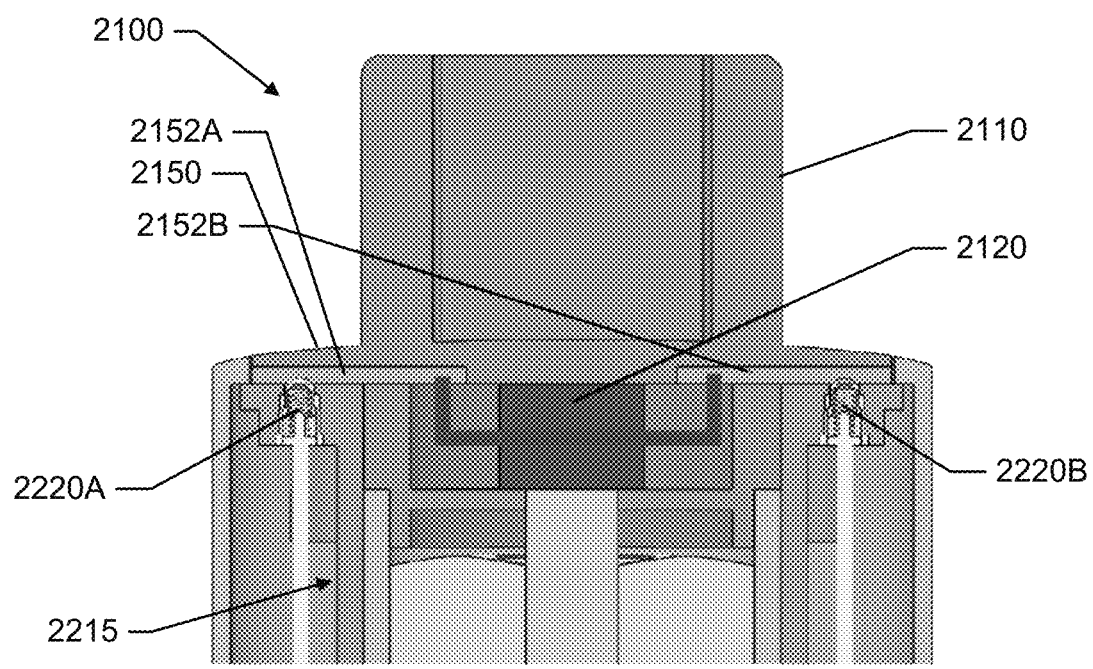
Figure 24A:
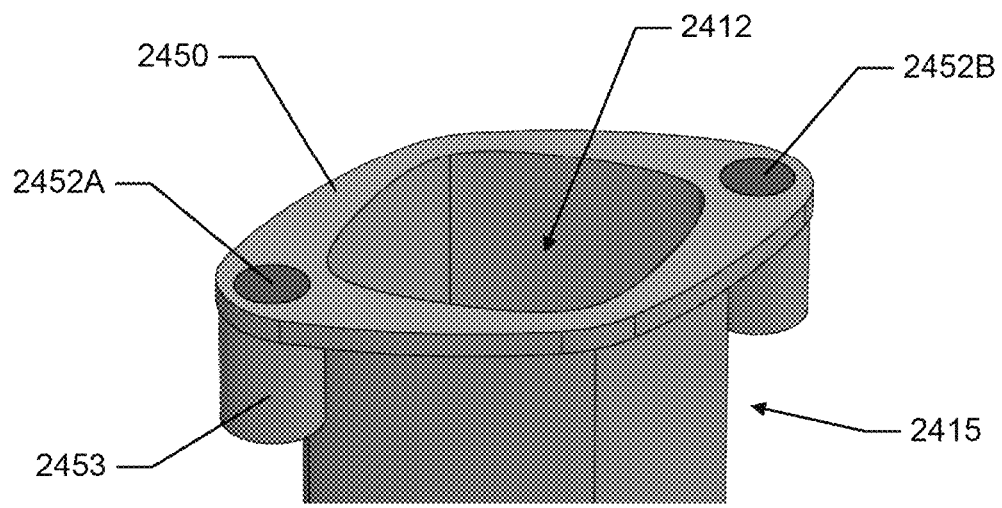
Figure 24B:
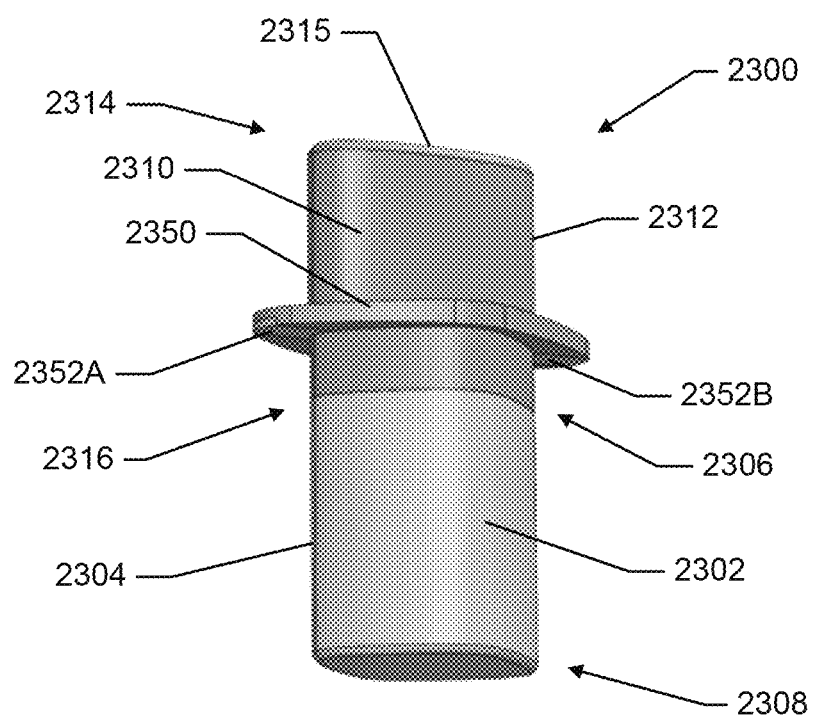
Figure 25:
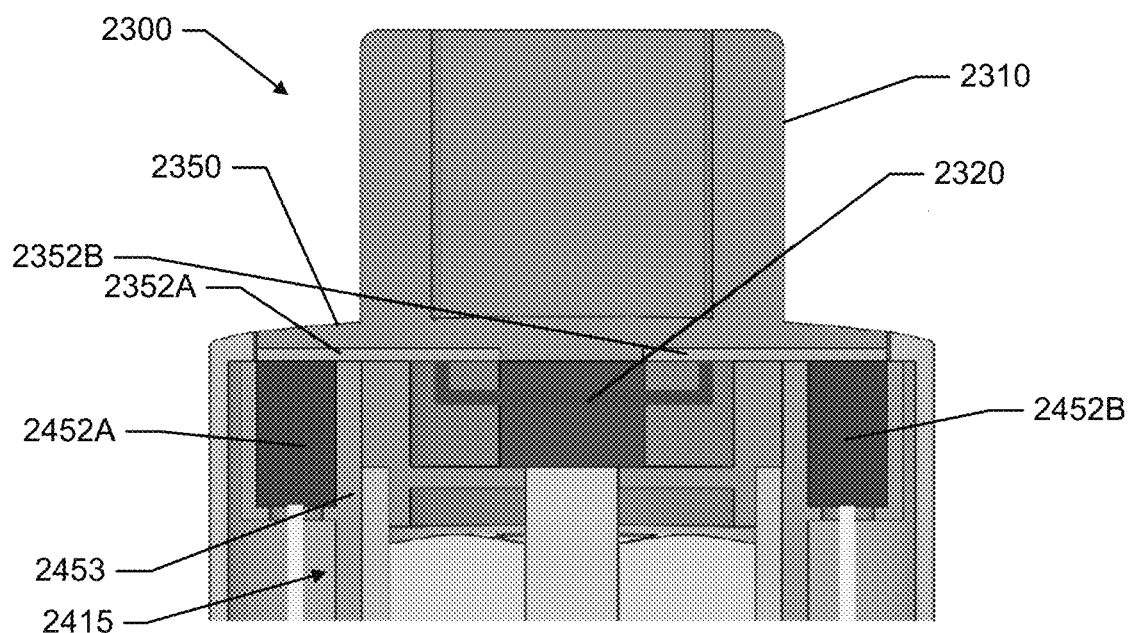
Figure 26A:
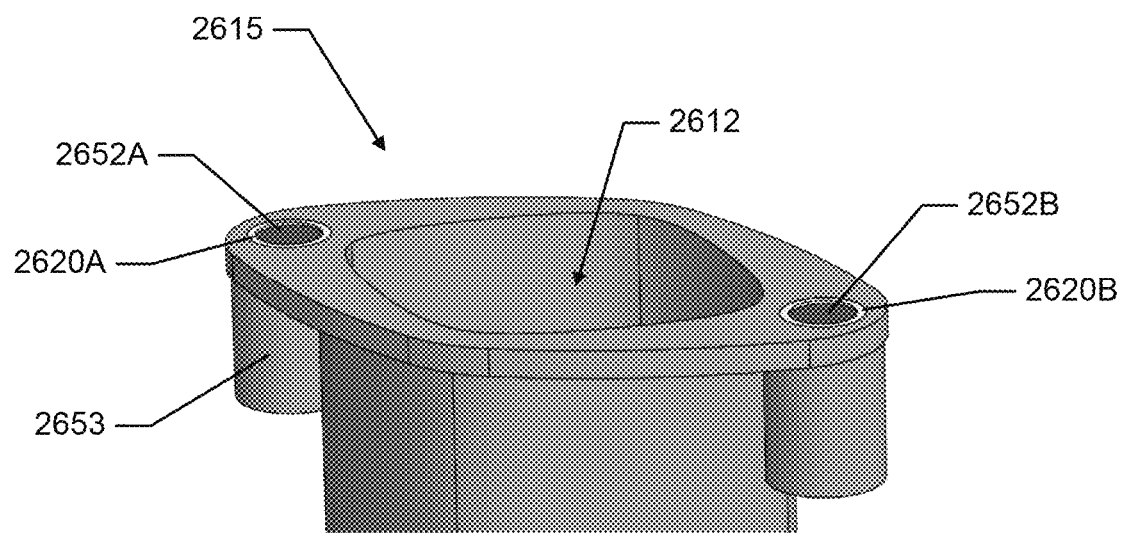
Figure 26B:
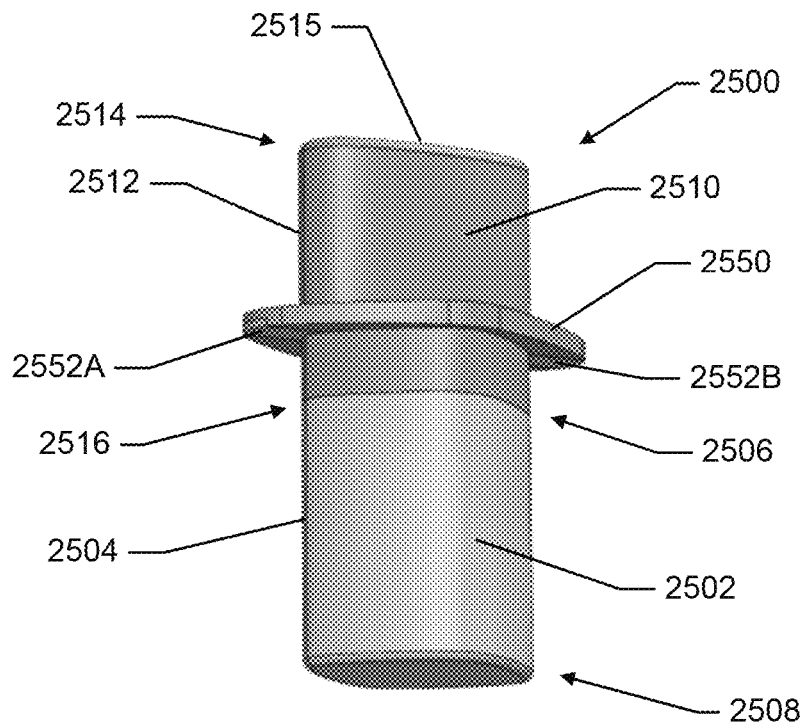
Figure 27:
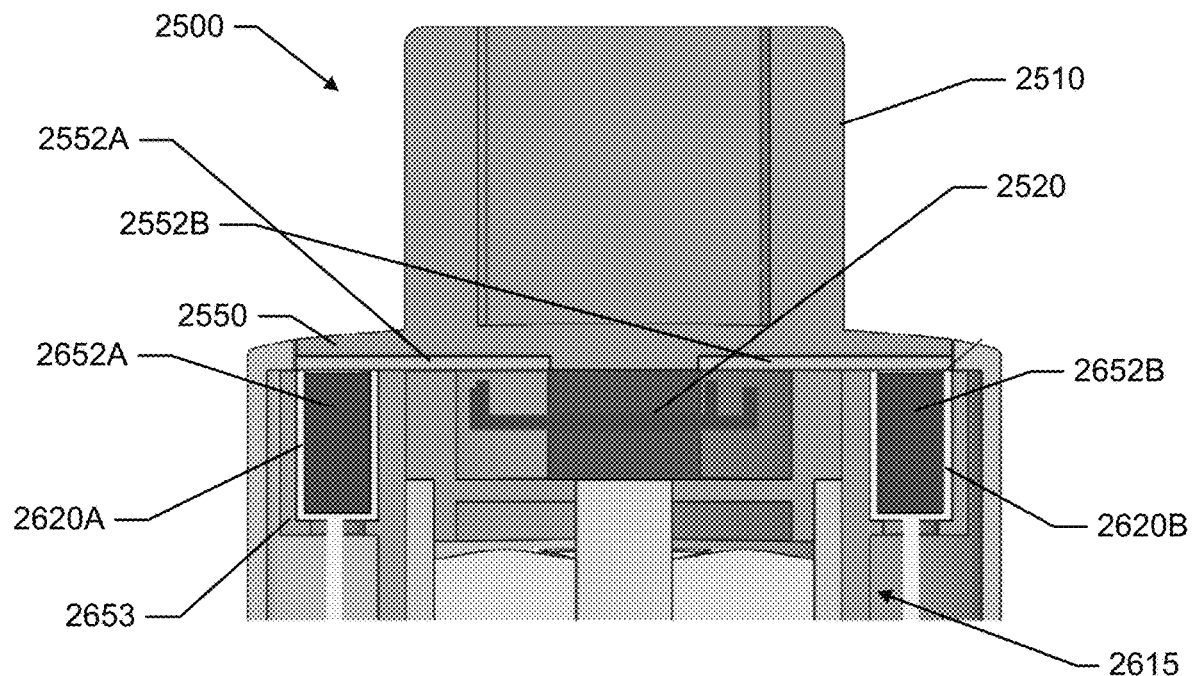
Figure 28A:
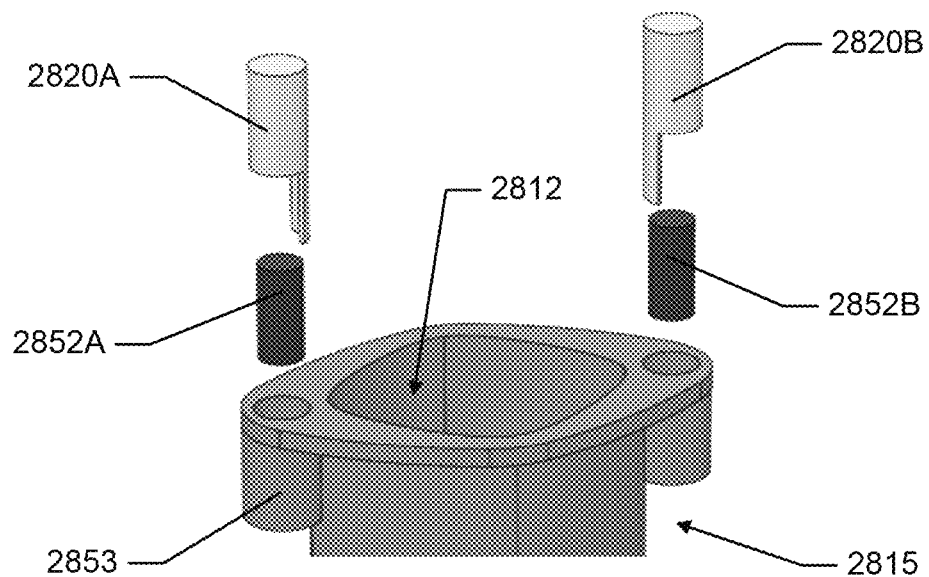
Figure 28B:
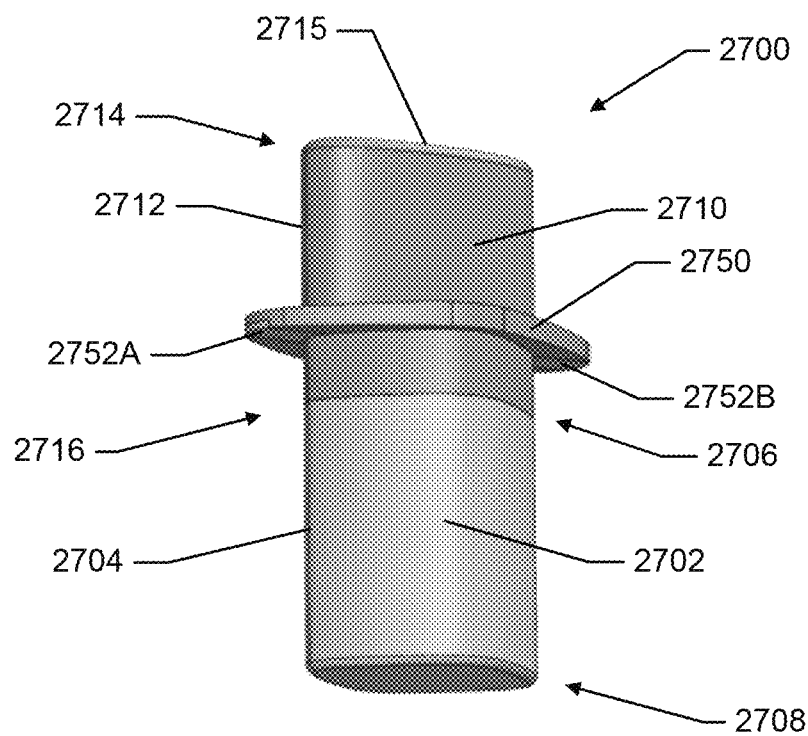
Figure 29:
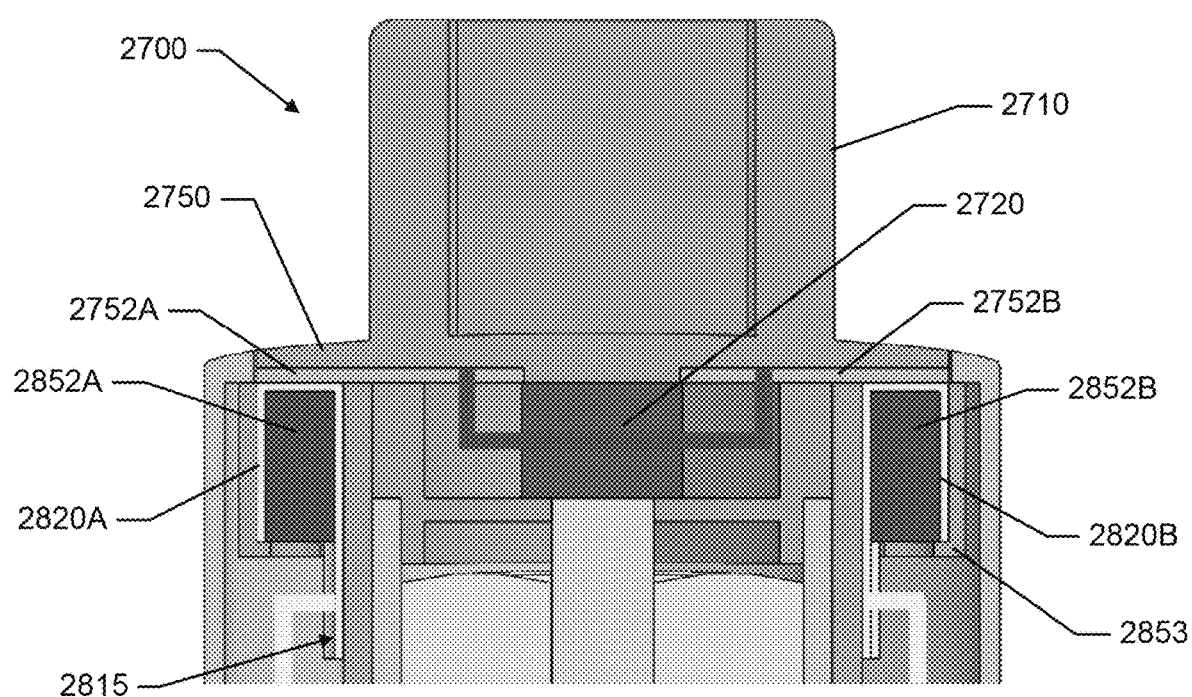
Figure 30A:
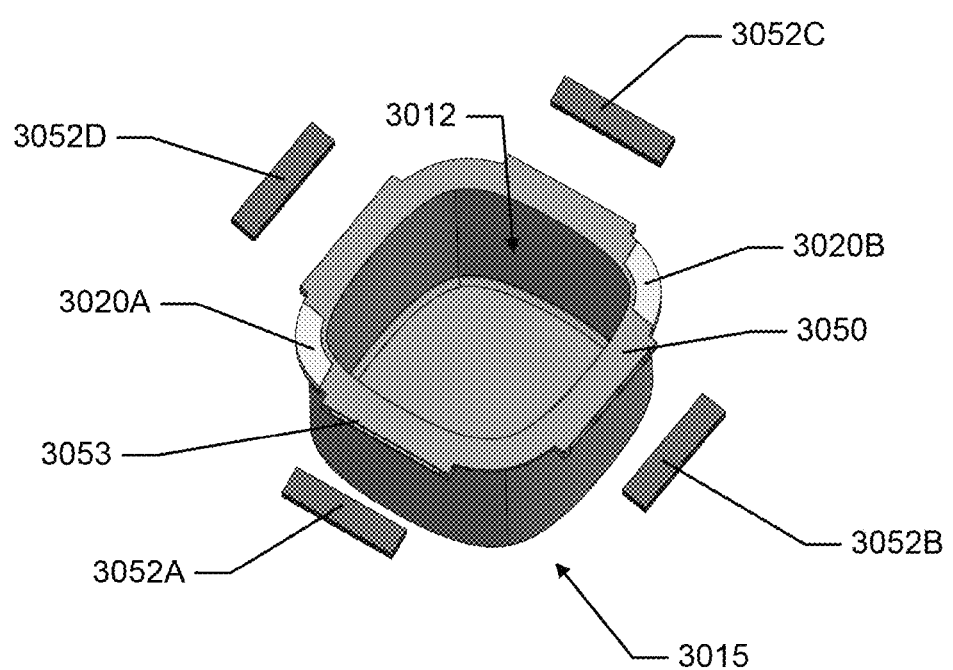
Figure 30B:
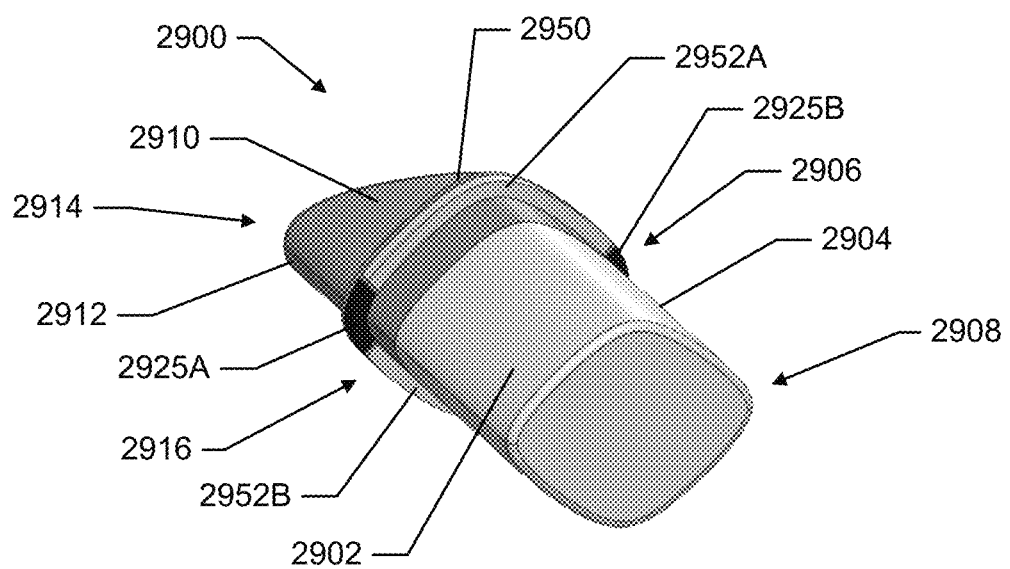
Figure 30C:
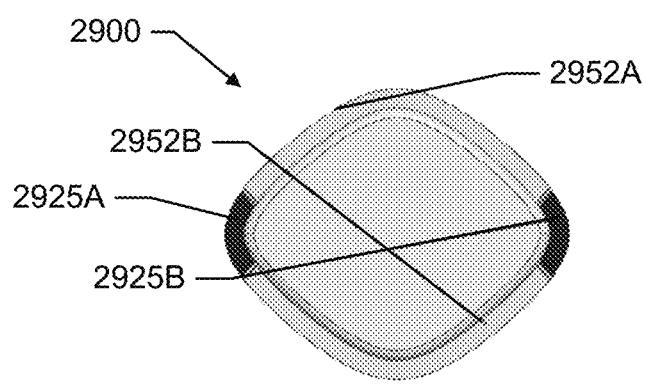
Figure 31:
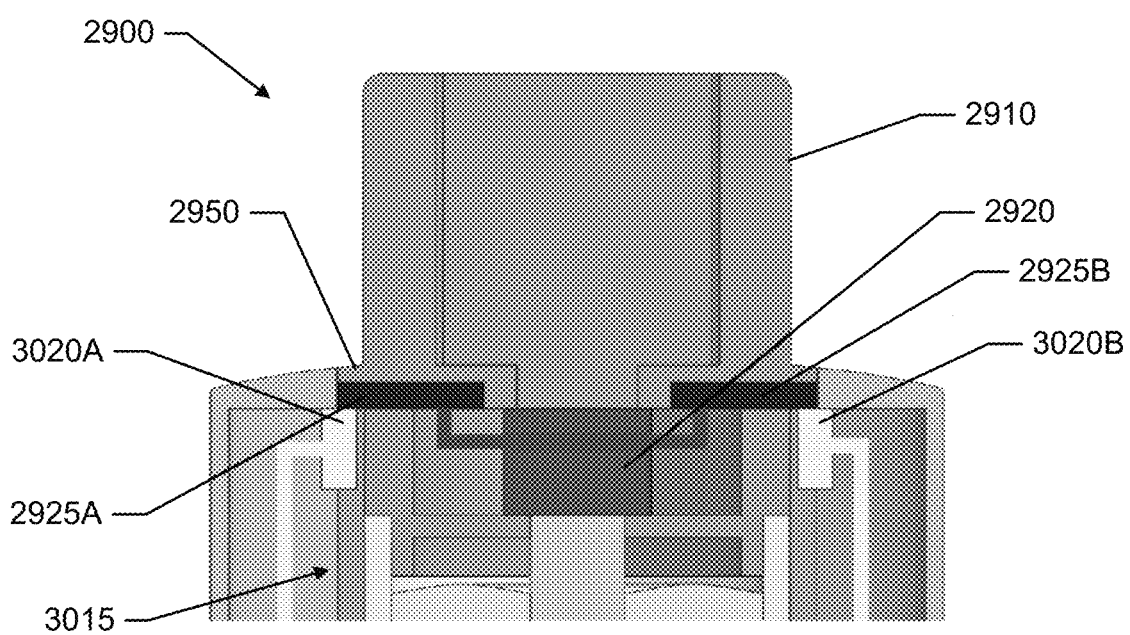
Figure 32A:
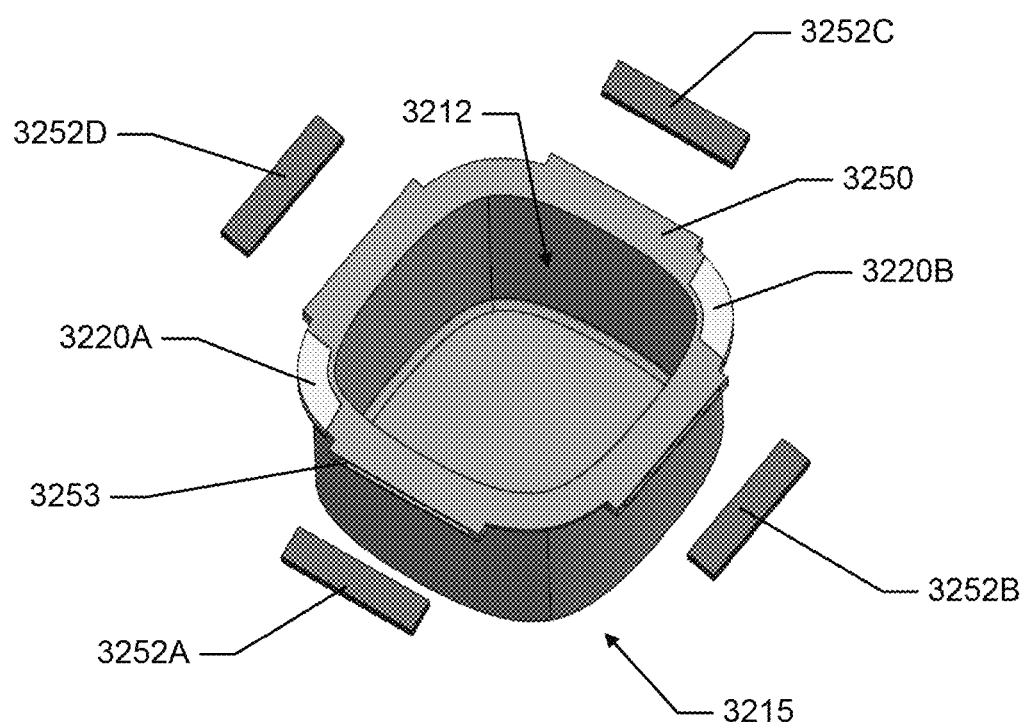
Figure 32B:
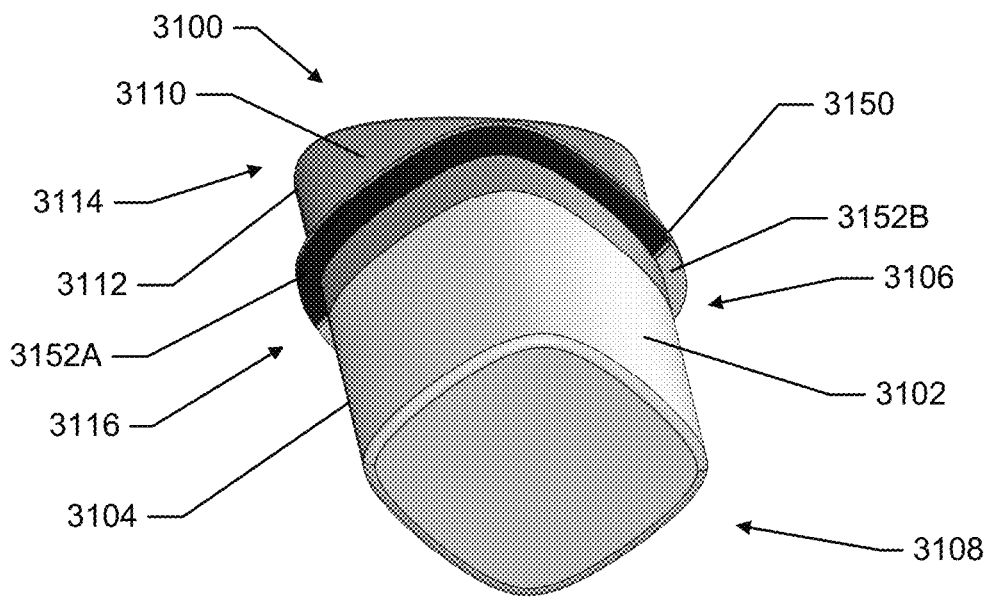
Figure 32C:
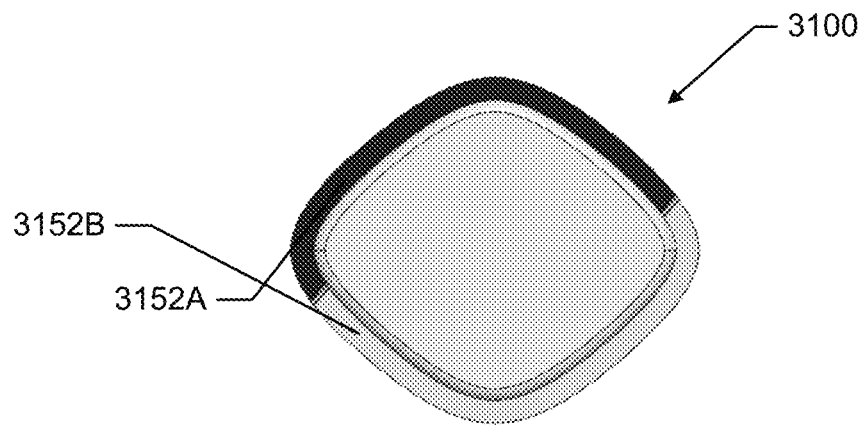
Figure 33:
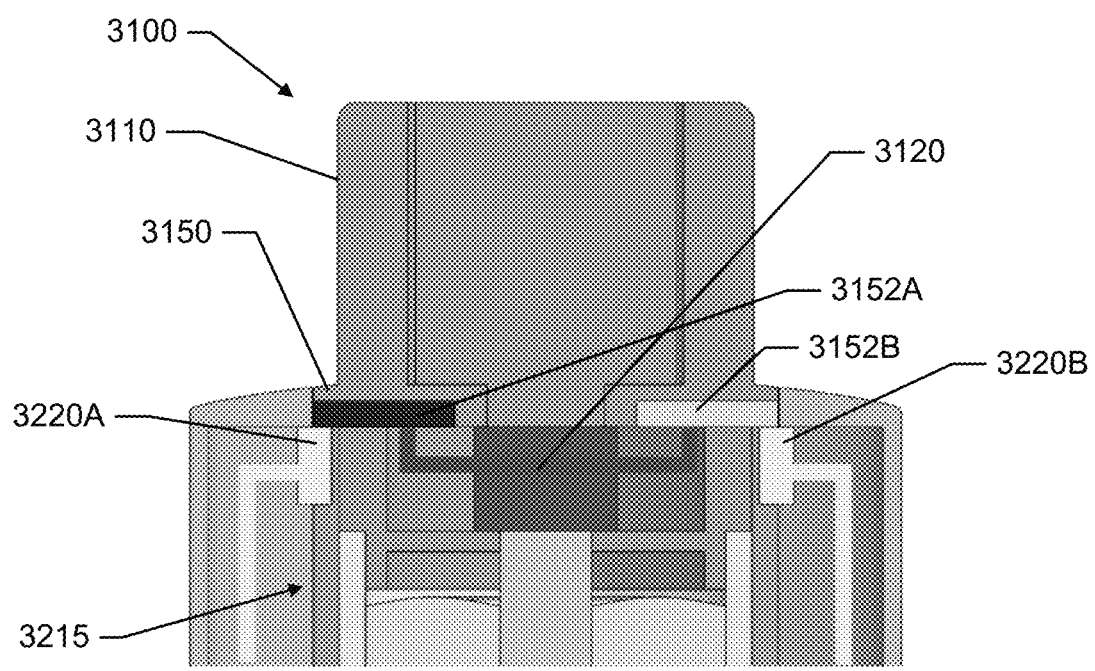
Figure 34:
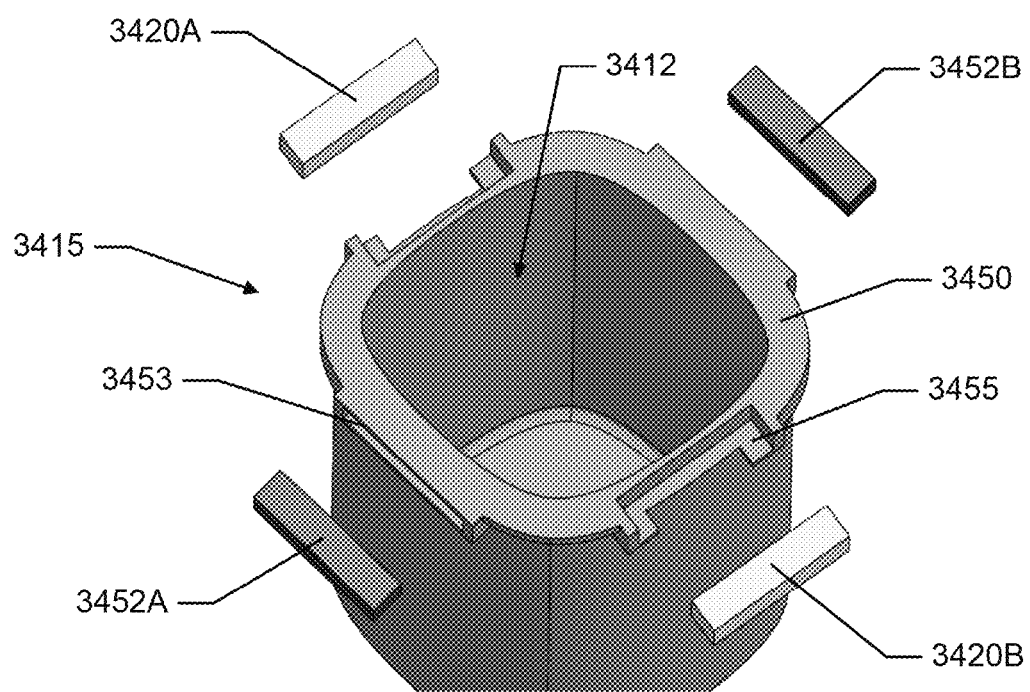
Figure 35:
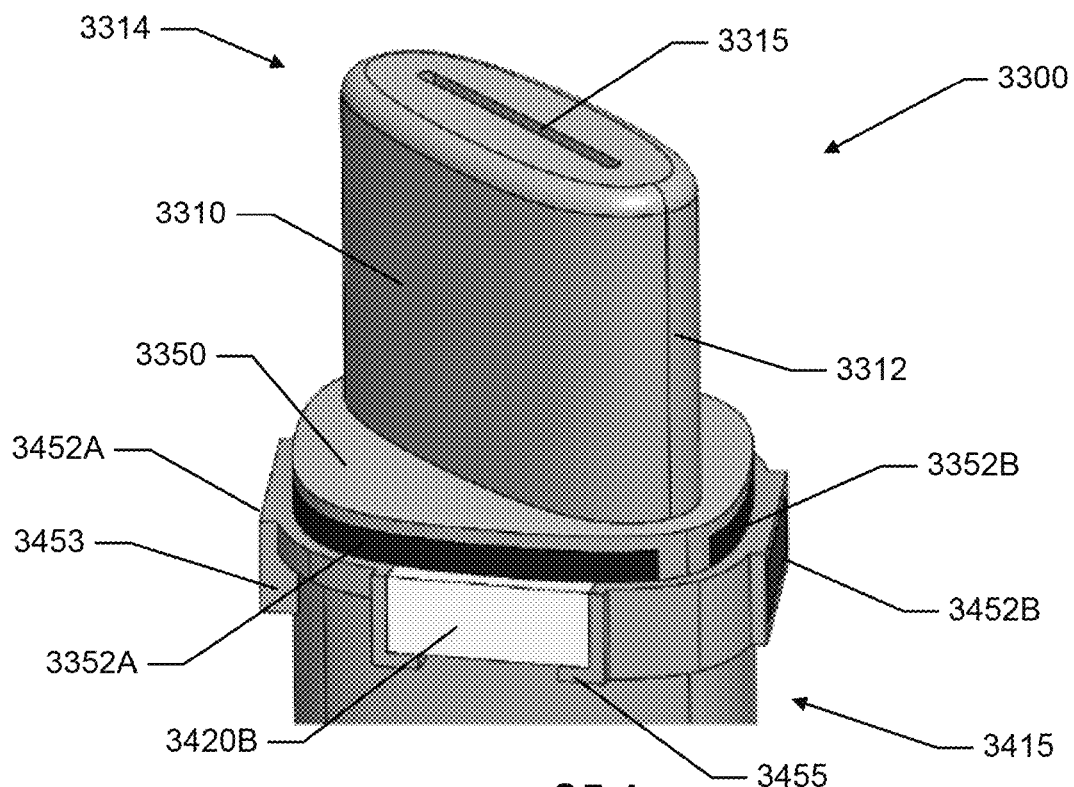
Figure 35:
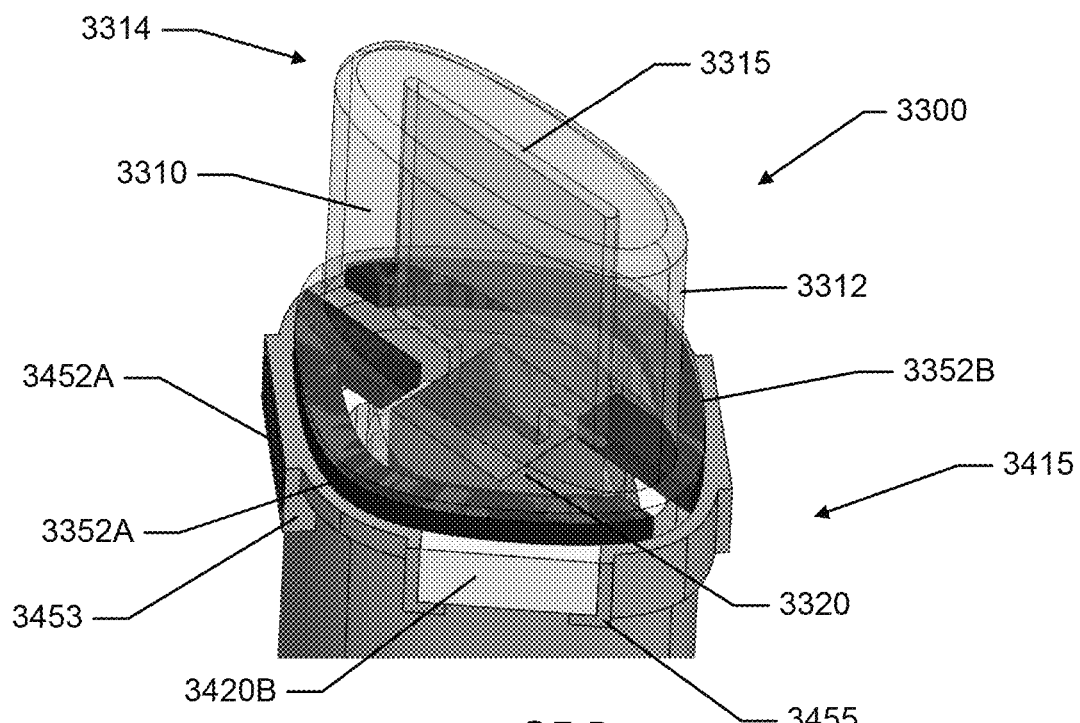
Figure 36A:
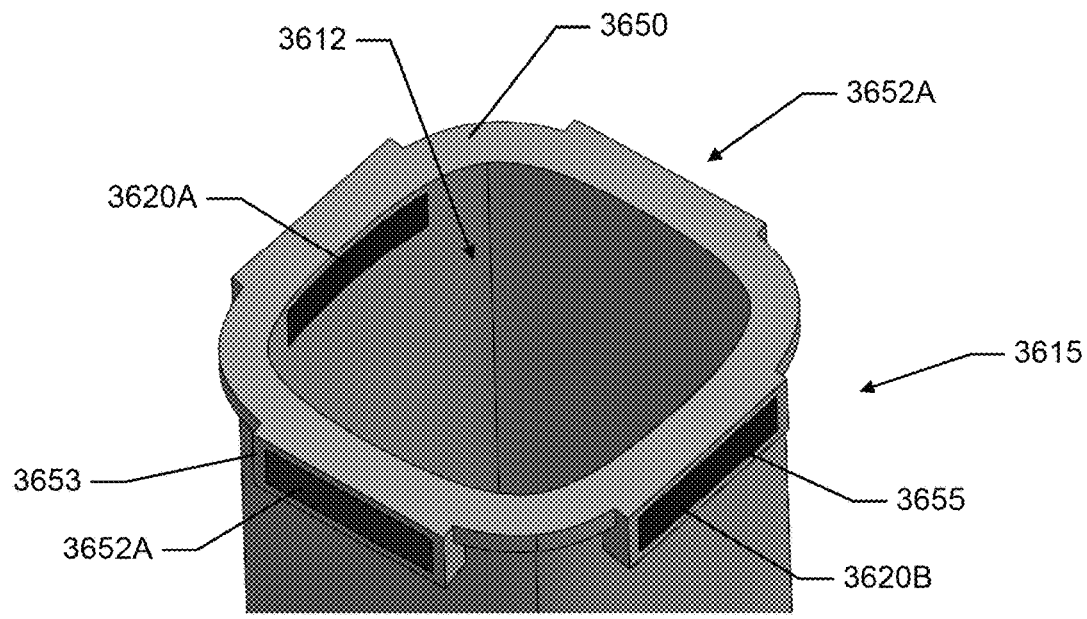
Figure 36B:
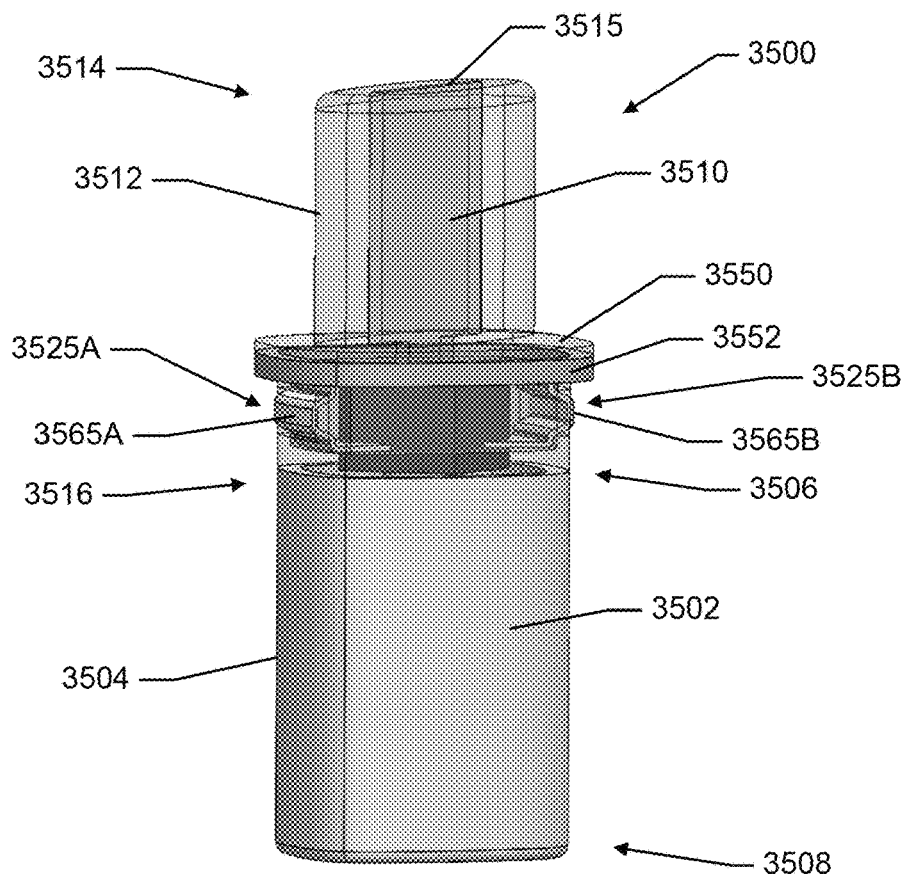
Figure 37:
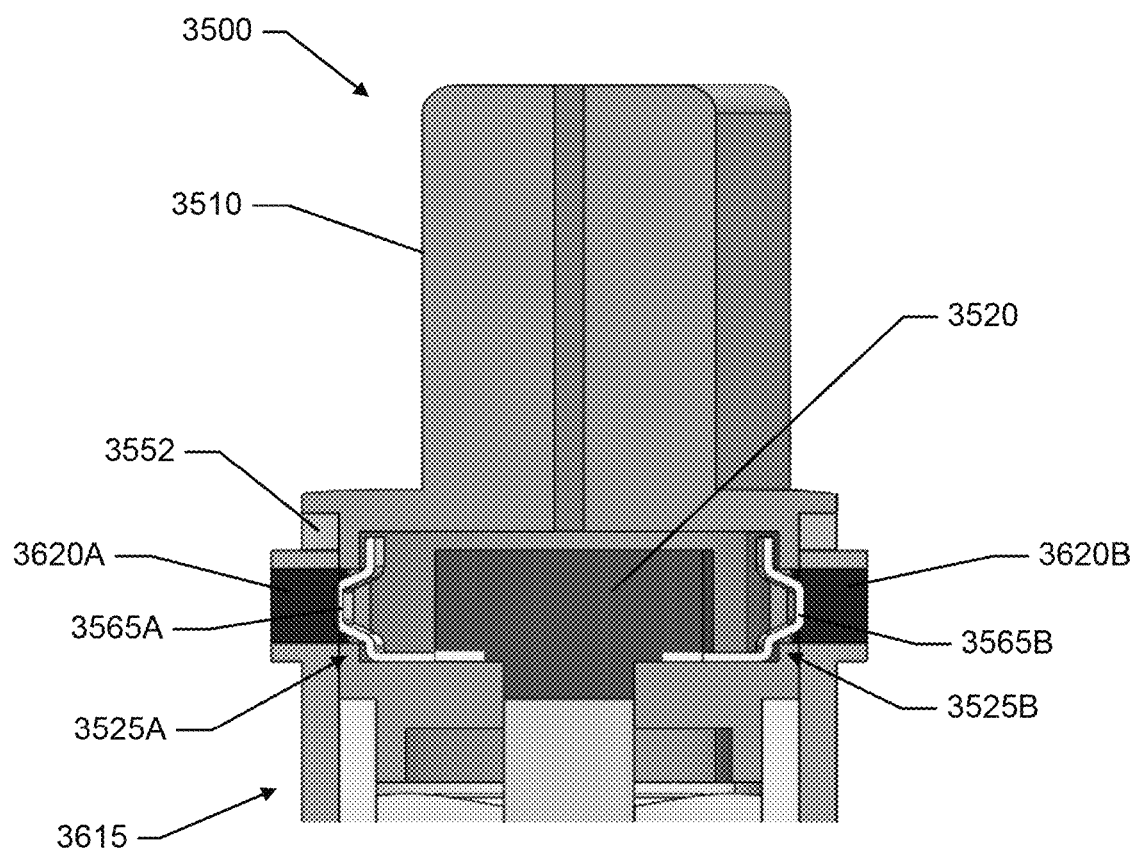
Figure 38A:
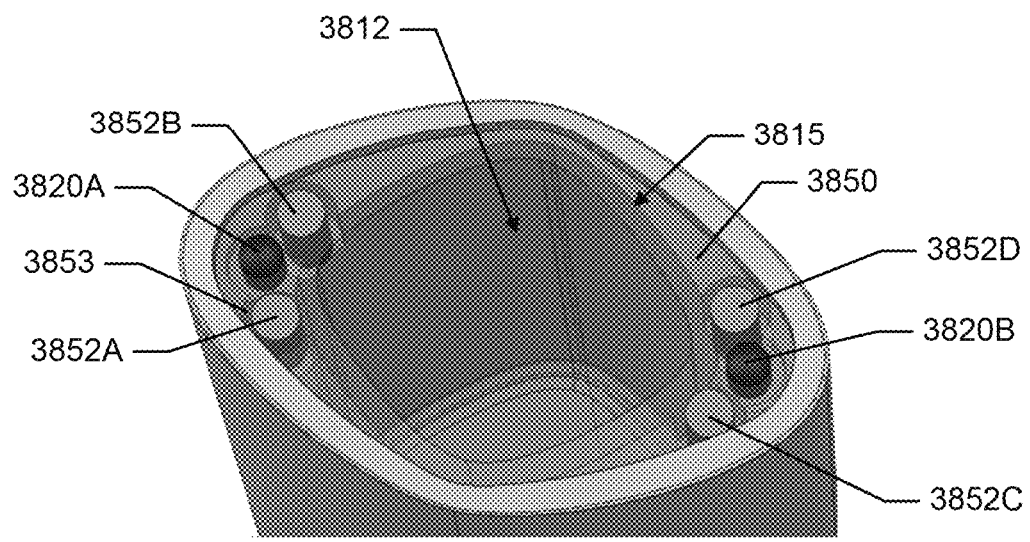
Figure 38B:
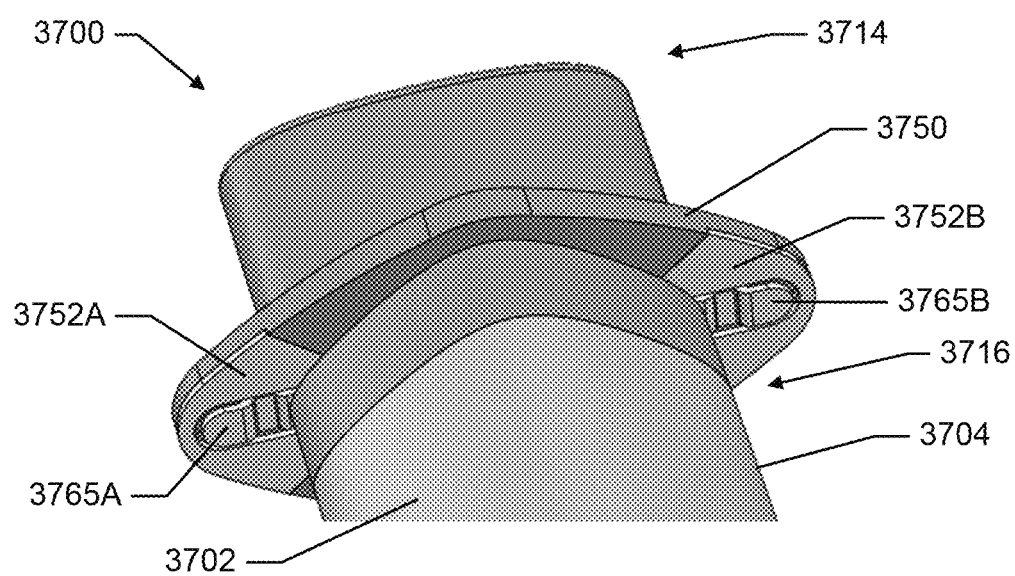
Figure 39:
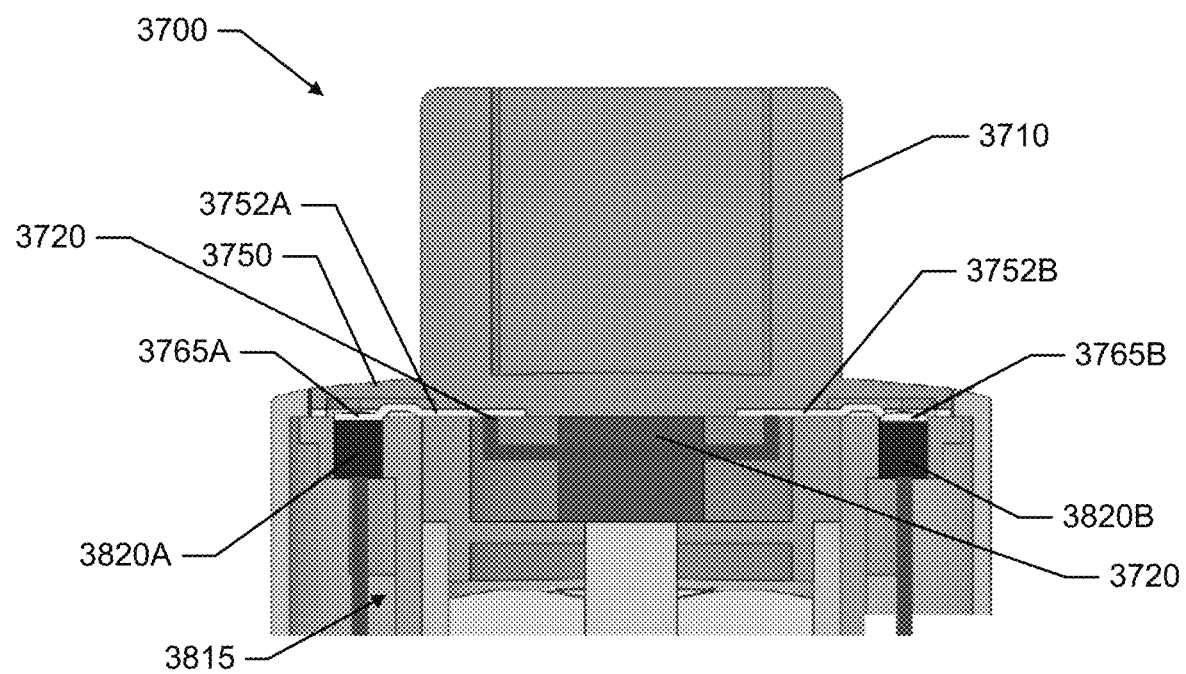
Figure 40:
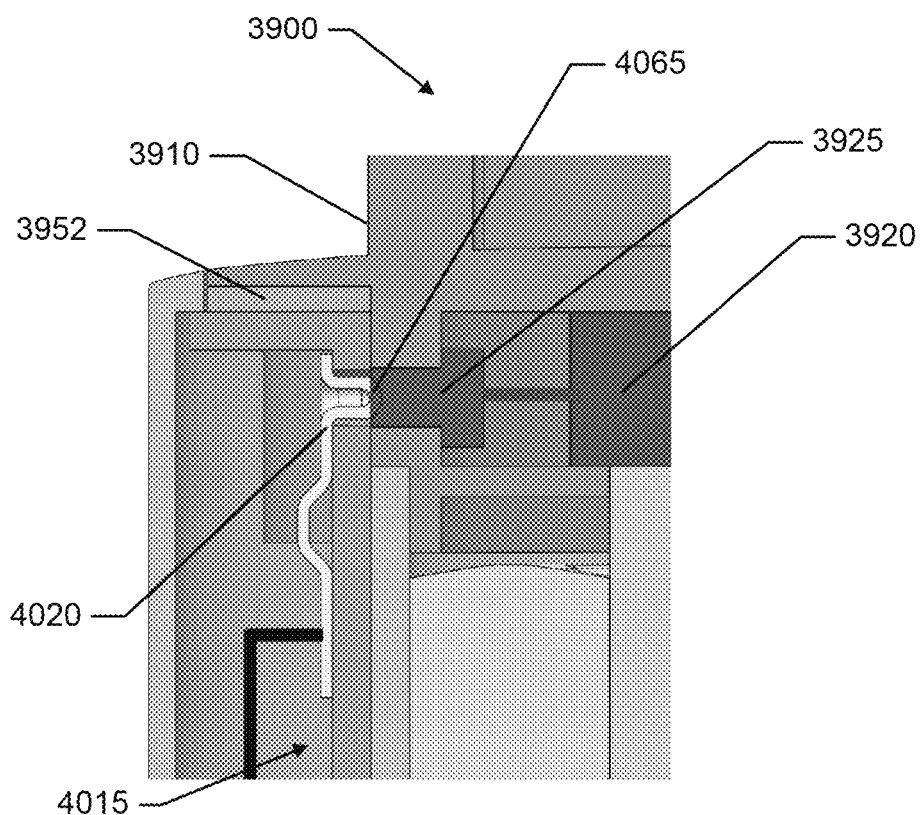

Having thus described the disclosure in the foregoing general terms, reference will now be made to the accompanying drawings, which are not necessarily drawn to scale, and wherein:

FIG. 1 illustrates a perspective view of an aerosol delivery device according to example implementations of the present disclosure;

FIG. 2 illustrates partial cross-section of the control device of the aerosol delivery device illustrated in FIG. 1;

FIG. 3A illustrates a perspective view of a cartridge according to example implementations of the present disclosure;

FIG. 3B illustrates a cross-section view of the cartridge of FIG. 3A according to an example implementation of the present disclosure;

FIG. 4A illustrates a partial perspective view of an inner frame of a control device according to an example implementation of the present disclosure;

FIG. 4B illustrates a perspective view of a cartridge according to an example implementation of the present disclosure;

FIG. 5 illustrates a partial cross-section view of a cartridge coupled with an inner frame of a control device according to an example implementation of the present disclosure;

FIG. 6 illustrates a partial perspective view of an inner frame of a control according to an example implementation of the present disclosure;

FIG. 7 illustrates a partial cross-section view of a cartridge coupled with an inner frame of a control device according to an example implementation of the present disclosure;

FIG. 8A illustrates a perspective view of an inner frame of a control device according to an example implementation of the present disclosure;

FIG. 8B illustrates a partial exploded top view of an inner frame of a control device according to an example implementation of the present disclosure;

FIG. 8C illustrates a perspective view of a cartridge according to an example implementation of the present disclosure;

FIG. 9 illustrates a partial cross-section view of a cartridge coupled with an inner frame of a control device according to an example implementation of the present disclosure;

FIG. 10A illustrates a perspective view of an inner frame of a control device according to an example implementation of the present disclosure;

FIG. 10B illustrates a partial exploded top view of a cartridge according to an example implementation of the present disclosure;

FIG. 10C illustrates a perspective view of a cartridge according to an example implementation of the present disclosure;

FIG. 11 illustrates a partial cross-section view of a cartridge coupled with an inner frame of a control device according to an example implementation of the present disclosure;

FIG. 12A illustrates an exploded partial perspective view of an inner frame of a control device according to an example implementation of the present disclosure;

FIG. 12B illustrates a perspective view of a cartridge according to an example implementation of the present disclosure;

FIG. 13 illustrates a partial cross-section view of a cartridge coupled with an inner frame of a control device according to an example implementation of the present disclosure;

FIG. 14A illustrates a partial perspective view of an inner frame of a control device according to an example implementation of the present disclosure;

FIG. 14B illustrates a perspective view of a cartridge according to an example implementation of the present disclosure;

FIG. 14C illustrates a partial transparent perspective view of a cartridge according to an example implementation of the present disclosure;

FIG. 15 illustrates a partial cross-section view of a cartridge coupled with an inner frame of a control device according to an example implementation of the present disclosure;

FIG. 16A illustrates a partial perspective view of an inner frame of a control device according to an example implementation of the present disclosure;

FIG. 16B illustrates a top view of an inner frame of a control device according to an example implementation of the present disclosure;

FIG. 16C illustrates a perspective view of a cartridge according to an example implementation of the present disclosure;

FIG. 17 illustrates a partial cross-section view of a cartridge coupled with an inner frame of a control device according to an example implementation of the present disclosure;

FIG. 18A illustrates a partial perspective view of an inner frame of a control device according to an example implementation of the present disclosure;

FIG. 18B illustrates a perspective view of a cartridge according to an example implementation of the present disclosure;

FIG. 19A illustrates a partial cross-section view of a cartridge prior to being fully coupled with an inner frame of a control device according to an example implementation of the present disclosure;

FIG. 19B illustrates a partial cross-section view of a cartridge coupled with an inner frame of a control device according to an example implementation of the present disclosure;

FIG. 20A illustrates a partial transparent perspective view of an inner frame of a control device according to an example implementation of the present disclosure;

FIG. 20B illustrates a partial perspective view of a cartridge coupled with an inner frame of a control device according to an example implementation of the present disclosure;

FIG. 20C illustrates a perspective view of a cartridge according to an example implementation of the present disclosure;

FIG. 21 illustrates a partial cross-section view of a cartridge coupled with an inner frame of a control device according to an example implementation of the present disclosure;

FIG. 22A illustrates a partial perspective view of an inner frame of a control device according to an example implementation of the present disclosure;

FIG. 22B illustrates a partial perspective view of cartridge coupled with an inner frame of a control device according to an example implementation of the present disclosure;

FIG. 22C illustrates a perspective view of a cartridge according to an example implementation of the present disclosure;

FIG. 23 illustrates a partial cross-section view of a cartridge coupled with an inner frame of a control device according to an example implementation of the present disclosure;

FIG. 24A illustrates a partial perspective view of an inner frame of a control device according to an example implementation of the present disclosure;

FIG. 24B illustrates a perspective view of a cartridge according to an example implementation of the present disclosure;

FIG. 25 illustrates a partial cross-section view of a cartridge coupled with an inner frame of a control device according to an example implementation of the present disclosure;

FIG. 26A illustrates a partial perspective view of an inner frame of a control device according to an example implementation of the present disclosure;

FIG. 26B illustrates a perspective view of a cartridge according to an example implementation of the present disclosure;

FIG. 27 illustrates a partial cross-section view of a cartridge coupled with an inner frame of a control device according to an example implementation of the present disclosure;

FIG. 28A illustrates an exploded partial perspective view of an inner frame of a control device according to an example implementation of the present disclosure;

FIG. 28B illustrates a perspective view of a cartridge according to an example implementation of the present disclosure;

FIG. 29 illustrates a partial cross-section view of a cartridge coupled with an inner frame of a control device according to an example implementation of the present disclosure;

FIG. 30A illustrates a partial exploded perspective view of an inner frame of a control device according to an example implementation of the present disclosure;

FIG. 30B illustrates a perspective view of a cartridge according to an example implementation of the present disclosure;

FIG. 30C illustrates a bottom view of a cartridge according to an example implementation of the present disclosure;

FIG. 31 illustrates a partial cross-section view of a cartridge coupled with an inner frame of a control device according to an example implementation of the present disclosure;

FIG. 32A illustrates a partial exploded perspective view of an inner frame of a control device according to an example implementation of the present disclosure;

FIG. 32B illustrates a perspective view of a cartridge according to an example implementation of the present disclosure;

FIG. 32C illustrates a bottom view of a cartridge according to an example implementation of the present disclosure;

FIG. 33 illustrates a partial cross-section view of a cartridge coupled with an inner frame of a control device according to an example implementation of the present disclosure;

FIG. 34 illustrates a partial exploded perspective view of an inner frame of a control device according to an example implementation of the present disclosure;

FIG. 35A illustrates a partial perspective view of a cartridge coupled with an inner frame of a control device according to an example implementation of the present disclosure;

FIG. 35B illustrates a partial transparent perspective view of a cartridge coupled with an inner frame of a control device according to an example implementation of the present disclosure;

FIG. 36A illustrates a partial perspective view of an inner frame of a control device according to an example implementation of the present disclosure;

FIG. 36B illustrates a partial transparent perspective view of a cartridge according to an example implementation of the present disclosure;

FIG. 37 illustrates a partial cross-section view of a cartridge coupled with an inner frame of a control device according to an example implementation of the present disclosure;

FIG. 38A illustrates a partial transparent perspective view of an inner frame of a control device according to an example implementation of the present disclosure;

FIG. 38B illustrates a partial perspective view of a cartridge according to an example implementation of the present disclosure;

FIG. 39 illustrates a partial cross-section view of a cartridge coupled with an inner frame of a control device according to an example implementation of the present disclosure; and FIG. 40 illustrates a partial cross-section view of a cartridge coupled with an inner frame of a control device according to an example implementation of the present disclosure.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As described hereinafter, embodiments of the present disclosure relate to aerosol delivery devices or vaporization devices, said terms being used herein interchangeably. Aerosol delivery devices according to the present disclosure use electrical energy to heat a material (preferably without combusting the material to any significant degree and/or without significant chemical alteration of the material) to form an inhalable substance; and components of such devices have the form of articles that most preferably are sufficiently compact to be considered hand-held devices. That is, use of components of preferred aerosol delivery devices does not result in the production of smoke—i.e., from by-products of combustion or pyrolysis of tobacco, but rather, use of those preferred systems results in the production of vapors resulting from volatilization or vaporization of certain components incorporated therein. In preferred embodiments, components of aerosol delivery devices may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases, and aerosols of a form or type suitable for human inhalation, whether or not visible, and whether or not of a form that might be considered to be smoke-like.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microcontroller or microprocessor), a heater or heat generation member (e.g., an electrical resistance heating element or other component, which alone or in combination with one or more further elements may be commonly referred to as an "atomizer"), a liquid composition (e.g., commonly an aerosol precursor composition liquid capable of yielding an aerosol upon application of sufficient heat, such as ingredients commonly referred to as "smoke juice," "e-liquid" and "e-juice"), and a mouthpiece or mouth region for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of the commercially available electronic aerosol delivery devices, such as those representative products referenced in the background art section of the present disclosure.

In various implementations, the present disclosure relates to aerosol delivery devices and cartridges for aerosol delivery devices that provide visual indication of one or more characteristics of the device. For example, in some implementations a cartridge of an aerosol delivery device may include a liquid composition that includes a flavorant. The present disclosure relates to aerosol delivery devices and cartridges for aerosol delivery devices wherein the cartridge is configured to be removably received into the control device, and wherein when the cartridge is received in the control device at least one feature of the cartridge, or at least one feature of the control device, or at least one feature of both the cartridge and the control device, provides a visual indication of a color associated with the flavorant.

An example implementation of an aerosol delivery device 100 of the present disclosure is shown in FIG. 1. As illustrated, the aerosol delivery device 100 includes a control device 200 and a removable cartridge 300. Although only one cartridge is shown in the depicted implementation, it should be understood that, in various implementations, the aerosol delivery device 100 may comprise an interchangeable system. For example, in one or more implementations, a single control device may be usable with a plurality of different cartridges. Likewise, in one or more implementations, a single cartridge may be usable with a plurality of different control devices.

In various implementations, the control device 200 includes an outer housing 202 that defines an outer wall 204, which includes a distal end 206 and a proximal end 208. The aerosol delivery device 100 of the depicted implementation also includes an indication window 240 defined in the outer housing 202. FIG. 2 illustrates a partial cross-section of the control device 200 of the aerosol delivery device 100 of FIG. 1. As shown in the figure, the control device 200 also includes an inner frame 215 that includes a cartridge receiving chamber 212 defined by an inner frame wall 214. The control device 200 further includes a battery 216 positioned within the outer housing 202 and also includes an external connection element 218. In the depicted implementation, the external connection element 218 is positioned at the distal end 206 of the outer housing 202.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., the disclosure of which is incorporated herein by reference. In some implementations, other power sources may be utilized. For example, in various implementations a power source may comprise a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety. In further implementations, a power source may also comprise a capacitor. Capacitors are capable of discharging more quickly than batteries and can be charged between puffs, allowing the battery to discharge into the capacitor at a lower rate than if it were used to power the heating member directly. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor. Examples of power supplies that include supercapacitors are described in U.S. Pat. App. Pub. No. 2017/0112191 to Sur et al., which is incorporated herein by reference in its entirety.

In various implementations, the control device 200 may also include a light source 230 and at least one aperture 232 (see FIG. 1) defined in the outer wall 204 of the control device 200 and through which light from the light source 230 may be visible. In some implementations, the light source 230 may comprise, for example, at least one light emitting diode (LED) capable of providing one or more colors of light. In some implementations, the light source may be configured to illuminate in only one color, while in other implementations, the light source may be configured to illuminate in variety of different colors. In still other implementations, the light source may be configured to provide white light. As illustrated in FIG. 2, the light source 230 may be positioned directly on a control component 234 (such as, for example a printed circuit board (PCB)) on which further control components (e.g., a microcontroller and/or memory components) may be included. In various implementations, the aperture 232 may be provided in any desired shape and may particularly be positioned near the distal end 206 of the control device 200. In some implementations, the aperture 232 may be completely open or may be filled, such as with a light guide material, or may be covered with a transparent or translucent member (e.g., glass or plastic) on one or both of the inner surface and the outer surface of the outer wall 204 of the control device 200. The aerosol delivery device 100 may also include a control mechanism for controlling the amount of electric power to the heat generation element during draw. Representative types of electronic components, structure and configuration thereof, features thereof, and general methods of operation thereof, are described in U.S. Pat. No. 4,735,217 to Gerth et al.; U.S. Pat. No. 4,947,874 to Brooks et al.; U.S. Pat. No. 5,372,148 to McCafferty et al.; U.S. Pat. No. 6,040,560 to Fleischhauer et al.; U.S. Pat. No. 7,040,314 to Nguyen et al. and U.S. Pat. No. 8,205,622 to Pan; U.S. Pat. App. Pub. Nos. 2009/0230117 to Fernando et al., 2014/0060554 to Collet et al., and 2014/0270727 to Ampolini et al.; and U.S. Pat. App. Pub. No. 2015/0257445 to Henry et al.; which are incorporated herein by reference in their entireties.

Electrical connectors 220 may be positioned in the cartridge receiving chamber 212 and, in the depicted implementation, are present in sides of the inner frame wall 214. In various implementations, the electrical connectors 220 may be operatively connected to the battery (e.g. connected to the battery directly or via the control component 234). As will be discussed in more detail below, the electrical connectors may have a variety of forms and may be positioned in various other locations of the inner frame 215. As also illustrated in FIG. 2, the proximal end 208 of the outer housing 202 includes an opening 210 that provides access to the cartridge receiving chamber 212 defined by the inner frame 215. It should be noted that for the purposes of the present disclosure, the term "operatively connected" should be interpreted broadly so as to encompass components that are directly connected and/or connected via one or more additional components.

In various implementations, further indicators (e.g., a haptic feedback component, an audio feedback component, or the like) can be included in addition to or as an alternative to the light source. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; U.S. Pat. App. Pub. No. 2015/0020825 to Galloway et al.; and U.S. Pat. App. Pub. No. 2015/0216233 to Sears et al.; which are incorporated herein by reference in their entireties. It should be understood that not all of the illustrated elements are required. For example, an LED may be absent or may be replaced with a different indicator, such as a vibrating indicator.

In various implementations, an airflow sensor, pressure sensor, or the like may be included in the device. For example, as illustrated in FIG. 2, the control device 200 may include a sensor 236 on the control component 234. Configurations of a printed circuit board and a pressure sensor, for example, are described in U.S. Pat. App. Pub. No. 2015/0245658 to Worm et al., the disclosure of which is incorporated herein by reference in its entirety. In various implementations, the sensor 236 may be positioned anywhere within the control device 200 so as to subject to airflow and/or a pressure change that can signal a draw on the device and thus cause the battery 216 to delivery power to the heater in the cartridge 300. Alternatively, in the absence of an airflow sensor, the heater may be activated manually, such as via a push button that may be located on the control body 200 and/or the cartridge 300. Additional representative types of sensing or detection mechanisms, structure and configuration thereof, components thereof, and general methods of operation thereof, are described in U.S. Pat. No. 5,261,424 to Sprinkel, Jr.; U.S. Pat. No. 5,372,148 to McCafferty et al.; and PCT WO 2010/003480 to Flick; which are incorporated herein by reference in their entireties.

In some implementations, an input element may be included with the aerosol delivery device (and may replace or supplement an airflow or pressure sensor). The input may be included to allow a user to control functions of the device and/or for output of information to a user. Any component or combination of components may be utilized as an input for controlling the function of the device 100. For example, one or more pushbuttons may be used as described in U.S. Pat. App. Pub. No. 2015/0245658 to Worm et al., which is incorporated herein by reference in its entirety. Likewise, a touchscreen may be used as described in U.S. patent application Ser. No. 14/643,626, filed Mar. 10, 2015, to Sears et al., which is incorporated herein by reference in its entirety. As a further example, components adapted for gesture recognition based on specified movements of the aerosol delivery device may be used as an input. See U.S. Pat. App. Pub. 2016/0158782 to Henry et al., which is incorporated herein by reference in its entirety.

In some implementations, an input may comprise a computer or computing device, such as a smartphone or tablet. In particular, the aerosol delivery device may be wired to the computer or other device, such as via use of a USB cord or similar protocol. The aerosol delivery device may also communicate with a computer or other device acting as an input via wireless communication. See, for example, the systems and methods for controlling a device via a read request as described in U.S. Pat. App. Pub. No. 2016/0007561 to Ampolini et al., the disclosure of which is incorporated herein by reference in its entirety. In such embodiments, an APP or other computer program may be used in connection with a computer or other computing device to input control instructions to the aerosol delivery device, such control instructions including, for example, the ability to form an aerosol of specific composition by choosing the nicotine content and/or content of further flavors to be included.

Although other implementations may differ, in the depicted implementation, the inner frame 215 is separate from the outer housing 202. In such a manner, the inner frame 215 defining the cartridge receiving chamber 212 may exist independently and separately from the outer housing 202. An opening of the chamber may coincide with an opening at the proximal end 208 of the outer housing 202. Thus, in the depicted implementation, the inner frame wall 214 may be a completely different element that is attached to the outer housing 202; however, in other implementations the inner frame wall and the outer housing may be continuously formed. In either case, the sidewalls forming the inner frame wall are present interior to and separated from the outer housing.

In various implementations, the outer housing 202 may be formed of any suitable material, such as a metal, plastic, ceramic, glass, or the like. In some implementations, the inner frame 215 may be formed of a different material than that used to form the outer housing 202. For example, in some implementations the outer housing may comprise a metal material, and the inner frame may comprise a plastic material. In other implementations, the same materials may be used. Choice of materials as noted above may also extend to the outer housing for any further control device(s) that are included in the device.

An example implementation of a cartridge 300 for use in an aerosol delivery device of the present disclosure is shown in FIGS. 3A and 3B. In particular, FIG. 3A is a perspective view of a cartridge according to example implementations of the present disclosure, and FIG. 3B is a partial cross-section view of the cartridge illustrated in FIG. 3. As shown in FIGS. 3A and 3B, the cartridge 300 includes a tank 302 that is defined by an outer tank wall 304 that includes a proximal end 306 and a distal end 308, which is closed. As such, the tank 302 may be characterized in that the tank wall 304 is a sidewall that is continuous around the tank, and the distal end 308 defines a bottom wall. The tank 302 is also configured to contain a liquid composition 324 for vaporization (e.g., an e-liquid or aerosol precursor composition), which may be configured as otherwise described herein. The cartridge 300 also includes a mouthpiece 310 that is defined by an outer mouthpiece wall 312 that includes a proximal end 314 with an exit portal 315 defined therein, and a distal end 316 that engages the proximal end 306 of the tank 302.

For aerosol delivery systems that are characterized as electronic cigarettes, the aerosol precursor composition may incorporate tobacco or components derived from tobacco. In one regard, the tobacco may be provided as parts or pieces of tobacco, such as finely ground, milled or powdered tobacco lamina. Tobacco beads, pellets, or other solid forms may be included, such as described in U.S. Pat. App. Pub. No. 2015/0335070 to Sears et al., the disclosure of which is incorporated herein by reference. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

In the depicted implementation, the liquid composition, sometime referred to as an aerosol precursor composition or a vapor precursor composition or "e-liquid", may comprise a variety of components including, by way of example, a polyhydric alcohol (e.g., glycerin, propylene glycol, or a mixture thereof), nicotine, tobacco, tobacco extract, and/or flavorants. Representative types of aerosol precursor components and formulations also are set forth and characterized in U.S. Pat. No. 7,217,320 to Robinson et al. and U.S. Pat. App. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU™ products by Fontem Ventures B.V., the MISTIC MENTHOL product by Mistic Ecigs, MARK TEN products by Nu Mark LLC, the JUUL product by Juul Labs, Inc., and VYPE products by CN Creative Ltd. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MITTEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. In one or more embodiments, about 1 ml or more, about 2 ml or more, about 5 ml or more, or about 10 ml or more of the aerosol precursor composition may be included.

In some implementations, the liquid composition may include one or more flavorants. As used herein, reference to a "flavorant" refers to compounds or components that can be aerosolized and delivered to a user and which impart a sensory experience in terms of taste and/or aroma. Example flavorants include, but are not limited to, vanillin, ethyl vanillin, cream, tea, coffee, fruit (e.g., apple, cherry, strawberry, peach and citrus flavors, including lime and lemon), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, yerba santa, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavorant should not be limited to any single flavorant as described above, and may, in fact, represent a combination of one or more flavorants.

As shown in FIG. 3B, the cartridge 300 further includes a heater 320 and a liquid transport element 322 that extends between the heater and the liquid composition 324 contained within the tank 302. In various implementations, the heater 320 and liquid transport element 322 may be configured as separate elements that are fluidly connected or may be configured as a combined element. Moreover, the heater 320 and the liquid transport element 322 may be formed of any construction as otherwise described herein. The cartridge 300 also includes one or more electrical contacts 325 that are configured to electrically connect the heater 320 with the battery 216 and/or control component 234 of the control device 200.

In various implementations, the liquid transport element 322 may be formed of one or more materials configured for transport of a liquid, such as by capillary action. In some implementations, for example, a liquid transport element may be formed of fibrous materials (e.g., organic cotton, cellulose acetate, regenerated cellulose fabrics, glass fibers), porous ceramics, porous carbon, graphite, porous glass, sintered glass beads, sintered ceramic beads, capillary tubes, or the like. The liquid transport element 322 thus may be any material that contains an open pore network (i.e., a plurality of pores that are interconnected so that fluid may flow from one pore to another in a plurality of direction through the element). As further discussed herein, some implementations of the present disclosure may particularly relate to the use of non-fibrous transport elements. As such, fibrous transport elements may be expressly excluded. Alternatively, combinations of fibrous transport elements and non-fibrous transport elements may be utilized. Representative types of substrates, reservoirs or other components for supporting the aerosol precursor are described in U.S. Pat. No. 8,528,569 to Newton; U.S. Pat. App. Pub. Nos. 2014/0261487 to Chapman et al. and 2014/0059780 to Davis et al.; and U.S. Pat. App. Pub. No. 2015/0216232 to Bless et al.; which are incorporated herein by reference in their entireties. Additionally, various wicking materials, and the configuration and operation of those wicking materials within certain types of electronic cigarettes, are set forth in U.S. Pat. No. 8,910,640 to Sears et al.; which is incorporated herein by reference in its entirety. In some implementations, the liquid transport element 322 may be formed partially or completely from a porous monolith, such as a porous ceramic, a porous glass, or the like. Example monolithic materials suitable for use according to embodiments of the present disclosure are described, for example, in U.S. Pat. App. Pub. No. 2017/0188626, and U.S. Pat. App. Pub. No. 2014/0123989 to LaMothe, the disclosures of which are incorporated herein by reference in their entireties. In some implementations, the porous monolith may form a substantially solid wick.

In various implementations, the heater 320 may comprise one or more different materials configured to produce heat when electrical current is applied therethrough. In some implementations, the heater 320 may be a wire coil. Example materials from which the wire coil may be formed include stainless steel, pure nickel, nickel-iron alloys, Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, alloys of silver and palladium, graphite and graphite-based materials (e.g., carbon-based foams and yarns). In further implementations, the heater 320 may be formed from conductive inks, boron doped silica, and/or ceramics (e.g., positive or negative temperature coefficient ceramics). Other types of heaters may also be utilized, such as laser diodes or microheaters. A laser diode can be configured to deliver electromagnetic radiation at a specific wavelength or band of wavelengths that can be tuned for vaporization of the aerosol precursor composition and/or tuned for heating a liquid transport element via which the aerosol precursor composition may be provided for vaporization. The laser diode can particularly be positioned so as to deliver the electromagnetic radiation within a chamber, and the chamber may be configured to be radiation-trapping (e.g., a black body or a white body). Suitable microheaters are described in U.S. Pat. No. 8,881,737 to Collett et al., which is incorporated herein by reference in its entirety. Microheaters, for example, can comprise a substrate (e.g., quartz, silica) with a heater trace thereon (e.g., a resistive element such as Ag, Pd, Ti, Pt, Pt/Ti, boron-doped silicon, or other metals or metal alloys), which may be printed or otherwise applied to the substrate. A passivating layer (e.g., aluminum oxide or silica) may be provided over the heater trace. The heater 320 in particular may be configured to be substantially flat. Such heaters are described in U.S. Pat. App. Pub. No. 2016/0345633 to DePiano et al., which is incorporated herein by reference in its entirety.

In the depicted implementation, the outer tank wall 304 is configured to be one of at least partially transparent or translucent so that the liquid composition 324 contained therein is visible externally. As such, in some implementations, the entire outer tank wall 304 may be transparent or translucent. Alternatively, in some implementations, only a single side of the outer tank wall 304 may be transparent or translucent while the remaining portions of the outer tank wall may be substantially opaque. In some embodiments, the outer tank wall 304 may be substantially opaque, and a strip (e.g., about 1 mm wide to about 20 mm wide or about 2 mm wide to about 18 mm wide or about 5 mm wide to about 15 mm wide) extending from the proximal end 306 of the tank 302 to the distal end 308 of the tank may be transparent or translucent. In further implementations, the outer tank wall 304 may be colored. In some implementations, the color can be configured so that the liquid composition 324 within the tank 302 is still visible, such by using a transparent or translucent outer tank wall. In other implementations, the tank wall can be configured so that the outer tank wall 304 has substantially opaque color.

In various implementations, the control device 200 may be configured so that at least a portion of the tank 302 is visible when the cartridge 300 is engaged with the control device 200. As noted above, in some implementations, at least a portion of the outer tank wall 304 may be configured to be one of at least partially transparent or translucent so that the liquid composition 324 contained therein is visible externally, and the outer wall 204 of the control device 200 may be configured to include an indication window 240 through which a portion of the outer tank wall 304 and any liquid composition 324 present in the tank 302 can be visible when the cartridge 300 is engaged with the control device 200.

In various implementations, the aerosol delivery device 100 and/or the control device 200 of the aerosol delivery device 100 may further include an external connector configured for electrical contact with each of the device external connection element (e.g., device external connection element 218). The external connector may include a first connector end and a second connector end interconnected by a union, which may be, for example, a cord of variable length. In various implementations, the first connector end may be configured for electrical and, optionally, mechanical connection with the control device. In particular, the first connector end may include an inset wall that can be received within a well present at the distal end 206 of the control device 200. The external connector may include a plurality of electrical pins interior to the inset wall configured for making a charging and/or information transferring connection with the device external connection element 218. In some implementations, the control device 200 may include a mechanical connector (e.g., a mechanical connector 242) adjacent the control device external connection element 218. In some implementations, the mechanical connector 242 may be a magnet or a metal (or like element) that is adapted for magnetic attraction to a magnet. The first connector end of the external connection may then likewise include a mechanical connection element that may be positioned between the inset wall and the electrical pins. In various implementations, the mechanical connection element may be a magnet or a metal (or like element) that is adapted for magnetic attraction to a magnet. The second connector end may be configured for connection to a computer or similar electronic device or for connection to a power source. For example, the second connector end may have a Universal Serial Bus (USB) connection; however, a different connection may also be provided and/or an adapter may likewise be included (e.g., a USB/AC adapter). For example, an adaptor including a USB connector at one end and a power unit connector at an opposing end is disclosed in U.S. Pat. App. Pub. No. 2014/0261495 to Novak et al., which is incorporated herein by reference in its entirety.

Yet other features, controls or components that can be incorporated into aerosol delivery devices of the present disclosure are described in U.S. Pat. No. 5,967,148 to Harris et al.; U.S. Pat. No. 5,934,289 to Watkins et al.; U.S. Pat. No. 5,954,979 to Counts et al.; U.S. Pat. No. 6,040,560 to Fleischhauer et al.; U.S. Pat. No. 8,365,742 to Hon; U.S. Pat. No. 8,402,976 to Fernando et al.; U.S. Pat. App. Pub. Nos. 2010/0163063 to Fernando et al.; 2013/0192623 to Tucker et al.; 2013/0298905 to Leven et al.; 2013/0180553 to Kim et al., 2014/0000638 to Sebastian et al., 2014/0261495 to Novak et al., and 2014/0261408 to DePiano et al.; which are incorporated herein by reference in their entireties.

In various implementations, the mouthpiece 310 of the cartridge 300 may be configured for engagement with the tank 302. For example, as illustrated in FIG. 3B, the distal end 316 of the mouthpiece 310 may include a rim wall 330 that is at least partially inset from the outer mouthpiece wall 312. The rim wall 330 may be configured to engage an interior of the proximal end 306 of the outer tank wall 304. In some implementations, the rim wall 330 may have a length of about 1 mm to about 20 mm, about 2 mm to about 18 mm, or about 5 mm to about 15 mm. In some implementations, the rim wall 330 may engage the outer tank wall 304 via a friction fit alone, or the rim wall may be substantially permanently attached to the outer tank wall, such as through welding or gluing.

In some implementations, the mouthpiece 310 may define an open interior space through which formed vapor may combine with air to form an aerosol for output through the exit portal 315 of the mouthpiece 310. In one or more implementations, the mouthpiece 310 may include one or more further interior walls that can be arranged to define one or more compartments within the mouthpiece. For example, the mouthpiece may include an interior upper wall between the proximal end and the distal end of the mouthpiece and also include an interior lower wall between the interior upper wall and the proximal end of the mouthpiece. More particularly, as seen in FIG. 3B, the mouthpiece 310 may include an interior upper wall 332 between the proximal end 314 and the distal end 316 of the mouthpiece 310. Further, the mouthpiece 310 may include an interior lower wall 334 between the interior upper wall 332 and the distal end 316 of the mouthpiece 310.

In various implementations, two or more walls in the mouthpiece may be configured to define a vaporization chamber within which the heater may be positioned. As shown in FIG. 3B, the outer mouthpiece wall 312, the interior upper wall 332, and the interior lower wall 334 define a vaporization chamber 340 wherein the heater 320 is positioned. In some implementations, the one or more electrical contacts 325 may be positioned within the portion of the outer mouthpiece wall 312 defining the vaporization chamber 340; however, it is understood that one or more electrical leads may extend from the heater 320 to one or more electrical contacts positioned at a different portion of the outer mouthpiece wall or positioned in the outer tank wall 304. One or more walls of the mouthpiece may also include one or more openings for passage therethrough of one or more further elements of the cartridge 300 or passage of formed vapor/aerosol. For example, the interior upper wall 332 may include a vapor opening 336 through which vapor formed in the vaporization chamber 340 may pass toward the first exit portal 315. In some implementations, the vapor opening 336 in the interior upper wall 332 may be substantially centrally located therein and may be substantially aligned with the heater 320 along a longitudinal axis of the cartridge 300. As a further example, the interior lower wall 334 may include a wick aperture 338 through which the first liquid transport element 322 (e.g., a wick) can pass between the heater 320 and the liquid composition 324 in the tank 302.

In various implementations, two or more walls in the mouthpiece may be configured to define a cooling chamber within which formed aerosol can be allowed to expand and/or cool before passing through the exit portal. As shown in FIG. 3B, for example, the outer mouthpiece wall 312 and the interior upper wall 332 define a cooling chamber 342 that receives formed vapor/aerosol from the vaporization chamber 340. As such, the vapor/aerosol formed by the heater 320 passes from the vaporization chamber 340 through the vapor opening 336 and into the cooling chamber 342. In some implementations, the vaporization chamber 340 and the cooling chamber 342 may be configured to have a defined relative volume ratio. For example, in some implementations, the volume ratio of the vaporization chamber 340 to the cooling chamber 342 can be about 2:1 to about 1:4, about 1:1 to about 1:4, or about 1:1.5 to about 1:3.

If desired, the mouthpiece 310 may also include one or more elements configured to reduce or prevent leakage of condensed liquids therefrom. For example, in some implementations, all or a part of the interior of the mouthpiece wall 312 and/or the interior upper wall 332 defining the cooling chamber 342 may be formed from or include an absorptive or adsorptive material configured to hold liquid. Alternatively or additionally, all or a part of the interior of the mouthpiece wall 312 and/or the interior upper wall 332 defining the cooling chamber 342 may be configured to direct liquid back toward the vaporization chamber 340, such as through the addition of microchannels or the like.

In one or more implementations, the cartridge 300 may be configured such that the mouthpiece wall 312 includes a flange positioned between the proximal end 314 and the distal end 316 thereof. For example, referring to FIGS. 3A and 3B, the mouthpiece 310 includes a flange 350 that extends circumferentially from the mouthpiece wall 312 around substantially the entirety of the mouthpiece 310. In some implementations, the distance that the flange 350 extends from the mouthpiece wall 310 can be substantially uniform around the entire circumference of the mouthpiece 310. In other implementations (such as the depicted implementation) the distance that the flange 350 extends from the mouthpiece wall 312 may vary at one or more points around the circumference of the mouthpiece 310. The overall cartridge 300 or the mouthpiece 310 separately can be defined in relation to a longitudinal axis (L), a first transverse axis (T1) that is perpendicular to the longitudinal axis, and a second transverse axis (T2) that is perpendicular to the longitudinal axis and is perpendicular to the first transverse axis.

In some implementations, the overall cartridge 300 and/or the mouthpiece 310 thus may be defined in relation to a total length along the longitudinal axis (L), a total width along the first transverse axis (T1), and a total depth along the second longitudinal axis (T2). The length may be greater than the width, which in turn may be greater than the depth. The distance that the flange 350 extends away from the mouthpiece wall 312 may be greater along the second transverse axis (T2) than along the first transverse axis (T1). Thus, in some implementations, the total distance between opposing outer edges of the flange 350 across the mouthpiece 310 along the first transverse axis (T1) may be greater than the total distance between opposing edges of the flange across the mouthpiece along the second transverse axis (T2); the total distance between opposing outer edges of the flange 350 across the mouthpiece 310 along the first transverse axis (T1) may be substantially equal to the total distance between opposing edges of the flange across the mouthpiece along the second transverse axis (T2); or the total distance between opposing outer edges of the flange 350 across the mouthpiece 310 along the first transverse axis (T1) may be less than the total distance between opposing edges of the flange across the mouthpiece along the second transverse axis (T2). In particular implementations, a distance (d2) between the mouthpiece wall 312 and an outer edge of the flange 350 as measured along the second transverse axis (T2) may be greater than a distance between the mouthpiece wall and an outer edge of the flange as measured along the first transverse axis (T1). Said distances particularly may be as measured at about a midpoint of each of the first transverse axis (T1) and the second transverse axis (T2).

According to the present disclosure, the cartridge and the control device each include at least one connector configured to provide a magnetic and an electrical connection between the cartridge and the control device such that the cartridge can be removably and operatively received into the cartridge receiving chamber of the control body, and wherein the at least one connector of the cartridge is located on the mouthpiece. As will be discussed in more detail below, in various implementations the at least one connector of the cartridge and the control device may have a variety of different forms, shapes, sizes, positions, etc., so as to provide a magnetic and an electrical connection between the cartridge and the control device. In addition, in various implementations the same connector of the cartridge and/or the control device may provide one or both of the magnetic and the electrical connections.

For example, FIG. 4A illustrates a partial perspective view of an inner frame of a control device according to an example implementation of the present disclosure. In particular, FIG. 4A illustrates a portion of an inner frame 415 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 415 of the depicted implementation includes a cartridge receiving chamber 412 and a flange 450 defined at an upper end thereof. The inner frame 415 of the depicted implementation also includes a plurality of magnets 452 located proximate the upper flange 450 of the inner frame 415. In the depicted implementation, there are four individual magnets 452A, 452B, 452C, 452D, each of which has a substantially block-like or rectangular prismatic shape, although in other implementation more or less individual magnets may be used and the magnets may have different shapes and/or sizes. In the depicted implementation, the magnets 452A, 452B, 452C, 452D are approximately equally spaced around the outside of the inner frame 415 and below the upper flange 450 thereof, with each of the plurality of magnets being located inside a corresponding magnet receiving feature 453, which, in the depicted implementation, is an extension of the upper flange 450. Although other methods are possible, the magnets 452A, 452B, 452C, 452D of the depicted implementation may be affixed inside the magnet receiving features 453 via a press-fit and/or adhesive connection, or via an insert molding process.

In various implementations of the present disclosure, the magnets described above, or any other magnets described herein, may comprise many different types of magnets, including rare earth magnets. For example, in some implementations, one or more magnets may comprise Neodymium magnets (also known as NdFeB, NIB, or Neo magnets). In various implementations, different grades of Neodymium magnets may be used, including, for example, N35, N38, N40, N42, N45, N48, N50, and/or N52 grades. In other implementations, one or more magnets may comprise Samarium Cobalt magnets (also known as SmCo magnets). In still other implementations, one or more magnets may comprise Ceramic/Ferrite magnets. In other implementations, one or more magnets may comprise Aluminum-Nickel-Cobalt (AlNiCo) magnets. In any of the foregoing implementations, one or more magnets may be plated and/or coated. For example, in some implementations, one or more magnets may be coated with nickel. In other implementations, one or more magnets may be coated with one or more of zinc, tin, copper, epoxy, silver and/or gold. In some implementations, one or more magnets may be coated with combinations of these materials. For example, in one implementation, one or more magnets may be coated with nickel, copper, and nickel again. In another implementation, one or more magnets may be coated with nickel, copper, nickel, and a top coating of gold.

The inner frame 415 of the depicted implementation also includes a pair of conductive pins 420A, 420B located in the inner frame 415 and below the upper flange 450 thereof. In the depicted implementation, the conductive pins 420A, 420B are operatively connected to the battery of the control device in order, as will be discussed below, to provide power to the heater of an inserted cartridge. The conductive pins 420A, 420B of the depicted implementation comprise spring-loaded pins (e.g., electrical pogo pins), each of which is biased inward such that a portion of the end of the pin extends into the cartridge receiving chamber 412 and is configured to deflect outward against the force of an integral spring, although in other implementations other types of conductive elements may be used. In the depicted implementation, the conductive pins 420A, 420B comprise gold plated metal pins; however, other materials or combinations of materials, which may also include coatings and/or platings of electrically conductive materials, are possible. Examples of electrically conductive materials, include, but are not limited to, copper, beryllium copper, aluminum, platinum, gold, silver, iron, steel, brass, bronze, graphite, conductive ceramic materials, and/or any combination thereof. In the depicted implementation, ends of the conductive pins 420A, 420B have a rounded profile, although other profiles are possible, such that deflection of the conductive pins 420A, 420B is facilitated when a cartridge is inserted into the receiving chamber 412. In the depicted implementation, the conductive pins 420A, 420B may be affixed inside the inner frame 415 via a press-fit and/or adhesive connection, or via an insert molding process, such that the movable components of the conductive pins are able to deflect outward against the force of the springs.

FIG. 4B illustrates a perspective view of a cartridge according to an example implementation of the present disclosure. In particular, FIG. 4B illustrates a cartridge 500 that includes a tank 502 that is defined by an outer tank wall 504 that includes a proximal end 506 and a distal end 508, which is closed. In many aspects, the cartridge 500 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 500 of the depicted implementation includes a mouthpiece 510 that is defined by an outer mouthpiece wall 512 that includes a proximal end 514 with an exit portal 515 defined therein, and a distal end 516 that engages the proximal end 506 of the tank 502. In the depicted implementation, the mouthpiece wall 512 includes a flange 550 positioned between the proximal end 514 and the distal end 516 thereof. The cartridge 500 of the depicted implementation also includes a metal plate 552, which is disposed below the flange 550. In the depicted implementation, the metal plate 552 is affixed to the bottom of the flange 550 of the mouthpiece 510 via an adhesive, although in other implementations other methods of attachment are possible, including, for example, via an insert molding process. In various implementations, the metal plate 552 may comprise any material configured to be attracted by a magnet, such as various ferromagnetic materials, including, but not limited, to iron, nickel, cobalt, alloys such as steel, and/or any combination thereof. The cartridge 500 also includes a pair of conductive plugs 525A, 525B located on opposite sides of the mouthpiece 510 and below the flange 550 and metal plate 552. In the depicted implementation, the conductive plugs 525A, 525B may be affixed inside the mouthpiece 510 of the cartridge 500 via an adhesive, although in other implementations other methods of attachment of possible, including, for example, via an insert molding process. In the depicted implementation, the conductive plugs 525A, 525B are operatively connected to a heater 520 (see FIG. 5) of the cartridge 500. In various implementations, the conductive plugs 525A, 525B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

In various implementations, a portion of the cartridge 500 of FIG. 4B is configured to be coupled with the cartridge receiving chamber 412 of the inner frame 415 of FIG. 4A, such that magnetic and electrical connections are created between the cartridge and the control device. In particular, FIG. 5 illustrates a partial cross-section view of the cartridge 500 coupled with the inner frame 415 of the control device. As illustrated in the figure, when the cartridge 500 of the depicted implementation is coupled with the inner frame 415 of the control device, a magnetic connection is created between the plurality of magnets 452A, 452B, 452C, 452D located in the inner frame 415 of the control device and the metal plate 552 of the cartridge 500. In addition, when the cartridge 500 of the depicted implementation is coupled with the inner frame 415, an electrical connection is created between the pair conductive pins 420A, 420B of the inner frame 415 of the control device and the conductive plugs 525A, 525B of the cartridge 500. As such, when the cartridge 500 is received in the inner frame 415 of the control device, the heater 520 of the cartridge 500 may be operatively connected to the battery of the control device. Thus, when the cartridge 500 of the depicted implementation is coupled with the inner frame 415 of the control device, the cartridge 500 is mechanically biased into connection with the inner frame 415 of the control device such that the electrical connection is maintained between the cartridge and the control device.

It should be noted that for this implementation, and/or any other implementation described herein, the magnets may facilitate proper rotational orientation of a cartridge relative to a control device. For example, while in some implementations the cartridge may be installed in the control device in any rotational orientation, and in other implementations the geometry of the cartridge and/or the control device may facilitate proper rotational orientation of the cartridge relative to the control device, in still other implementations the magnets in the cartridge and the magnets in the control device may facilitate proper rotational orientation of the cartridge relative to the control device. For example, if a like pole of a magnet in the cartridge is inserted near a like pole of a magnet in the control device (e.g., the North Pole of a magnet in the cartridge and the North Pole of a magnet in the control device, or the South Pole of a magnet in the cartridge and the South Pole of a magnet in the control device) the magnets will repel each other. However, if opposite poles are placed near each other (e.g., the North Pole of a magnet in the cartridge and the South Pole of a magnet in the control device, or the South Pole of a magnet in the cartridge and the North Pole of a magnet in the control device) the magnet will attract each other. As a result, positioning of the polarity of the magnets in the cartridge and the control device may be configured such that the opposite poles of the magnets attract each other in the proper rotational orientation of the cartridge relative to the control device and repel each other in other rotational orientations of the cartridge relative to the control device.

FIG. 6 illustrates a partial perspective view of an inner frame 615 of a control according to another example implementation of the present disclosure. In particular, the inner frame 615 of the depicted implementation includes a flange 650 defined at an upper end thereof, and a plurality of magnets 652 located proximate the upper flange 450 of the inner frame 615. In the depicted implementation, there are four individual magnets 652A, 652B, 652C, 652D. In various implementations, the magnets 652A, 652B, 652C, 652D are configured to facilitate a magnetic connection between the inner frame 615 of a control device and a cartridge (such as, for example, cartridge 500 of FIG. 4B). As such, the magnets 652A, 652B, 652C, 652D of the depicted implementation are similar to the magnets described with respect to FIG. 4A. For example, there are four individual magnets 652A, 652B, 652C, 652D in the depicted implementation, each of which has a substantially block-like or rectangular prismatic shape, although more or less individual magnets may be used and the magnets may have different shapes and/or sizes. Reference is made to the possible magnet materials discussed above. The inner frame 615 of the depicted implementation also includes a pair of conductive pins 620A, 620B located in the inner frame 615 and below the upper flange 650 thereof. As with the magnets 652A, 652B, 652C, 652D, the conductive pins 620A, 620B of the depicted implementation are similar to the conductive pins of the implementation of FIG. 4A. For example, the conductive pins 620A, 620B of the depicted implementation comprise spring-loaded pins (e.g., electrical pogo pins), each of which is biased inward such that a portion of the end of the pin extends into the cartridge receiving chamber 612 and is configured to deflect outward against the force of an integral spring, although in other implementations other types of conductive elements may be used. Reference is made to the possible materials for the conductive pins described above. In the depicted implementation, the conductive pins 620A, 620B may be affixed inside the inner frame 615 via a press-fit and/or adhesive connection, or via an insert molding process, such that the movable components of the conductive pins are able to deflect outward against the force of the springs.

FIG. 7 illustrates a partial cross-section view of cartridge 500 coupled with inner frame 615. In the depicted implementation, the magnets 652A, 652B, 652C, 652D are approximately equally spaced around the outside of the inner frame 615, with each magnet located inside of a corresponding magnet receiving feature 653 (see FIG. 6). Although other methods are possible, the magnets 652A, 652B, 652C, 652D of the depicted implementation may be affixed inside the magnet receiving features 653 via a press-fit and/or adhesive connection, or via an insert molding process. Unlike the implementation of FIG. 4A, however, the magnets 652A, 652B, 652C, 652D of the depicted implementation are exposed in a top surface of the upper flange 650 of the inner frame 615 such that when cartridge 500 is coupled with the inner frame 615 of the control device, the magnets 652A, 652B, 652C, 652D make direct contact with the metal plate 552 of the cartridge 500. In such a manner, when using a similar magnet configuration, the magnetic connection between the cartridge 500 and the inner frame 615 of the implementation of FIG. 7 may be stronger than the magnetic connection of the implementation of FIG. 5.

FIG. 8A illustrates a perspective view of an inner frame of a control device according to an example implementation of the present disclosure, and FIG. 8B illustrates a partial exploded top view of an inner frame of a control device according to an example implementation of the present disclosure. In particular, FIGS. 8A and 8B illustrate an inner frame 815 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 815 of the depicted implementation includes a cartridge receiving chamber 812 and a plurality of flange features 856 that extend outward from an upper portion 858 of the inner frame 815. Although other configurations are possible, the flange features 856 of the depicted implementation are approximately equally spaced around the periphery of the upper portion 858 of the inner frame 815. The upper portion 858 of the inner frame 815 also defines an angled surface 860, which angles downward and inward with respect to a top edge thereof. The inner frame 815 of the depicted implementation also includes a plurality of magnets 852 located in the angled surface 860. In the depicted implementation, there are four individual magnets 852A, 852B, 852C, 852D, each of which has a substantially block-like or rectangular prismatic shape, although in other implementations more or less individual magnets may be used and the magnets may have different shapes and/or sizes. Reference is made to the possible magnet materials discussed above. In the depicted implementation, the magnets 852A, 852B, 852C, 852D are approximately equally spaced around the angled surface 860 of the inner frame 815. Although other methods are possible, the magnets 852A, 852B, 852C, 852D of the depicted implementation may be affixed inside angled surface 860 via a press-fit and/or adhesive connection, or via an insert molding process.

In addition, the inner frame 815 of the depicted implementation also includes a pair of conductive pins 820A, 820B (not shown in FIG. 8A) located in the inner frame 815 and proximate the upper portion 858 thereof. In the depicted implementation, the conductive pins 820A, 820B comprise spring-loaded pins (e.g., electrical pogo pins), each of which is biased inward such that a portion of the end of the pin extends into the cartridge receiving chamber 812 and is configured to deflect outward against the force of an integral spring, although in other implementations other types of conductive elements may be used. In the depicted implementation, ends of the conductive pins 820A, 820B have a rounded profile, although other profiles are possible, such that deflection of the conductive pins 820A, 820B is facilitated when a cartridge is inserted into the receiving chamber 812. In the depicted implementation, the conductive pins 820A, 820B may be affixed inside the inner frame 815 via a press-fit and/or adhesive connection, or via an insert molding process, such that the movable components of the conductive pins are able to deflect outward against the force of the springs. In the depicted implementation the conductive pins 820A, 820B are operatively connected to the battery of the control device in order, as will be discussed below, to provide power to the heater of an inserted cartridge. In various implementations, the conductive pins 820A, 820B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 8C illustrates a perspective view of a cartridge according to an example implementation of the present disclosure. In particular, FIG. 8C illustrates a cartridge 700 that includes a tank 702 that is defined by an outer tank wall 704 that includes a proximal end 706 and a distal end 708, which is closed. In many aspects, the cartridge 700 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 700 of the depicted implementation includes a mouthpiece 710 that is defined by an outer mouthpiece wall 712 that includes a proximal end 714 with an exit portal 715 defined therein, and a distal end 716 that engages the proximal end 706 of the tank 702. In the depicted implementation, the mouthpiece wall 712 includes a flange 750 positioned between the proximal end 714 and the distal end 716 thereof. The flange 750 of the depicted implementation also includes an angled surface 760 defined below an upper portion thereof. The cartridge 700 of the depicted implementation also includes a plurality of magnets 752 located in the angled surface 760. In the depicted implementation, there are four individual magnets 752A, 752B, 752C, 752D, each of which has a substantially block-like or rectangular prismatic shape, although in other implementation more or less individual magnets may be used and the magnets may have different shapes and/or sizes. Reference is made to the possible magnet materials discussed above. In the depicted implementation, the magnets 752A, 752B, 752C, 752D are approximately equally spaced around the angled surface 760 of the flange 750 of the cartridge 700. Although other methods are possible, the magnets 752A, 752B, 752C, 752D of the depicted implementation may be affixed inside angled surface 760 via a press-fit and/or adhesive connection, or via an insert molding process.

Although not shown in the figure, the cartridge 700 also includes a pair of conductive plugs similar to the conductive plugs described above with respect to cartridge 500 of FIG. 4B. In particular, the conductive plugs are located on opposite sides of the mouthpiece 710 and below the flange 750. In the depicted implementation, the conductive plugs may be affixed inside the mouthpiece 710 of the cartridge 700 via an adhesive, although in other implementations other methods of attachment of possible, including, for example, via an insert molding process. In the depicted implementation, the conductive plugs are operatively connected to a heater 720 (see FIG. 9) of the cartridge 700. In various implementations, the conductive plugs may be constructed of any electrically conductive material, including, for example, but not limited to, copper, beryllium copper, aluminum, platinum, gold, silver, iron, steel, brass, bronze, graphite, conductive ceramic materials, and/or any combination thereof. In various implementations, a portion of the cartridge 700 of FIG. 8C is configured to be coupled with the cartridge receiving chamber 812 of the inner frame 815 of FIGS. 8A and 8B, such that magnetic and electrical connections are created between the cartridge and the control device. In particular, FIG. 9 illustrates a partial cross-section view of the cartridge 700 coupled with the inner frame 815 of the control device. In the depicted implementation, the angled surface 860 of the inner frame 815 is configured to complement the angled surface 760 of the flange 750 of the cartridge 700. As such, when the cartridge 700 of the depicted implementation is coupled with the inner frame 815 of the control device, a magnetic connection is created between the plurality of magnets 852A, 852B, 852C, 852D located in angled surface 860 of the inner frame 815 of the control device, and the plurality of magnets 752A, 752B, 752C, 752D located in the angled surface 760 of the cartridge 700. In addition, when the cartridge 700 of the depicted implementation is coupled with the inner frame 815, an electrical connection is created between the pair conductive pins 820A, 820B of the inner frame 815 of the control device and the conductive plugs of the cartridge 700. As such, when the cartridge 700 is received in the inner frame 815 of the control device, the heater 720 of the cartridge 700 may be operatively connected to the battery of the control device. Thus, when the cartridge 700 of the depicted implementation is coupled with the inner frame 815 of the control device, the cartridge 700 is mechanically biased into connection with the inner frame 815 of the control device via the magnetic connection such that the electrical connection is maintained between the cartridge and the control device. It should be noted that in other implementations, either the plurality of magnets 852A, 852B, 852C, 852D of the inner frame 815 of the control device or the plurality of magnets 752A, 752B, 752C, 752D of the cartridge (or a combination of both) may be replaced with metal plates in order to effect the magnetic connection between the cartridge 700 and the inner frame 815 of the control device.

FIG. 10A illustrates a perspective view of an inner frame of a control device according to an example implementation of the present disclosure, and FIG. 10B illustrates a partial exploded top view of an inner frame of a control device according to an example implementation of the present disclosure. In particular, FIGS. 10A and 10B illustrate an inner frame 1015 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 1015 of the depicted implementation includes a cartridge receiving chamber 1012 and a plurality of flange features 1056 that extend outward from an upper portion 1058 of the inner frame 1015. Although other configurations are possible, the flange features 1056 of the depicted implementation are approximately equally spaced around the periphery of the upper portion 1058 of the inner frame 1015. The upper portion 1058 of the inner frame 1015 also defines an angled surface 1060, which angles downward and inward with respect to a top edge thereof. The inner frame 1015 of the depicted implementation also includes a plurality of magnets 1052 located in the angled surface 1060. In the depicted implementation, there are four individual magnets 1052A, 1052B, 1052C, 1052D, each of which has a substantially block-like or rectangular prismatic shape, although in other implementation more or less individual magnets may be used and the magnets may have different shapes and/or sizes. Reference is made to the possible magnet materials discussed above. In the depicted implementation, the magnets 1052A, 1052B, 1052C, 1052D are approximately equally spaced around the angled surface 1060 of the inner frame 1015. Although other methods are possible, the magnets 1052A, 1052B, 1052C, 1052D of the depicted implementation may be affixed inside angled surface 1060 via a press-fit and/or adhesive connection, or via an insert molding process.

In addition, the inner frame 1015 of the depicted implementation also includes a pair of conductive pins 1020A, 102B (not shown in FIG. 10A) located in the inner frame 1015 and proximate the upper portion 1058 thereof. In the depicted implementation, the conductive pins 1020A, 1020B comprise spring-loaded pins (e.g., electrical pogo pins), each of which is biased inward such that a portion of the end of the pin extends into the cartridge receiving chamber 1012 and is configured to deflect outward against the force of an integral spring, although in other implementations other types of conductive elements may be used. In the depicted implementation, ends of the conductive pins 1020A, 1020B have a rounded profile, although other profiles are possible, such that deflection of the conductive pins 1020A, 1020B is facilitated when a cartridge is inserted into the receiving chamber 1012. In the depicted implementation, the conductive pins 1020A, 1020B may be affixed inside the inner frame 1015 via a press-fit and/or adhesive connection, or via an insert molding process, such that the movable components of the conductive pins are able to deflect outward against the force of the springs. In the depicted implementation the conductive pins 1020A, 1020B are operatively connected to the battery of the control device in order, as will be discussed below, to provide power to the heater of an inserted cartridge. In various implementations, the conductive pins 1020A, 1020B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 10C illustrates a perspective view of a cartridge according to an example implementation of the present disclosure. In particular, FIG. 10C illustrates a cartridge 900 that includes a tank 902 that is defined by an outer tank wall 904 that includes a proximal end 906 and a distal end 908, which is closed. In many aspects, the cartridge 900 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 900 of the depicted implementation includes a mouthpiece 910 that is defined by an outer mouthpiece wall 912 that includes a proximal end 914 with an exit portal 915 defined therein, and a distal end 916 that engages the proximal end 906 of the tank 902. In the depicted implementation, the mouthpiece wall 912 includes a flange 950 positioned between the proximal end 914 and the distal end 916 thereof. In the depicted implementation, the flange 950 of the cartridge 900 also includes a metal ring 952 that defines an angled surface 960. In the depicted implementation, the metal ring 952 is affixed to the bottom of the flange 950 of the mouthpiece 910 via an adhesive, although in other implementations other methods of attachment of possible, including, for example, via an insert molding process. In various implementations, the metal ring 952 may comprise any material configured to be attracted by a magnet, such as various ferromagnetic materials, including, but not limited, to iron, nickel, cobalt, alloys such as steel, and/or any combination thereof.

Although not shown in the figure, the cartridge 900 also includes a pair of conductive plugs similar to the conductive plugs described above with respect to cartridge 500 of FIG. 4B. In particular, the conductive plugs are located on opposite sides of the mouthpiece 910 and below the flange 950. In the depicted implementation, the conductive plugs may be affixed inside the mouthpiece 910 of the cartridge 900 via an adhesive, although in other implementations other methods of attachment of possible, including, for example, via an insert molding process. In the depicted implementation, the conductive plugs are operatively connected to a heater 920 (see FIG. 11) of the cartridge 900. In various implementations, the conductive plugs may be constructed of any electrically conductive material, including, for example, but not limited to, copper, beryllium copper, aluminum, platinum, gold, silver, iron, steel, brass, bronze, graphite, conductive ceramic materials, and/or any combination thereof.

In various implementations, a portion of the cartridge 900 of FIG. 10C is configured to be coupled with the cartridge receiving chamber 1012 of the inner frame 1015 of FIGS. 10A and 10B, such that magnetic and electrical connections are created between the cartridge and the control device. In particular, FIG. 11 illustrates a partial cross-section view of the cartridge 900 coupled with the inner frame 1015 of the control device. In the depicted implementation, the angled surface 1060 of the inner frame 1015 is configured to complement the angled surface 960 of the metal ring 952 of the flange 950 of the cartridge 900. As such, when the cartridge 900 of the depicted implementation is coupled with the inner frame 1015 of the control device, a magnetic connection is created between the plurality of magnets 1052A, 1052B, 1052C, 1052D located in angled surface 1060 of the inner frame 1015 of the control device, and the metal ring 952 that comprises part of the flange 950 of the cartridge 900. In addition, when the cartridge 900 of the depicted implementation is coupled with the inner frame 1015, an electrical connection is created between the pair conductive pins 1020A, 102B of the inner frame 1015 of the control device and the conductive plugs of the cartridge 900. As such, when the cartridge 900 is received in the inner frame 1015 of the control device, the heater 920 of the cartridge 900 may be operatively connected to the battery of the control device. Thus, when the cartridge 900 of the depicted implementation is coupled with the inner frame 1015 of the control device, the cartridge 900 is mechanically biased into connection with the inner frame 1015 of the control device such that the electrical connection is maintained between the cartridge and the control device.

FIG. 12A illustrates an exploded partial perspective view of an inner frame of a control device according to an example implementation of the present disclosure. In particular, FIG. 12A illustrates an inner frame 1215 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 1215 of the depicted implementation includes a cartridge receiving chamber 1212 and a magnetic ring 1252 that defines an upper portion 1258 of the inner frame 1215. In the depicted implementation, the magnetic ring 1252 defines an angled surface 1260, which angles downward and inward with respect to a top edge thereof. In the depicted implementation, the magnetic ring 1252 is affixed to the inner frame 1215 via an adhesive, although in other implementations other methods of attachment of possible, including, for example, via an insert molding process. Reference is made to the possible magnet materials discussed above.

In addition, the inner frame 1215 of the depicted implementation also includes a pair of conductive pins 1220A, 1220B located in the inner frame 1215 and proximate the upper portion 1258 thereof. In the depicted implementation, the conductive pins 1220A, 1220B comprise spring-loaded pins (e.g., electrical pogo pins), each of which is biased inward such that a portion of the end of the pin extends into the cartridge receiving chamber 1212 and is configured to deflect outward against the force of an integral spring, although in other implementations other types of conductive elements may be used. In the depicted implementation, ends of the conductive pins 1220A, 1220B have a rounded profile, although other profiles are possible, such that deflection of the conductive pins 1220 is facilitated when a cartridge is inserted into the receiving chamber 1212. In the depicted implementation, the conductive pins 1220A, 1220B may be affixed inside the inner frame 1215 via a press-fit and/or adhesive connection, or via an insert molding process, such that the movable components of the conductive pins are able to deflect outward against the force of the springs. In the depicted implementation the conductive pins 1220A, 1220B are operatively connected to the battery of the control device in order, as will be discussed below, to provide power to the heater of an inserted cartridge. In various implementations, the conductive pins 1220A, 1220B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 12B illustrates a perspective view of a cartridge according to an example implementation of the present disclosure. In particular, FIG. 12B illustrates a cartridge 1100 that includes a tank 1102 that is defined by an outer tank wall 1104 that includes a proximal end 1106 and a distal end 1108, which is closed. In many aspects, the cartridge 1100 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 1100 of the depicted implementation includes a mouthpiece 1110 that is defined by an outer mouthpiece wall 1112 that includes a proximal end 1114 with an exit portal 1115 defined therein, and a distal end 1116 that engages the proximal end 1106 of the tank 1102. In the depicted implementation, the mouthpiece wall 1112 includes a flange 1150 positioned between the proximal end 1114 and the distal end 1116 thereof. In the depicted implementation, the flange 1150 of the cartridge 1100 also includes a metal ring 1152 that defines an angled surface 1160. In various implementations, the metal ring 1152 may comprise any material configured to be attracted by a magnet, such as various ferromagnetic materials, including, but not limited, to iron, nickel, cobalt, alloys such as steel, and/or any combination thereof.

The cartridge 1100 also includes a pair of conductive plugs 1125A, 1125B located on opposite sides of the mouthpiece 1110 and below the metal plate 1152 of the flange 1150. In the depicted implementation, the conductive plugs may be affixed inside the mouthpiece 1110 of the cartridge 1100 via an adhesive, although in other implementations other methods of attachment of possible, including, for example, via an insert molding process. In the depicted implementation, the conductive plugs 1125A, 1125B are operatively connected to a heater 1120 (see FIG. 13) of the cartridge 1100. In various implementations, the conductive plugs 1125A, 1125B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

In various implementations, a portion of the cartridge 1100 of FIG. 12B is configured to be coupled with the cartridge receiving chamber 1212 of the inner frame 1215 of FIG. 12A, such that magnetic and electrical connections are created between the cartridge and the control device. In particular, FIG. 13 illustrates a partial cross-section view of the cartridge 1100 coupled with the inner frame 1215 of the control device. In the depicted implementation, the angled surface 1260 of the magnetic ring 1252 of the inner frame 1215 is configured to complement the angled surface 1160 of the metal ring 1152 of the flange 1150 of the cartridge 1100, although in other implementations, the contact surfaces may be flat (e.g., thus creating substantially right angle interfaces between surfaces). As such, when the cartridge 1100 of the depicted implementation is coupled with the inner frame 1215 of the control device, a magnetic connection is created between the magnetic ring 1252 of the inner frame 1215 of the control device, and the metal ring 1152 that comprises part of the flange 1150 of the cartridge 1100. In addition, when the cartridge 1100 of the depicted implementation is coupled with the inner frame 1215, an electrical connection is created between the pair conductive pins 1220A, 1220B of the inner frame 1215 of the control device and the conductive plugs 1125A, 1125B of the cartridge 1100. As such, when the cartridge 1100 is received in the inner frame 1215 of the control device, the heater 1120 of the cartridge 1100 may be operatively connected to the battery of the control device. Thus, when the cartridge 1100 of the depicted implementation is coupled with the inner frame 1215 of the control device, the cartridge 1100 is mechanically biased into connection with the inner frame 1215 of the control device such that the electrical connection is maintained between the cartridge and the control device.

FIG. 14A illustrates a partial perspective view of an inner frame of a control device according to an example implementation of the present disclosure. In particular, FIG. 14A illustrates an inner frame 1415 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 1415 of the depicted implementation includes a cartridge receiving chamber 1412 and a pair of separate magnets 1452A, 1452B that define part of an upper portion 1458 of the inner frame 1415. In the depicted implementation, the upper portion 1458 of the inner frame 1415 (defined by the pair of separate magnets 1452A, 1452B and portions of the inner frame 1415 between the magnets 1452A, 1452B) defines an angled surface 1460, which angles downward and inward with respect to a top edge. In the depicted implementation, the separate magnets 1452A, 1452B have an arc shape and are affixed to the inner frame 1415 via an adhesive, although in other implementations other methods of attachment of possible, including, for example, via an insert molding process. In the depicted implementation the separate magnets 1452A, 1452B are operatively connected to the battery of the control device in order, as will be discussed below, to provide power to the heater of an inserted cartridge. Reference is made to the possible magnet materials discussed above.

FIG. 14B illustrates a perspective view of a cartridge according to an example implementation of the present disclosure, and FIG. 14C illustrates a partial transparent perspective view of a cartridge according to an example implementation of the present disclosure. In particular, FIGS. 14B and 14C illustrate a cartridge 1300 that includes a tank 1302 that is defined by an outer tank wall 1304 that includes a proximal end 1306 and a distal end 1308, which is closed. In many aspects, the cartridge 1300 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 1300 of the depicted implementation includes a mouthpiece 1310 that is defined by an outer mouthpiece wall 1312 that includes a proximal end 1314 with an exit portal 1315 defined therein, and a distal end 1316 that engages the proximal end 1306 of the tank 1302. In the depicted implementation, the mouthpiece wall 1312 includes a flange 1350 positioned between the proximal end 1314 and the distal end 1316 thereof. In the depicted implementation, the flange 1350 of the cartridge 1300 includes a pair of separate metal plates 1352A, 1352B. In the depicted implementation, the pair of separate metal plates 1352A, 1352B and portions of the flange 1350 between the metal plates 1352A, 1352B define an angled surface 1360, which angles downward and inward. In the depicted implementation, the separate metal plates 1352A, 1352B have an arrow head shape and are affixed to the flange 1350 of the cartridge 1300 via an adhesive or an insert molding process, although other methods of attachment of possible. In the depicted implementation, the separate metal plates 1352A, 1352B are operatively connected to a heater 1320 (see FIGS. 14C and 15) of the cartridge 1300. In various implementations, the metal plates 1352A, 1352B may comprise any material configured to be electrically conductive and attracted by a magnet, such as various ferromagnetic materials, including, but not limited, to iron, nickel, cobalt, alloys such as steel, and/or any combination thereof.

In various implementations, a portion of the cartridge 1300 of FIGS. 14B and 14C is configured to be coupled with the cartridge receiving chamber 1412 of the inner frame 1415 of FIG. 14A, such that magnetic and electrical connections are created between the cartridge and the control device. In particular, FIG. 15 illustrates a partial cross-section view of the cartridge 1300 coupled with the inner frame 1415 of the control device. In the depicted implementation, the angled surface 1460 of the separate magnets 1452A, 1452B and the portions of the inner frame 1415 is configured to complement the angled surface 1360 of the separate metal plates 1352A, 1352B and the portions of the flange 1350 of the cartridge 1300, although in other implementations, the contact surfaces may be flat (e.g., thus creating substantially right angle interfaces between surfaces). As such, when the cartridge 1300 of the depicted implementation is coupled with the inner frame 1415 of the control device, magnetic and electrical connections are created between the separate magnets 1452A, 1452B of the inner frame 1415 of the control device, and the separate metal plates 1352A, 1352B that comprise part of the flange 1350 of the cartridge 1300. As such, when the cartridge 1300 is received in the inner frame 1415 of the control device, the heater 1320 of the cartridge 1300 may be operatively connected to the battery of the control device. Thus, when the cartridge 1300 of the depicted implementation is coupled with the inner frame 1415 of the control device, the cartridge 13200 is mechanically biased into connection with the inner frame 1415 of the control device such that the electrical connection is maintained between the cartridge and the control device.

FIG. 16A illustrates a partial perspective view of an inner frame of a control device according to an example implementation of the present disclosure, and FIG. 16B illustrates a top view of an inner frame of a control device according to an example implementation of the present disclosure. In particular, FIGS. 16A and 16B illustrate a portion of an inner frame 1615 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 1615 of the depicted implementation includes a cartridge receiving chamber 1612 and an upper portion 1658 defined at the upper end of the inner frame 1615. The inner frame 1615 of the depicted implementation also includes a plurality of magnets 1652 located proximate the upper portion 1658. In the depicted implementation, there are four individual magnets 1652A, 1652B, 1652C, 1652D, each of which has a substantially spherical shape, although in other implementation more or less individual magnets may be used and the magnets may have different shapes and/or sizes. Reference is made to the possible magnet materials discussed above. In the depicted implementation, the magnets 1652A, 1652B, 1652C, 1652D are spaced around the outside of the inner frame 1615 and proximate the upper portion 1658 thereof, with each of the plurality of magnets being located inside a corresponding magnet receiving feature 1653. In the depicted implementation, each magnet receiving feature 1653 comprises a compartment within which a respective magnet 1652 is trapped. Each magnet receiving feature 1653 further defines an opening 1654, which extends into the cartridge receiving chamber 1612. In various implementations, the magnets 1652A, 1652B, 1652C, 1652D are configured to move within the receiving features 1653 such that, in one direction, at least a portion of each magnet 1652 is configured to extend through a respective opening 1654, and in an opposite direction, each magnet may move away from the opening 1654.

In addition, the inner frame 1615 of the depicted implementation also includes a pair of conductive pins 1620A, 1620B located in the inner frame 1615 and proximate the upper portion 1658 thereof. In the depicted implementation, the conductive pins 1620A, 1620B comprise spring-loaded pins (e.g., electrical pogo pins), each of which is biased inward such that a portion of the end of the pin extends into the cartridge receiving chamber 1612 and is configured to deflect outward against the force of an integral spring, although in other implementations other types of conductive elements may be used. In the depicted implementation, ends of the conductive pins 1620A, 1620B have a rounded profile, although other profiles are possible, such that deflection of the conductive pins 1620A, 1620B is facilitated when a cartridge is inserted into the receiving chamber 1612. In the depicted implementation, the conductive pins 1620A, 1620B may be affixed inside the inner frame 1615 via a press-fit and/or adhesive connection, or via an insert molding process, such that the movable components of the conductive pins are able to deflect outward against the force of the springs. In the depicted implementation the conductive pins 1620A, 1620B are operatively connected to the battery of the control device in order, as will be discussed below, to provide power to the heater of an inserted cartridge. In various implementations, the conductive pins 1620A, 1620B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 16C illustrates a perspective view of a cartridge according to an example implementation of the present disclosure. In particular, FIG. 16C illustrates a cartridge 1500 that includes a tank 1502 that is defined by an outer tank wall 1504 that includes a proximal end 1506 and a distal end 1508, which is closed. In many aspects, the cartridge 1500 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 1500 of the depicted implementation includes a mouthpiece 1510 that is defined by an outer mouthpiece wall 1512 that includes a proximal end 1514 with an exit portal 1515 defined therein, and a distal end 1516 that engages the proximal end 1506 of the tank 1502. In the depicted implementation, the mouthpiece wall 1512 includes a flange 1550 positioned between the proximal end 1514 and the distal end 1516 thereof. The cartridge 1500 of the depicted implementation also includes a pair of metal plates 1552A, 1552B, each of which is disposed below the flange 1550 and on opposite sides of the mouthpiece 1510. In the depicted implementation, the metal plates 1552A, 1552B are affixed to the mouthpiece 1510 via an adhesive or an insert molding process, although in other implementations other methods of attachment are possible. In the depicted implementation, each of the metal plates 1552A, 1552B includes a pair of detents 1555 located on opposite ends thereof. In various implementations, the detents 1555 are configured to receive a portion of the spherical magnets 1652 of the cartridge 1600. In the depicted implementation, the metal plates 1552 are also operatively connected to a heater 1520 (see FIG. 5) of the cartridge 1500. In various implementations, the metal plates 1552A, 1552B may comprise any material configured to be electrically conductive and attracted by a magnet, such as various ferromagnetic materials, including, but not limited, to iron, nickel, cobalt, alloys such as steel, and/or any combination thereof.

In various implementations, a portion of the cartridge 1500 of FIG. 16C is configured to be coupled with the cartridge receiving chamber 1612 of the inner frame 1615 of FIGS. 16A and 16B, such that magnetic and electrical connections are created between the cartridge and the control device. In particular, FIG. 17 illustrates a partial cross-section view of the cartridge 1500 coupled with the inner frame 1615 of the control device. As illustrated in the figure, when the cartridge 1500 of the depicted implementation is coupled with the inner frame 1615 of the control device, a magnetic connection is created between the plurality of magnets 1652 located in the inner frame 1615 of the control device and the metal plates 1652 of the cartridge. In particular, when the cartridge 1500 is coupled with the inner frame 1615 of the control device, the plurality of magnets 1652 locate within respective detents 1555 of the metal plates 1552A, 1552B. In addition, when the cartridge 1500 of the depicted implementation is coupled with the inner frame 1615, an electrical connection is created between the pair conductive pins 1620A, 1620B of the inner frame 1615 of the control device and the metal plates 1552A, 1552B of the cartridge 1500. As such, when the cartridge 1500 is received in the inner frame 1615 of the control device, the heater 1520 of the cartridge 1500 may be operatively connected to the battery of the control device. Thus, when the cartridge 1500 of the depicted implementation is coupled with the inner frame 1615 of the control device, the cartridge 1500 is mechanically biased into connection with the inner frame 1615 of the control device such that the electrical connection is maintained between the cartridge and the control device.

FIG. 18A illustrates a partial perspective view of an inner frame of a control device according to an example implementation of the present disclosure. In particular, FIG. 18A illustrates a portion of an inner frame 1815 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 1815 of the depicted implementation includes a cartridge receiving chamber 1812 that defines an upper portion 1858 thereof. The inner frame 1815 of the depicted implementation also includes a pair of magnets 1852A, 1852B located in the outer wall of the control device and above the upper portion 1858 of the inner frame 1815. In the depicted implementation, the magnets 1852A, 1852B are located on opposite sides of the control device and each magnet 1852 has a wedge shape that defines an undercut surface 1857. In the depicted implementation, the magnets 1852A, 1852B may be affixed to the control device via an adhesive, although in other implementations other methods of attachment are possible, including, for example, via an insert molding process. Reference is made to the possible magnet materials discussed above.

In addition, the inner frame 1815 of the depicted implementation also includes a pair of conductive pins 1820A, 1820B located in the inner frame 1815 proximate the upper portion 1858 thereof. In the depicted implementation, the conductive pins 1820A, 1820B comprise spring-loaded pins (e.g., electrical pogo pins), each of which is biased inward such that a portion of the end of the pin extends into the cartridge receiving chamber 1812 and is configured to deflect outward against the force of an integral spring, although in other implementations other types of conductive elements may be used. In the depicted implementation, ends of the conductive pins 1820A, 1820B have a rounded profile, although other profiles are possible, such that deflection of the conductive pins 1820A, 1820B is facilitated when a cartridge is inserted into the receiving chamber 1812. In the depicted implementation, the conductive pins 1820A, 1820B may be affixed inside the inner frame 1815 via a press-fit and/or adhesive connection, or via an insert molding process, such that the movable components of the conductive pins are able to deflect outward against the force of the springs. In the depicted implementation the conductive pins 1820A, 1820B are operatively connected to the battery of the control device in order, as will be discussed below, to provide power to the heater of an inserted cartridge. In various implementations, the conductive pins 1820A, 1820B may be constructed of any electrically conductive material, including, for example, but not limited to, copper, aluminum, platinum, gold, silver, iron, steel, brass, bronze, graphite, conductive ceramic materials, and/or any combination thereof.

FIG. 18B illustrates a perspective view of a cartridge according to an example implementation of the present disclosure. In particular, FIG. 18B illustrates a cartridge 1700 that includes a tank 1702 that is defined by an outer tank wall 1704 that includes a proximal end 1706 and a distal end 1708, which is closed. In many aspects, the cartridge 1700 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 1700 of the depicted implementation includes a mouthpiece 1710 that is defined by an outer mouthpiece wall 1712 that includes a proximal end 1714 with an exit portal 1715 defined therein, and a distal end 1716 that engages the proximal end 1706 of the tank 1702. In the depicted implementation, the mouthpiece wall 1712 includes a flange 1750 positioned between the proximal end 1714 and the distal end 1716 thereof. The cartridge 1700 of the depicted implementation also includes a pair of sliding metal plates 1752A, 1752B, which are disposed in the flange 1750. In the depicted implementation, each of the metal plates 1752 has a pointed structure that defines a peak area 1759 and is configured to slide outward with the force of a spring and inward against the force of the spring. The extent to which the metal plates 1752A, 1752B extend outward is limited by the structure of the flange 1750. The cartridge 1700 also includes a pair of conductive plugs 1725A, 1725B located on opposite sides of the mouthpiece 1710 and below the flange 1750 and metal plates 1752A, 1752B. In the depicted implementation, the conductive plugs 1725A, 1725B may be affixed inside the mouthpiece 1710 of the cartridge 1700 via an adhesive, although in other implementations other methods of attachment of possible, including, for example, via an insert molding process. In the depicted implementation, the conductive plugs 1725A, 1725B are operatively connected to a heater 1720 (see FIGS. 19A and 19B) of the cartridge 1700. As noted above, in various implementations, the conductive plugs 1725A, 1725B may be constructed of any electrically conductive material, including, for example, copper, beryllium copper, aluminum, platinum, gold, silver, iron, steel, brass, bronze, graphite, conductive ceramic materials, and/or any combination thereof. In various implementations, the metal plates 1752A, 1752B may comprise any material configured to be attracted by a magnet, such as various ferromagnetic materials, including, but not limited, to iron, nickel, cobalt, alloys such as steel, and/or any combination thereof. In various implementations, the conductive plugs 1725A, 1725B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

In various implementations, a portion of the cartridge 1700 of FIG. 18B is configured to be coupled with the cartridge receiving chamber 1812 of the inner frame 1815 of FIG. 18A, such that magnetic and electrical connections are created between the cartridge and the control device. In particular, FIG. 19A illustrates a partial cross-section view of the cartridge 1700 prior to being fully coupled with the inner frame 1815 of the control device, and FIG. 19B illustrates a partial cross-section view of the cartridge 1700 after being coupled with the inner frame 1815 of the control device. As the cartridge 1700 is inserted into the inner frame 1815 of the control device, the pointed sliding metal plates first deflect inward until the peak areas 1759 of the metal plates 1752A, 1752B pass the top edge of the control device magnets 1852A, 1852B at which point the sliding metal plates 1752A, 1752B extend outward against the undercut surface 1857 of the magnets 1852A, 1852B until the cartridge is received in inner frame 1815. As also illustrated in the figures, when the cartridge 1700 of the depicted implementation is coupled with the inner frame 1815 of the control device, a magnetic connection is created between the pair of magnets 1857 located in the control device and the pair of sliding metal plates 1752A, 1752B of the cartridge. In addition, when the cartridge 1700 of the depicted implementation is coupled with the inner frame 1815, an electrical connection is created between the pair conductive pins 1820A, 1820B of the inner frame 1815 of the control device and the conductive plugs 1725A, 1725B of the cartridge 1700. As such, when the cartridge 1700 is received in the inner frame 1815 of the control device, the heater 1720 of the cartridge 1700 may be operatively connected to the battery of the control device. Therefore, when the cartridge 1700 of the depicted implementation is coupled with the inner frame 1815 of the control device, the cartridge 1700 is mechanically biased into connection with the inner frame 1815 of the control device such that the electrical connection is maintained between the cartridge and the control device.

FIG. 20A illustrates a partial transparent perspective view of an inner frame of a control device according to an example implementation of the present disclosure, and FIG. 20B illustrates a partial perspective view of an inner frame of a control device according to an example implementation of the present disclosure. In particular, FIGS. 20A and 20B illustrate a portion of an inner frame 2015 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 2015 of the depicted implementation includes a cartridge receiving chamber 2012 and an upper flange 2050. The inner frame 2015 of the depicted implementation also includes a plurality of magnets 2052 located proximate the upper flange 2050 of the inner frame 2015. In particular, the depicted implementation includes two pairs of cylindrical magnets 2052A, 2052B, 2052C, 2052D each pair located on opposite sides of the inner frame 2015 and extending proximate the upper flange 2050 thereof, with each of the plurality of magnets being located inside a corresponding magnet receiving feature 2053, which, in the depicted implementation, is an extension of the upper flange 2050. Reference is made to the possible magnet materials discussed above. Although other methods are possible, the magnets 2052A, 2052B, 2052C, 2052D of the depicted implementation may be affixed inside the magnet receiving features 2053 via a press-fit and/or adhesive connection, or via an insert molding process.

In addition, the inner frame 2015 of the depicted implementation also includes a pair of conductive pins 2020A, 2020B located in the inner frame 2015 and below the upper flange 2050 thereof. In the depicted implementation, the conductive pins 2020A, 2020B comprise spring-loaded pins (e.g., electrical pogo pins), each of which is biased inward such that a portion of the end of the pin extends into the cartridge receiving chamber 2012 and is configured to deflect outward against the force of an integral spring, although in other implementations other types of conductive elements may be used. In the depicted implementation, ends of the conductive pins 2020A, 2020B have a rounded profile, although other profiles are possible, such that deflection of the conductive pins 2020A, 2020B is facilitated when a cartridge is inserted into the receiving chamber 2012. In the depicted implementation, the conductive pins 2020A, 202B may be affixed inside the inner frame 2015 via a press-fit and/or adhesive connection, or via an insert molding process, such that the movable components of the conductive pins are able to deflect outward against the force of the springs. In the depicted implementation the conductive pins 2020A, 2020B are operatively connected to the battery of the control device in order, as will be discussed below, to provide power to the heater of an inserted cartridge. In various implementations, the conductive pins 2020A, 2020B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 20C illustrates a perspective view of a cartridge according to an example implementation of the present disclosure. In particular, FIG. 20C illustrates a cartridge 1900 that includes a tank 1902 that is defined by an outer tank wall 1904 that includes a proximal end 1906 and a distal end 1908, which is closed. In many aspects, the cartridge 1900 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 1900 of the depicted implementation includes a mouthpiece 1910 that is defined by an outer mouthpiece wall 1912 that includes a proximal end 1914 with an exit portal 1915 defined therein, and a distal end 1916 that engages the proximal end 1906 of the tank 1902. In the depicted implementation, the mouthpiece wall 1912 includes a flange 1950 positioned between the proximal end 1914 and the distal end 1916 thereof. The cartridge 1900 of the depicted implementation also includes a metal plate 1952, which is disposed below the flange 1950. In the depicted implementation, the metal plate 1952 is affixed to the bottom of the flange 1950 of the mouthpiece 1910 via an adhesive, although in other implementations other methods of attachment of possible, including, for example, via an insert molding process. The cartridge 1900 also includes a pair of conductive plugs 1925A, 1925B located on opposite sides of the mouthpiece 1910 and below the flange 1950 and metal plate 1952. In the depicted implementation, the conductive plugs may be affixed inside the mouthpiece 1910 of the cartridge 1900 via an adhesive, although in other implementations other methods of attachment of possible, including, for example, via an insert molding process. In the depicted implementation, the conductive plugs 1925A, 1925B are operatively connected to a heater 1920 (see FIG. 21) of the cartridge 1900. In various implementations, the conductive plugs may be constructed of any electrically conductive material, including, for example, but not limited to, copper, beryllium copper, aluminum, platinum, gold, silver, iron, steel, brass, bronze, graphite, conductive ceramic materials, and/or any combination thereof. In various implementations, the metal plate 1952 may comprise any material configured to be attracted by a magnet, such as various ferromagnetic materials, including, but not limited, to iron, nickel, cobalt, alloys such as steel, and/or any combination thereof. In various implementations, the conductive plugs 1925A, 1925B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

In various implementations, a portion of the cartridge 1900 of FIG. 20C is configured to be coupled with the cartridge receiving chamber 2012 of the inner frame 2015 of FIGS. 20A and 2B, such that magnetic and electrical connections are created between the cartridge and the control device. In particular, FIG. 21 illustrates a partial cross-section view of the cartridge 1900 coupled with the inner frame 2015 of the control device. As illustrated in the figure, when the cartridge 1900 of the depicted implementation is coupled with the inner frame 2015 of the control device, a magnetic connection is created between the plurality of magnets 2052A, 2052B, 2052C, 2052D located in the inner frame 2015 of the control device and the metal plate 1952 of the cartridge 1900. In addition, when the cartridge 1900 of the depicted implementation is coupled with the inner frame 2015, an electrical connection is created between the pair conductive pins 2020A, 2020B of the inner frame 2015 of the control device and the conductive plugs 1925A, 1925B of the cartridge 1900. As such, when the cartridge 1900 is received in the inner frame 2015 of the control device, the heater 1920 of the cartridge 1900 may be operatively connected to the battery of the control device. Therefore, when the cartridge 1900 of the depicted implementation is coupled with the inner frame 2015 of the control device, the cartridge 1900 is mechanically biased into connection with the inner frame 2015 of the control device such that the electrical connection is maintained between the cartridge and the control device.

FIG. 22A illustrates a partial transparent perspective view of an inner frame of a control device according to an example implementation of the present disclosure, and FIG. 22B illustrates a partial perspective view of an inner frame of a control device according to an example implementation of the present disclosure. In particular, FIGS. 22A and 22B illustrate a portion of an inner frame 2215 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 2215 of the depicted implementation includes a cartridge receiving chamber 2212 and an upper flange 2250. The inner frame 2215 of the depicted implementation also includes a plurality of magnets 2252 located proximate the upper flange 2250 of the inner frame 2215. In particular, the depicted implementation includes two pairs of cylindrical magnets 2252A, 2252B, 2252C, 2252D, each pair located on opposite sides of the inner frame 2215 and extending proximate the upper flange 2250 thereof, with each of the plurality of magnets being located inside a corresponding magnet receiving feature 2253, which, in the depicted implementation, is an extension of the upper flange 2250. Reference is made to the possible magnet materials discussed above. Although other methods are possible, the magnets 2252A, 2252B, 2252C, 2252D of the depicted implementation may be affixed inside the magnet receiving features 2253 via a press-fit and/or adhesive connection, or via an insert molding process.

In addition, the inner frame 2215 of the depicted implementation also includes a pair of conductive pins 2220A, 2220B located in the inner frame 2215 and proximate the upper flange 2250 thereof. In the depicted implementation, the conductive pins 2220A, 2220B comprise spring-loaded pins (e.g., electrical pogo pins), each of which is biased upward such that a portion of the end of the pin extends through the upper flange 2250 and is configured to deflect downward against the force of an integral spring, although in other implementations other types of conductive elements may be used. In the depicted implementation, ends of the conductive pins 2220A, 2220B have a rounded profile, although other profiles are possible. In the depicted implementation, the conductive pins 2220A, 2220B may be affixed inside the inner frame 2015 via a press-fit and/or adhesive connection, or via an insert molding process, such that the movable components of the conductive pins are able to deflect upward against the force of the springs. In the depicted implementation the conductive pins 2220A, 2220B are operatively connected to the battery of the control device in order, as will be discussed below, to provide power to the heater of an inserted cartridge. In various implementations, the conductive pins 2220A, 2220B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 22C illustrates a perspective view of a cartridge according to an example implementation of the present disclosure. In particular, FIG. 22C illustrates a cartridge 2100 that includes a tank 2102 that is defined by an outer tank wall 2104 that includes a proximal end 2106 and a distal end 2108, which is closed. In many aspects, the cartridge 2100 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 2100 of the depicted implementation includes a mouthpiece 2110 that is defined by an outer mouthpiece wall 2112 that includes a proximal end 2114 with an exit portal 2115 defined therein, and a distal end 2116 that engages the proximal end 2106 of the tank 2102. In the depicted implementation, the mouthpiece wall 2112 includes a flange 2150 positioned between the proximal end 2114 and the distal end 2116 thereof. The cartridge 2100 of the depicted implementation also includes a pair of separate metal plates 2152A, 2152B which comprise part of the flange 2150. In the depicted implementation, the metal plates 2152A, 2152B are affixed to the flange 2150 of the mouthpiece 2110 via an adhesive, although in other implementations other methods of attachment of possible, including, for example, via an insert molding process. In the depicted implementation, the separate metal plates 2152A, 2152B are operatively connected to a heater 2120 (see FIG. 23) of the cartridge 2100. In various implementations, the metal plates may 2152A, 2152B comprise any material configured to be electrically conductive and attracted by a magnet, such as various ferromagnetic materials, including, but not limited, to iron, nickel, cobalt, alloys such as steel, and/or any combination thereof.

In various implementations, a portion of the cartridge 2100 of FIG. 22C is configured to be coupled with the cartridge receiving chamber 2212 of the inner frame 2215 of FIGS. 22A and 22B, such that magnetic and electrical connections are created between the cartridge and the control device. In particular, FIG. 23 illustrates a partial cross-section view of the cartridge 2100 coupled with the inner frame 2215 of the control device. As illustrated in the figure, when the cartridge 2100 of the depicted implementation is coupled with the inner frame 2215 of the control device, a magnetic connection is created between the plurality of magnets 2252A, 2252B, 2252C, 2252D located in the inner frame 2215 of the control device and the metal plates 2152A, 2152B of the cartridge 2100. In addition, when the cartridge 2100 of the depicted implementation is coupled with the inner frame 2215, an electrical connection is created between the pair conductive pins 2220A, 2220B of the inner frame 2215 of the control device and the metal plates 2152A, 2152B of the cartridge 2100. As such, when the cartridge 2100 is received in the inner frame 2215 of the control device, the heater 2120 of the cartridge 2100 may be operatively connected to the battery of the control device. Thus, when the cartridge 2100 of the depicted implementation is coupled with the inner frame 2215 of the control device, the cartridge 2100 is mechanically biased into connection with the inner frame 2215 of the control device such that the electrical connection is maintained between the cartridge and the control device.

FIG. 24A illustrates a partial perspective view of an inner frame of a control device according to an example implementation of the present disclosure. In particular, FIG. 24A illustrates a portion of an inner frame 2415 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 2415 of the depicted implementation includes a cartridge receiving chamber 2412 and an upper flange 2450. The inner frame 2415 of the depicted implementation also includes a pair of magnets 2452A, 2452B located proximate the upper flange 2450 of the inner frame 2415. In particular, the depicted implementation includes two cylindrical magnets 2452A, 2452B located on opposite sides of the inner frame 2415 and extending through the upper flange 2450 thereof. Reference is made to the possible magnet materials discussed above. Although other configurations are possible, in the depicted implementation, the top surfaces of the magnets 2452A, 2452B are substantially flush with the top surface of the upper flange 2450. In the depicted implementation, each of the magnets is located inside a corresponding magnet receiving feature 2453, which, in the depicted implementation, is an extension of the upper flange 2450. Although other methods are possible, the magnets 2452A, 2452B of the depicted implementation may be affixed inside the magnet receiving features 2453 via a press-fit and/or adhesive connection, or via an insert molding process. Although not shown in the figure, in the depicted implementation the magnets 2452A, 2452B are operatively connected to the battery of the control device.

FIG. 24B illustrates a perspective view of a cartridge according to an example implementation of the present disclosure. In particular, FIG. 24B illustrates a cartridge 2300 that includes a tank 2302 that is defined by an outer tank wall 2304 that includes a proximal end 2306 and a distal end 2308, which is closed. In many aspects, the cartridge 2300 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 2300 of the depicted implementation includes a mouthpiece 2310 that is defined by an outer mouthpiece wall 2312 that includes a proximal end 2314 with an exit portal 2315 defined therein, and a distal end 2316 that engages the proximal end 2306 of the tank 2302. In the depicted implementation, the mouthpiece wall 2312 includes a flange 2350 positioned between the proximal end 2314 and the distal end 2316 thereof. The cartridge 2300 of the depicted implementation also includes a pair of separate metal plates 2352A, 2352B which comprise part of the flange 2350. In the depicted implementation, the metal plates 2352A, 2352B are affixed to the flange 2350 of the mouthpiece 230 via an adhesive, although in other implementations other methods of attachment of possible, including, for example, via an insert molding process. In the depicted implementation, the separate metal plates 2352A, 2352B are operatively connected to a heater 2320 (see FIG. 23) of the cartridge 2300. In various implementations, the metal plates 2352A, 2352B may comprise any material configured to be electrically conductive and attracted by a magnet, such as various ferromagnetic materials, including, but not limited, to iron, nickel, cobalt, alloys such as steel, and/or any combination thereof.

In various implementations, a portion of the cartridge 2300 of FIG. 24B is configured to be coupled with the cartridge receiving chamber 2412 of the inner frame 2415 of FIG. 24A, such that magnetic and electrical connections are created between the cartridge and the control device. In particular, FIG. 25 illustrates a partial cross-section view of the cartridge 2300 coupled with the inner frame 2415 of the control device. As illustrated in the figure, when the cartridge 2300 of the depicted implementation is coupled with the inner frame 2415 of the control device, a magnetic connection is created between the pair of magnets 2452A, 2452B located in the inner frame 2415 of the control device and the metal plates 2352A, 2352B of the cartridge 2300. In addition, when the cartridge 2300 of the depicted implementation is coupled with the inner frame 2415, an electrical connection is created between the pair magnets 2452A, 2452B of the inner frame 2415 of the control device and the metal plates 2352A, 2352B of the cartridge 2300. As such, when the cartridge 2300 is received in the inner frame 2415 of the control device, the heater 2320 of the cartridge 2300 may be operatively connected to the battery of the control device. Therefore, when the cartridge 2300 of the depicted implementation is coupled with the inner frame 2415 of the control device, the cartridge 2300 is mechanically biased into connection with the inner frame 2415 of the control device such that the electrical connection is maintained between the cartridge and the control device.

FIG. 26A illustrates a partial perspective view of an inner frame of a control device according to an example implementation of the present disclosure. In particular, FIG. 26A illustrates a portion of an inner frame 2615 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 2615 of the depicted implementation includes a cartridge receiving chamber 2612 and an upper flange 2650. The inner frame 2615 of the depicted implementation also includes a pair of magnets 2652A, 2652B located proximate the upper flange 2650 of the inner frame 2615. In particular, the depicted implementation includes two cylindrical magnets 2652A, 2652B located on opposite sides of the inner frame 2615, with each of the magnets 2652A, 2652B being located inside a corresponding conductive casing 2620A, 2620B, which each magnet/casing (2652A, 2620A, 2652B, 2620B) assembly extending through the upper flange 2650 thereof. Reference is made to the possible magnet materials discussed above. In addition, each of the conductive casings 2620A, 2620B and magnets 2652 is located inside of a corresponding receiving feature 2653. Although other methods are possible, the magnets 2652 of the depicted implementation may be affixed inside the conductive casings 2620A, 2620B via an adhesive and/or press-fit connection, and the conductive casings 2620A, 2620B (or the conductive casing and magnet assemblies (2620A, 2652A, 2620B, 2652B)) of the depicted implementation may be affixed inside the receiving features 2653 via a press-fit and/or adhesive connection, or via an insert molding process. Although not shown in the figure, the conductive casings 2620A, 2620B are operatively connected to the battery of the control device. In various implementations, the conductive casings 2620A, 2620B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 26B illustrates a perspective view of a cartridge according to an example implementation of the present disclosure. In particular, FIG. 26B illustrates a cartridge 2500 that includes a tank 2502 that is defined by an outer tank wall 2504 that includes a proximal end 2506 and a distal end 2508, which is closed. In many aspects, the cartridge 2500 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 2500 of the depicted implementation includes a mouthpiece 2510 that is defined by an outer mouthpiece wall 2512 that includes a proximal end 2514 with an exit portal 2515 defined therein, and a distal end 2516 that engages the proximal end 2506 of the tank 2502. In the depicted implementation, the mouthpiece wall 2512 includes a flange 2550 positioned between the proximal end 2514 and the distal end 2516 thereof. The cartridge 2500 of the depicted implementation also includes a pair of separate metal plates 2552A, 2552B which comprise part of the flange 2550. In the depicted implementation, the metal plates 2552A, 2552B are affixed to the flange 2550 of the mouthpiece 2510 via an adhesive, although in other implementations other methods of attachment of possible, including, for example, via an insert molding process. In the depicted implementation, the separate metal plates 2552A, 2552B are operatively connected to a heater 2520 (see FIG.

27) of the cartridge 2500. In various implementations, the metal plates 2552A, 2552B may comprise any material configured to be electrically conductive and attracted by a magnet, such as various ferromagnetic materials, including, but not limited to, iron, nickel, cobalt, alloys such as steel, and/or any combination thereof.

In various implementations, a portion of the cartridge 2500 of FIG. 26B is configured to be coupled with the cartridge receiving chamber 2612 of the inner frame 2615 of FIG. 26A, such that magnetic and electrical connections are created between the cartridge and the control device. In particular, FIG. 27 illustrates a partial cross-section view of the cartridge 2500 coupled with the inner frame 2615 of the control device. As illustrated in the figure, when the cartridge 2500 of the depicted implementation is coupled with the inner frame 2615 of the control device, a direct magnetic connection is created between the pair of magnets 2652 located in the inner frame 2615 of the control device and the metal plates 2552A, 2552B of the cartridge 2500. In addition, when the cartridge 2500 of the depicted implementation is coupled with the inner frame 2615, an electrical connection is created between the conductive casings 2620A, 2620B of the inner frame 2615 of the control device and the metal plates 2552A, 2552B of the cartridge 2500. As such, when the cartridge 2500 is received in the inner frame 2615 of the control device, the heater 2520 of the cartridge 2500 may be operatively connected to the battery of the control device. Therefore, when the cartridge 2500 of the depicted implementation is coupled with the inner frame 2615 of the control device, the cartridge 2500 is mechanically biased into connection with the inner frame 2615 of the control device such that the electrical connection is maintained between the cartridge and the control device.

FIG. 28A illustrates an exploded partial perspective view of an inner frame of a control device according to an example implementation of the present disclosure. In particular, FIG. 268 illustrates a portion of an inner frame 2815 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 2815 of the depicted implementation includes a cartridge receiving chamber 2812 and an upper flange 2850. The inner frame 2815 of the depicted implementation also includes a pair of magnets 2852A, 2852B located proximate the upper flange 2850 of the inner frame 2615. In particular, the depicted implementation includes two cylindrical magnets 2852A, 2852B located on opposite sides of the inner frame 2815, with respective top an side surfaces of each magnet 2852A, 2852B being substantially surrounded by a corresponding conductive casing 2820A, 2820B, which each magnet/casing (2852A, 2820A, 2852B, 2820B) assembly extending through the upper flange 2850 thereof. Reference is made to the possible magnet materials discussed above. Although other configurations are possible, in the depicted implementation, the top surfaces of the conductive casings 2820A, 2820B are substantially flush with the top surface of the upper flange 2850. In addition, each of the conductive casings 2820 and magnets 2852 is located inside of a corresponding receiving feature 2853, which in the depicted implementation is an extension of the flange. Although other methods are possible, the magnets 2852A, 2852B of the depicted implementation may be affixed inside the conductive casings 2820A, 2820B via an adhesive and/or press-fit connection, and the conductive casings 2820A, 2820B (or the conductive casing and magnet assemblies (2820, 2852)) of the depicted implementation may be affixed inside the receiving features 2853 via a press-fit and/or adhesive connection, or via an insert molding process. Although not shown in the figure, the conductive casings 2820A, 2820B are operatively connected to the battery of the control device. In various implementations, the conductive casings 2820A, 2820B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 28B illustrates a perspective view of a cartridge according to an example implementation of the present disclosure. In particular, FIG. 28B illustrates a cartridge 2700 that includes a tank 2702 that is defined by an outer tank wall 2704 that includes a proximal end 2706 and a distal end 2708, which is closed. In many aspects, the cartridge 2700 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 2700 of the depicted implementation includes a mouthpiece 2710 that is defined by an outer mouthpiece wall 2712 that includes a proximal end 2714 with an exit portal 2715 defined therein, and a distal end 2716 that engages the proximal end 2706 of the tank 2702. In the depicted implementation, the mouthpiece wall 2712 includes a flange 2750 positioned between the proximal end 2714 and the distal end 2716 thereof. The cartridge 2700 of the depicted implementation also includes a pair of separate metal plates 2752A, 2752B which comprise part of the flange 2750. In the depicted implementation, the metal plates 2752A, 2752B are affixed to the flange 2750 of the mouthpiece 2710 via an adhesive, although in other implementations other methods of attachment of possible, including, for example, via an insert molding process. In the depicted implementation, the separate metal plates 2752A, 2752B are operatively connected to a heater 2720 (see FIG. 29) of the cartridge 2700. In various implementations, the metal plates 2752A, 2752B may comprise any material configured to be electrically conductive and attracted by a magnet, such as various ferromagnetic materials, including, but not limited to, iron, nickel, cobalt, alloys such as steel, and/or any combination thereof.

In various implementations, a portion of the cartridge 2700 of FIG. 28B is configured to be coupled with the cartridge receiving chamber 2812 of the inner frame 2813 of FIG. 28A, such that magnetic and electrical connections are created between the cartridge and the control device. In particular, FIG. 29 illustrates a partial cross-section view of the cartridge 2700 coupled with the inner frame 2815 of the control device. As illustrated in the figure, when the cartridge 2700 of the depicted implementation is coupled with the inner frame 2813 of the control device, a magnetic connection is created between the pair of magnets 2852A, 2852B located in the inner frame 2815 of the control device and the metal plates 2752A, 2752B of the cartridge 2700. In addition, when the cartridge 2700 of the depicted implementation is coupled with the inner frame 2815, an electrical connection is created between the conductive casings 2820A, 2820B of the inner frame 2815 of the control device and the metal plates 2752A, 2752B of the cartridge 2700. As such, when the cartridge 2700 is received in the inner frame 2815 of the control device, the heater 2720 of the cartridge 2700 may be operatively connected to the battery of the control device. Therefore, when the cartridge 2700 of the depicted implementation is coupled with the inner frame 2815 of the control device, the cartridge 2700 is mechanically biased into connection with the inner frame 2815 of the control device such that the electrical connection is maintained between the cartridge and the control device.

FIG. 30A illustrates a partial exploded perspective view of an inner frame of a control device according to an example implementation of the present disclosure. In particular, FIG. 31 illustrates a portion of an inner frame 3015 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 3015 of the depicted implementation includes a cartridge receiving chamber 3012 and a flange 3050 defined at an upper end thereof. The inner frame 3015 of the depicted implementation also includes a plurality of magnets 3052 located proximate the upper flange 3050 of the inner frame 3015. In the depicted implementation, there are four individual magnets 3052A, 3052B, 3052C, 3052D, each of which has a substantially block-like or rectangular prismatic shape, although in other implementation more or less individual magnets may be used and the magnets may have different shapes and/or sizes. Reference is made to the possible magnet materials discussed above. In the depicted implementation, the magnets 3052A, 3052B, 3052C, 3052D are approximately equally spaced around the outside of the inner frame 3015 and below the upper flange 3050 thereof. Each of the plurality of magnets is located inside a corresponding magnet receiving feature 3053, which, in the depicted implementation, is an extension of the upper flange 3050. Although other methods are possible, the magnets 3052A, 3052B, 3052C, 3052D of the depicted implementation may be affixed inside the respective magnet receiving features 3053 via a press-fit and/or adhesive connection, or via an insert molding process.

In addition, the inner frame 3015 of the depicted implementation also includes a pair of metal plates 3020A, 3020B located in the upper flange 3050 of the inner frame 3015, which are exposed through openings in the upper flange 3050. Although other configurations are possible, in the depicted implementation, the metal plates have a curved shape configured to match a portion of the upper flange 3050, and the top surfaces of the magnets 3020A, 3020B are substantially flush with the top surface of the upper flange 3050. In the depicted implementation, the metal plates 3020A, 3020B are operatively connected to the battery of the control device in order, as will be discussed below, to provide power to the heater of an inserted cartridge. In various implementations, the metal plates 3020A, 3020B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 30B illustrates a perspective view of a cartridge according to an example implementation of the present disclosure, and FIG. 30C illustrates a bottom view of a cartridge according to an example implementation of the present disclosure. In particular, FIGS. 30B and 30C illustrate a cartridge 2900 that includes a tank 2902 that is defined by an outer tank wall 2904 that includes a proximal end 2906 and a distal end 2908, which is closed. In many aspects, the cartridge 2900 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 2900 of the depicted implementation includes a mouthpiece 2910 that is defined by an outer mouthpiece wall 2912 that includes a proximal end 2914 with an exit portal defined therein, and a distal end 2916 that engages the proximal end 2906 of the tank 2902. In the depicted implementation, the mouthpiece wall 2912 includes a flange 2950 positioned between the proximal end 2914 and the distal end 2916 thereof. The cartridge 2900 of the depicted implementation also includes two pairs of metal plates. In particular, the cartridge 2900 includes a pair of short metal plates 2925A, 2925B, which extend around opposite corners of the flange 2950 of cartridge 2900, and a pair of long metal plates 2952A, 2952B, which extend around the other opposite corners of the flange 2950 and terminate proximate the ends of the pair of short metal plates 2925A, 2925B. In the depicted implementation, each of the first pair of metal plates 2925A, 2925B has a curved shape configured to match a portion of the flange 2950, and each of the second pair of metal plates 2952A, 2952B has a curved shape configured to match another portion of the flange 2950. In the depicted implementation, the first and second pairs of metal plates 2925A, 2925B, 2952A, 2952B are affixed to the bottom of the flange 2950 of the mouthpiece 2910 via an adhesive, although in other implementations other methods of attachment of possible, including, for example, via an insert molding process. In the depicted implementation, the first pair of metal plates 2925A, 2925B are operatively connected to a heater 2920 (see FIG. 31) of the cartridge 2900. In various implementations, the short metal plates 3020A, 3020B may be constructed of any electrically conductive material, including, for example, but not limited to, copper, beryllium copper, aluminum, platinum, gold, silver, iron, steel, brass, bronze, graphite, conductive ceramic materials, and/or any combination thereof. In various implementations, the long metal plates 2952A, 2952B may comprise any material configured to be attracted by a magnet, such as various ferromagnetic materials, including, but not limited to, iron, nickel, cobalt, alloys such as steel, and/or any combination thereof.

In various implementations, a portion of the cartridge 2900 of FIGS. 30B and 30C is configured to be coupled with the cartridge receiving chamber 3012 of the inner frame 3015 of FIG. 30A, such that magnetic and electrical connections are created between the cartridge and the control device. In particular, FIG. 30A illustrates a partial cross-section view of the cartridge 2900 coupled with the inner frame 3015 of the control device. As illustrated in the figure, when the cartridge 2900 of the depicted implementation is coupled with the inner frame 3015 of the control device, a magnetic connection is created between the plurality of magnets 3052A, 3052B, 3052C, and 3052D located in the inner frame 3015 of the control device and the second pair of metal plates 2952A, and 2952B of the cartridge 2900. In addition, when the cartridge 2900 of the depicted implementation is coupled with the inner frame 3015, an electrical connection is created between the pair metal plates 3020A, 3020B of the inner frame 3015 of the control device and the first pair of metal plates 2925A, 2925B of the cartridge 2900. As such, when the cartridge 2900 is received in the inner frame 3015 of the control device, the heater 2920 of the cartridge 2900 may be operatively connected to the battery of the control device. As such, when the cartridge 2900 of the depicted implementation is coupled with the inner frame 3015 of the control device, the cartridge 2900 is mechanically biased into connection with the inner frame 3015 of the control device such that the electrical connection is maintained between the cartridge and the control device.

FIG. 32A illustrates a partial exploded perspective view of an inner frame of a control device according to an example implementation of the present disclosure. In particular, FIG. 32A illustrates a portion of an inner frame 3215 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 3215 of the depicted implementation includes a cartridge receiving chamber 3212 and a flange 3250 defined at an upper end thereof. The inner frame 3215 of the depicted implementation also includes a plurality of magnets 3252 located proximate the upper flange 3250 of the inner frame 3015. In the depicted implementation, there are four individual magnets 3252A, 3252B, 3252C, 3252D, each of which has a substantially block-like or rectangular prismatic shape, although in other implementation more or less individual magnets may be used and the magnets may have different shapes and/or sizes. Reference is made to the possible magnet materials discussed above. In the depicted implementation, the magnets 3252A, 3252B, 3252C, 3252D are approximately equally spaced around the outside of the inner frame 3215 and below the upper flange 3250 thereof. Each of the plurality of magnets is located inside a corresponding magnet receiving feature 3253, which, in the depicted implementation, is an extension of the upper flange 3250. Although other methods are possible, the magnets 3252A, 3252B, 3252C, 3252D of the depicted implementation may be affixed inside the respective magnet receiving features 3253 via a press-fit and/or adhesive connection, or via an insert molding process.

In addition, the inner frame 3215 of the depicted implementation also includes a pair of metal plates 3220A, 3220B located on opposite corners of the upper flange 3250 of the inner frame 3215, and which are exposed through openings in the upper flange 3250. Although other configurations are possible, in the depicted implementation, the metal plates have a curved shape configured to match a portion of the upper flange 3250, and the top surfaces of the magnets 3220A, 3220B are substantially flush with the top surface of the upper flange 3050. In the depicted implementation, the metal plates 3020A, 3020B are operatively connected to the battery of the control device in order, as will be discussed below, to provide power to the heater of an inserted cartridge. In various implementations, the metal plates 3220A, 3220B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 32B illustrates a perspective view of a cartridge according to an example implementation of the present disclosure, and FIG. 32C illustrates a bottom view of a cartridge according to an example implementation of the present disclosure. In particular, FIGS. 32B and 32C illustrate a cartridge 3100 that includes a tank 3102 that is defined by an outer tank wall 3104 that includes a proximal end 3106 and a distal end 3108, which is closed. In many aspects, the cartridge 3100 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 3100 of the depicted implementation includes a mouthpiece 3110 that is defined by an outer mouthpiece wall 3112 that includes a proximal end 3114 with an exit portal defined therein, and a distal end 3116 that engages the proximal end 3106 of the tank 3102. In the depicted implementation, the mouthpiece wall 3112 includes a flange 3150 positioned between the proximal end 3114 and the distal end 3116 thereof. The cartridge 3100 of the depicted implementation also includes a pair of separate metal plates. In particular, the cartridge 3100 includes a pair of metal plates 3152A, 3152B, which are located on opposite sides of cartridge 3100. In the depicted implementation, each of the metal plates 3152A, 3152B has a curved shape configured to match a portion of the flange 3150. In particular, each plate 3152A, 3152B begins proximate a first corner of the flange 3150 extends around that corner and a second corner of the flange 3150 and ends proximate the corner of the flange opposite the first corner. In the depicted implementation, the metal plates 3152A, 3152B are affixed to the bottom of the flange 3150 of the mouthpiece 3110 via an adhesive, although in other implementations other methods of attachment of possible, including, for example, via an insert molding process. In the depicted implementation, the metal plates 3152A, 3152B are operatively connected to a heater 3120 (see FIG. 33) of the cartridge 3100. In various implementations, the metal plates 3152A, 3152B may comprise any material configured to be electrically conductive and attracted by a magnet, such as various ferromagnetic materials, including, but not limited to, iron, nickel, cobalt, alloys such as steel, and/or combinations thereof.

In various implementations, a portion of the cartridge 3100 of FIGS. 32B and 32C is configured to be coupled with the cartridge receiving chamber 3212 of the inner frame 3215 of FIG. 32A, such that magnetic and electrical connections are created between the cartridge and the control device. In particular, FIG. 33 illustrates a partial cross-section view of the cartridge 3100 coupled with the inner frame 3215 of the control device. As illustrated in the figure, when the cartridge 3100 of the depicted implementation is coupled with the inner frame 3215 of the control device, a magnetic connection is created between the plurality of magnets 3252A, 3252B, 3252C, and 3252D located in the inner frame 3215 of the control device and the metal plates 3152A, 3152B of the cartridge 3100. In addition, when the cartridge 3100 of the depicted implementation is coupled with the inner frame 3215, an electrical connection is created between the metal plates 3220A, 3220B of the inner frame 3215 of the control device and the metal plates 3152A, 3152B of the cartridge 3100. As such, when the cartridge 3100 is coupled with the inner frame 3215 of the control device, the heater 3120 of the cartridge 3100 may be operatively connected to the battery of the control device. As such, when the cartridge 3100 of the depicted implementation is coupled with the inner frame 3215 of the control device, the cartridge 3100 is mechanically biased into connection with the inner frame 3215 of the control device such that the electrical connection is maintained between the cartridge and the control device.

FIG. 34 illustrates a partial exploded perspective view of an inner frame of a control device according to an example implementation of the present disclosure. In particular, FIG. 34 illustrates a portion of an inner frame 3415 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 3415 of the depicted implementation includes a cartridge receiving chamber 3412 and a flange 3450 defined at an upper end thereof. The inner frame 3415 of the depicted implementation also includes a pair of magnets 3452A, 3452B on opposite sides of the flange 3450. In the depicted implementation, each of the magnets 3452A, 3452B has a substantially block-like or rectangular prismatic shape. Reference is made to the possible magnet materials discussed above. In other implementations, more or less magnets may be used and the magnets may have different shapes and/or sizes. In the depicted implementation, each of the magnets 3452A, 3452B is located below the top surface of the flange 3450 and inside of respective magnet receiving feature 3453, which, in the depicted implementation, is an extension of the upper flange 3450. Although other methods are possible, the magnets 3452A, 3252B of the depicted implementation may be affixed inside the respective magnet receiving features 3453 via a press-fit and/or adhesive connection, or via an insert molding process.

In addition, the inner frame 3415 of the depicted implementation also includes a pair of metal plates 3420A, 3420B located on opposite sides of the upper flange 3450 of the inner frame 3215, and which are exposed through openings in the upper flange 3450. In the depicted implementation, each of the metal plates 3420A, 3420B is located inside of respective receiving feature 3455, which, in the depicted implementation, comprises part of the upper flange 3450. Although other configurations are possible, in the depicted implementation, the metal plates have a substantially block-like or rectangular prismatic shape, and the top surfaces of the metal plates 3420A, 3420B are substantially flush with the top surface of the upper flange 3450. In the depicted implementation, the metal plates 3420A, 3420B are operatively connected to the battery of the control device in order, as will be discussed below, to provide power to the heater of an inserted cartridge. In various implementations, the metal plates 3420A, 3420B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 35A illustrates a partial perspective view of a cartridge coupled with an inner frame of a control device according to an example implementation of the present disclosure, and FIG. 35B illustrates a partial transparent perspective view of a cartridge coupled with an inner frame of a control device according to an example implementation of the present disclosure. In particular, FIGS. 35A and 35B illustrate a cartridge 3300 that includes a tank (not visible) that is defined by an outer tank wall that includes a proximal end and a distal end, which is closed. In many aspects, the cartridge 3300 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 3300 of the depicted implementation includes a mouthpiece 3310 that is defined by an outer mouthpiece wall 3312 that includes a proximal end 3314 with an exit portal 3315 defined therein, and a distal end (not visible) that engages the proximal end of the tank. In the depicted implementation, the mouthpiece wall 3312 includes a flange 3350 positioned between the proximal end 3314 and the distal end thereof. The cartridge 3300 of the depicted implementation also includes a pair of metal plates. In particular, the cartridge 3300 includes metal plates 3352A, 3352B, which extend around respective adjacent sides of the flange 3350 of the cartridge such that they extend around on set of opposite corners of the flange 3350 but do not extend around the other set of opposite corners of the flange 3350. In the depicted implementation, each of the metal plates 3352A, 3352B has a curved J-shape configured to match a portion of the flange 3350 as described above, and to operatively connect to a heater 3320 of the cartridge 3300. In the depicted implementation, the metal plates 3352A, 3352B are affixed to the bottom of the flange 3350 of the mouthpiece 3310 via an adhesive, although in other implementations other methods of attachment of possible, including, for example, via an insert molding process. In various implementations, the metal plates 3352A, 3352B may comprise any material configured to be electrically conductive and attracted by a magnet, such as various ferromagnetic materials, including, but not limited, to iron, nickel, cobalt, alloys such as steel, and/or combinations thereof.

In various implementations, a portion of the cartridge 3300 is configured to be coupled with the cartridge receiving chamber 3412 of the inner frame 3415, such that magnetic and electrical connections are created between the cartridge and the control device. In particular, FIGS. 35A and 35B illustrate a partial perspective views of the cartridge 3300 coupled with the inner frame 3415 of the control device. As illustrated in the figures, when the cartridge 3300 of the depicted implementation is coupled with the inner frame 3415 of the control device, a magnetic connection is created between the magnets 3452A, 3452B located in the inner frame 3415 of the control device and the metal plates 3352A, 3352B of the cartridge 3300. In addition, when the cartridge 3300 of the depicted implementation is coupled with the inner frame 3415, an electrical connection is created between the metal plates 3420A, 3420B of the inner frame 3415 of the control device and the metal plates 3352A, 3352B of the cartridge 3300. As such, when the cartridge 3300 is coupled with the inner frame 3415 of the control device, the heater 3320 of the cartridge 3300 may be operatively connected to the battery of the control device. As such, when the cartridge 3300 of the depicted implementation is coupled with the inner frame 3415 of the control device, the cartridge 3300 is mechanically biased into connection with the inner frame 3415 of the control device such that the electrical connection is maintained between the cartridge and the control device.

FIG. 36A illustrates a partial perspective view of an inner frame of a control device according to an example implementation of the present disclosure. In particular, FIG. 36A illustrates a portion of an inner frame 3615 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 3615 of the depicted implementation includes a cartridge receiving chamber 3612 and a flange 3650 defined at an upper end thereof. The inner frame 3615 of the depicted implementation also includes a pair of magnets 3652A, 3652B on opposite sides of the flange 3650. In the depicted implementation, each of the magnets 3652A, 3652B has a substantially block-like or rectangular prismatic shape. Reference is made to the possible magnet materials discussed above. In other implementations, more or less magnets may be used and the magnets may have different shapes and/or sizes. In the depicted implementation, each of the magnets 3652A, 3652B is located below the top surface of the flange 3650 and inside of respective magnet receiving feature 3653, which, in the depicted implementation, is an extension of the upper flange 3650. Although other methods are possible, the magnets 3652A, 3652B of the depicted implementation may be affixed inside the respective magnet receiving features 3653 via a press-fit and/or adhesive connection, or via an insert molding process.

In addition, the inner frame 3615 of the depicted implementation also includes a pair of metal plates 3620A, 3620B located on opposite sides of the upper flange 3650 of the inner frame 3615. In the depicted implementation, each of the metal plates 3620A, 3620B is located below the top surface of the flange 3650 and inside of respective receiving feature 3655, which, in the depicted implementation, comprises part of the upper flange 3650. Although other configurations are possible, in the depicted implementation, the metal plates have a substantially block-like or rectangular prismatic shape. In the depicted implementation, the metal plates 3620A, 3620B are operatively connected to the battery of the control device in order, as will be discussed below, to provide power to the heater of an inserted cartridge. In various implementations, the metal plates 3620A, 3620B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 36B illustrates a partial transparent perspective view of a cartridge coupled with an inner frame of a control device according to an example implementation of the present disclosure. In particular, FIG. 36B illustrates a cartridge 3500 that includes a tank 3502 that is defined by an outer tank wall 3504 that includes a proximal end 3506 and a distal end 3508, which is closed. In many aspects, the cartridge 3500 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 3500 of the depicted implementation includes a mouthpiece 3510 that is defined by an outer mouthpiece wall 3512 that includes a proximal end 3514 with an exit portal 3515 defined therein, and a distal end 3516 that engages the proximal end 3506 of the tank 3502. In the depicted implementation, the mouthpiece wall 3512 includes a flange 3550 positioned between the proximal end 3514 and the distal end 3516 thereof. The cartridge 3500 of the depicted implementation also includes a metal plate 3552, which is disposed below the flange 3550. In the depicted implementation, the metal plate 3552 is affixed to the bottom of the flange 3550 of the mouthpiece 3510 via an adhesive, although in other implementations other methods of attachment of possible, including, for example, via an insert molding process, a press-fit connection, a heat staking connection, etc. The cartridge 3500 also includes a pair of conductive springs 3525A, 3525B located on opposite sides of the mouthpiece 3510. In the depicted implementation, each of the conductive springs includes a contact surface 3565A, 3565B that is exposed through a respective opening in the mouthpiece 3510 below the flange 3550. In the depicted implementation, the conductive springs 3525A, 3525B may be affixed inside the mouthpiece 3510 of the cartridge 3500 via an adhesive, although in other implementations other methods of attachment of possible, including, for example, via an insert molding process. In the depicted implementation, the conductive springs 3525A, 3525B are operatively connected to a heater 3520 (see FIG. 37) of the cartridge 3500. In various implementations, the conductive springs 3525A, 3525B may be constructed of any electrically conductive material, including, for example, but not limited to, copper, beryllium copper, aluminum, platinum, gold, silver, iron, steel, brass, bronze, graphite, conductive ceramic materials, and/or any combination thereof. In various implementations, the metal plate 3552 may comprise any material configured to be attracted by a magnet, such as various ferromagnetic materials, including, but not limited, to iron, nickel, cobalt, and alloys such as steel.

In various implementations, a portion of the cartridge 3500 is configured to be coupled with the cartridge receiving chamber 3612 of the inner frame 3615, such that magnetic and electrical connections are created between the cartridge and the control device. In particular, FIG. 37 illustrates a partial cross-section view of the cartridge 3500 coupled with the inner frame 3615 of a control device. As illustrated in the figures, when the cartridge 3500 of the depicted implementation is coupled with the inner frame 3615 of the control device, a magnetic connection is created between the magnets 3652A, 3652B located in the inner frame 3615 of the control device and the metal plate 3552 of the cartridge 3500. In addition, when the cartridge 3500 of the depicted implementation is coupled with the inner frame 3615, an electrical connection is created between the metal plates 3620A, 3620B of the inner frame 3615 of the control device and the conductive springs 3525A, 3525B of the cartridge 3500. As such, when the cartridge 3500 is coupled with the inner frame 3615 of the control device, the heater 3520 of the cartridge 3500 may be operatively connected to the battery of the control device. As such, when the cartridge 3500 of the depicted implementation is coupled with the inner frame 3615 of the control device, the cartridge 3500 is mechanically biased into connection with the inner frame 3615 of the control device such that the electrical connection is maintained between the cartridge and the control device.

FIG. 38A illustrates a partial transparent perspective view of an inner frame of a control device according to an example implementation of the present disclosure. In particular, FIG. 38A illustrates a portion of an inner frame 3815 for use with a corresponding control device. In many aspects, the control device may have a similar configuration and may include similar components (and similar configuration and component variations) as that of the control device 200 described above. As such, reference is made to the pertinent discussions of these configurations and components (and configuration and component variations), which will not be repeated here.

As shown in the figures, the inner frame 3815 of the depicted implementation includes a cartridge receiving chamber 3812 and an upper flange 3850. The inner frame 3815 of the depicted implementation also includes a plurality of magnets 3852 located proximate the upper flange 3850 of the inner frame 3815. In particular, the depicted implementation includes two pairs of cylindrical magnets 3852A, 3852B, 3852C, 3852D, each pair located on opposite sides of the inner frame 3815 and extending proximate the upper flange 3850 thereof, with each of the plurality of magnets being located inside a corresponding magnet receiving feature 3853, which, in the depicted implementation, is an extension of the upper flange 3850. Reference is made to the possible magnet materials discussed above. Although other methods are possible, the magnets 3852 of the depicted implementation may be affixed inside the magnet receiving features 3853 via a press-fit and/or adhesive connection, or via an insert molding process.

In addition, the inner frame 3815 of the depicted implementation also includes a pair of conductive pins 3820A, 3820B located in the inner frame 3815 and proximate the upper flange 3850 thereof. In the depicted implementation, the conductive pins 3820A, 3820B comprise cylindrical metal pins located on opposite sides of the inner frame 3815 and which extend through the upper flange 3850. Although other configurations are possible, in the depicted implementation, the top surfaces of the metal pins 3820A, 3820B extend above (e.g., extend slightly above) the top surface of the upper flange 3850. In the depicted implementation the conductive pins 3820A, 3820B are operatively connected to the battery of the control device in order, as will be discussed below, to provide power to the heater of an inserted cartridge. In various implementations, the conductive pins 3820A, 3820B may be constructed of any electrically conductive material, including, for example, but not limited to, copper, beryllium copper, aluminum, platinum, gold, silver, iron, steel, brass, bronze, graphite, conductive ceramic materials, and/or any combination thereof.

FIG. 38B illustrates a partial perspective view of a cartridge according to an example implementation of the present disclosure. In particular, FIG. 38B illustrates a cartridge 3700 that includes a tank 3702 that is defined by an outer tank wall 3704 that includes a proximal end 3706 and a distal end (not visible), which is closed. In many aspects, the cartridge 3700 may have a similar configuration and may include similar components (and similar configuration and component variations) as that of the cartridge 300 described above, which will not be repeated here. As such, reference is made to the pertinent discussions of these configurations and components (and configuration and component variations).

The cartridge 3700 of the depicted implementation includes a mouthpiece 3710 that is defined by an outer mouthpiece wall 3712 that includes a proximal end 3714 with an exit portal (not visible) defined therein, and a distal end 3716 that engages the proximal end 3706 of the tank 3702. In the depicted implementation, the mouthpiece wall 3712 includes a flange 3750 positioned between the proximal end 3714 and the distal end 3716 thereof. The cartridge 3700 of the depicted implementation also includes a pair of separate metal plates 3752A, 3752B which comprise part of the flange 3750. In the depicted implementation, each of the metal plates 3752A, 3752B includes an integrated spring contact 3765A, 3765B that extends below the flange 3750. In the depicted implementation, the metal plates 3752A, 3752B are affixed to the flange 3750 of the mouthpiece 3710 via an adhesive, although in other implementations other methods of attachment of possible, including, for example, via an insert molding process, a press-fit connection, a heat staking connection, etc. In the depicted implementation, the separate metal plates 3752A, 3752B are operatively connected to a heater 3720 (see FIG. 39) of the cartridge 3700. In various implementations, the metal plates 3752A, 3752B may comprise any material configured to be electrically conductive and attracted by a magnet, such as various ferromagnetic materials, including, but not limited, to iron, nickel, cobalt, and alloys such as steel. In some implementations, one or both of the metal plates may be constructed of a bi-metal material, such as a bi-metal plate, in which one or more portions of the plate that are configured to contact the conductive pins comprise an electrically conductive spring material, and one or more portions of the plate that are configured to contact the magnets comprise a different material that suitable for attraction to a magnet.

In various implementations, a portion of the cartridge 3700 of FIG. 38B is configured to be coupled with the cartridge receiving chamber 3812 of the inner frame 3815 of FIG. 38A, such that magnetic and electrical connections are created between the cartridge and the control device. In particular, FIG. 39 illustrates a partial cross-section view of the cartridge 3700 coupled with the inner frame 3815 of the control device. As illustrated in the figure, when the cartridge 3700 of the depicted implementation is coupled with the inner frame 3815 of the control device, a magnetic connection is created between the plurality of magnets 3852A, 3852B, 3852C, 3852D located in the inner frame 3815 of the control device and the metal plates 3752A, 3752B of the cartridge 3700. In addition, when the cartridge 3700 of the depicted implementation is coupled with the inner frame 3815, an electrical connection is created between the pair conductive pins 3820A, 3820B of the inner frame 3815 of the control device and the integrated spring contacts 3765A, 3765B of the cartridge 3700. As such, when the cartridge 3700 is received in the inner frame 3815 of the control device, the heater 3720 of the cartridge 3700 may be operatively connected to the battery of the control device. Therefore, when the cartridge 3700 of the depicted implementation is coupled with the inner frame 3815 of the control device, the cartridge 3700 is mechanically biased into connection with the inner frame 3815 of the control device such that the electrical connection is maintained between the cartridge and the control device.

It should be noted that in various implementations, some components of the either the control device, the cartridge, or both the control device and the cartridge may be substituted with other components with similar function but different structure. For example, several of the implementations above describe the use of spring-loaded pins (e.g., electrical pogo pins) in an inner frame of a control device, wherein the spring-loaded pins are connected to the battery of the control device. In various alternate implementations, one or both of the electrical pogo pins used in those implementations may be replaced with metal plates that include formed contact surfaces. An example of such an implementation is shown in FIG. 40, which illustrates a partial cross-section view of a cartridge coupled with an inner frame of a control device according to an example implementation of the present disclosure. In particular, FIG. 40 illustrates a cartridge 3900 coupled with the inner frame 4015 of a control device. In the depicted implementation, spring-loaded electrical pins have been replaced with metal plates 4020 that include rounded deflecting contact areas 4065, which are configured to engage electrical contacts of the cartridge. In various implementations, the metal plate 4020 may be constructed of any electrically conductive material, including, for example, but not limited to, copper, beryllium copper, aluminum, platinum, gold, silver, iron, steel, brass, bronze, graphite, conductive ceramic materials, and/or any combination thereof. Thus, as illustrated in the figure, when the cartridge 3900 of the depicted implementation is coupled with the inner frame 4015 of the control device, a magnetic connection is created between magnets of the control device and the metal plate 3952 of the cartridge 3900, and an electrical connection is created between the contact areas 4065 of the metal plates 4020 of the inner frame 4015 of the control device and electrical contacts 3925 of the cartridge 3900 that are connected to a heater 3920. As such, when the cartridge 3900 is coupled with the inner frame 4015 of the control device, the heater 3920 of the cartridge 3900 may be operatively connected to the battery of the control device.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. A cartridge for use with a control device of an aerosol delivery device, the cartridge comprising:
a mouthpiece portion and a tank, the mouthpiece portion having a proximal end and a distal end, the proximal end of the mouthpiece portion having an exit portal defined therethrough, the tank further defining a proximal end and a closed distal end and being configured to contain a liquid composition,
wherein the cartridge includes at least one connector configured to provide a magnetic and an electrical connection between the cartridge and the control device such that the cartridge can be removably and operatively received into a cartridge receiving chamber of the control device, wherein the distal end of the mouthpiece portion is located proximate the proximal end of the tank, and wherein the at least one connector of the cartridge is located on the mouthpiece portion.

2. The cartridge of claim 1, further comprising:
a flange located between the proximal and distal ends of the mouthpiece portion;
a metal plate located below the flange; and
a pair of conductive plugs,
wherein the magnetic connection is created via the metal plate of the cartridge, and wherein the electrical connection is created via the conductive plugs of the cartridge.

3. The cartridge of claim 1 the cartridge further comprising:
a flange located between the proximal and distal ends of the mouthpiece portion;
at least one attachment element located in the flange of the cartridge; and
a pair of conductive plugs,
wherein the magnetic connection is created via the at least one attachment element of the cartridge, and wherein the electrical connection is created via the conductive plugs of the cartridge.

4. The cartridge of claim 1, further comprising:
a flange located between the proximal and distal ends of the mouthpiece portion;
a pair of metal plates, the metal plates comprising a portion of the flange of the cartridge,
wherein both the magnetic connection and the electrical connection are created via the pair of separate metal plates of the cartridge.

5. The cartridge of claim 1, further comprising:
a pair of metal plates, each metal plate including receiving detents on opposite ends thereof,
wherein the magnetic connection is created via the receiving detents of the metal plates of the cartridge, and wherein the electrical connection is created via the metal plates of the cartridge.

6. The cartridge of claim 1, further comprising:
a flange located between the proximal and distal ends of the mouthpiece portion;
a pair of pointed sliding metal plates located in the flange; and
a pair of conductive plugs,
wherein the magnetic connection is created via the pointed sliding metal plates of the cartridge, and wherein the electrical connection is created via the conductive plugs of the cartridge.

7. The cartridge of claim 1, further comprising:
a flange located between the proximal and distal ends of the mouthpiece portion; and
a pair of metal plates comprising a portion of a bottom surface of the flange,
wherein the magnetic connection is created via the metal plates of the cartridge, and wherein the electrical connection is created the metal plates of the cartridge.

8. The cartridge of claim 1, further comprising:
a flange located between the proximal and distal ends of the mouthpiece portion; and
first and second pairs of metal plates located below the flange,
wherein the magnetic connection is created via the second pair of metal plates of the cartridge, and wherein the electrical connection is created via the first pair of metal plates of the cartridge.

9. The cartridge of claim 1, further comprising:
a flange located between the proximal and distal ends of the mouthpiece portion; and
a pair of metal plates located below the flange,
wherein the magnetic connection is created via the pair of metal plates of the cartridge, and wherein the electrical connection is created via the pair of metal plates of the cartridge.

10. The cartridge of claim 1, further comprising:
a flange located between the proximal and distal ends of the mouthpiece portion; and
a pair of metal plates, the metal plates comprising a portion of the flange of the cartridge, wherein the magnetic connection is created via the pair of metal plates of the cartridge, and the electrical connection is created via the pair of metal plates of the cartridge.

11. The cartridge of claim 1, further comprising:
a flange located between the proximal and distal ends of the mouthpiece portion;
a metal ring that comprises a portion of the flange; and
a pair of conductive spring contacts,
wherein the magnetic connection is created via the metal ring of the cartridge, and wherein the electrical connection is created via the pair of conductive spring contacts of the cartridge.

12. The cartridge of claim 1, further comprising:
a flange located between the proximal and distal ends of the mouthpiece portion; and
a pair of metal plates comprising a portion of a bottom surface of the flange, each metal plate including an integrated spring contact,
wherein the magnetic connection is created via the metal plates of the cartridge, and wherein the electrical connection is created via the integrated spring contacts of the metal plates of the cartridge.

* * * * *